(12) United States Patent
Neisz et al.

(10) Patent No.: US 6,652,450 B2
(45) Date of Patent: Nov. 25, 2003

(54) IMPLANTABLE ARTICLE AND METHOD FOR TREATING URINARY INCONTINENCE USING MEANS FOR REPOSITIONING THE IMPLANTABLE ARTICLE

(75) Inventors: Johann J. Neisz, Coon Rapids, MN (US); John W. Westrum, Jr., Prior Lake, MN (US); Christopher H. Porter, Woodinville, WA (US)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/917,562

(22) Filed: Jul. 27, 2001

(65) Prior Publication Data

US 2002/0107430 A1 Aug. 8, 2002

Related U.S. Application Data

(60) Provisional application No. 60/306,915, filed on Jul. 20, 2001, provisional application No. 60/295,068, filed on Jun. 1, 2001, provisional application No. 60/281,350, filed on Apr. 4, 2001, provisional application No. 60/269,829, filed on Feb. 20, 2001, and provisional application No. 60/263,472, filed on Jan. 23, 2001.

(51) Int. Cl.[7] .................................................. A61F 2/00
(52) U.S. Cl. ...................................................... 600/30
(58) Field of Search .............................. 600/29, 30, 37; 128/885

(56) References Cited

U.S. PATENT DOCUMENTS

| | | |
|---|---|---|
| 2,738,790 A | 3/1956 | Todt et al. |
| 3,054,406 A | 9/1962 | Usher |
| 3,124,136 A | 3/1964 | Usher |
| 3,182,662 A | 5/1965 | Shirodkar |

(List continued on next page.)

FOREIGN PATENT DOCUMENTS

| | | |
|---|---|---|
| DE | 2305815 | 2/1973 |
| DE | 4220283 C2 | 5/1994 |
| EP | 0470308 A1 | 2/1992 |
| EP | 0 650 703 A1 | 6/1994 |

(List continued on next page.)

OTHER PUBLICATIONS

Beck, Peter R. et al., Treatment of Urinary Stress Incontinence With Anterior Colporrhaphy, Obstetrics and Gynecology, vol 59 (No. 3), pp. 269–274 (Mar. 1982).

Benderev, Theodore V., MD, A Modified Percutaneous Outpatient Bladder Neck Suspension System, Journal of Urology, vol. 152, pp. 2316–2320 (Dec. 1994).

Benderev, Theodore V., MD, Anchor Fixation and Other Modifications of Endoscopic Bladder Neck Suspension, Urology, vol 40, No. 5, pp. 409–418 (Nov. 1992).

Das, Sakti et al., Laparoscopic Colpo–Suspension, The Journal of Urology, vol. 154, pp. 1119–1121 (Sep. 1995).

Gilja, Ivan et al., A Modified Raz Bladder Neck Suspension Operation (Transvaginal Burch), The Journal of Urology, vol. 153, pp. 1455–1457 (May 1995).

Gittes, Ruben F. et al., No–Incision Pubovaginal Suspension for Stress Incontinence, The Journal of Urology, vol. 138 (Sep. 1987).

(List continued on next page.)

Primary Examiner—Samuel G. Gilbert
(74) Attorney, Agent, or Firm—Oblon, Spivak, McClelland, Maier & Neustadt, P.C.

(57) ABSTRACT

An implantable article and method of use are disclosed to treat urological disorders. The biocompatible device includes a sling assembly configured to be minimally invasive and provide sufficient support to the target site. In addition, the configuration of the sling assembly also allows the position of the sling to be permanently changed during and/or after implantation.

36 Claims, 61 Drawing Sheets

U.S. PATENT DOCUMENTS

| | | |
|---|---|---|
| 3,311,110 A | 3/1967 | Singerman et al. |
| 3,384,073 A | 5/1968 | Van winkle, Jr. |
| 3,384,074 A | 5/1968 | Van winkle, Jr. |
| 3,472,232 A | 10/1969 | Earl |
| 3,763,860 A | 10/1973 | Clarke |
| 3,789,828 A | 2/1974 | Schulte |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,775,380 A | 10/1988 | Seedhom et al. |
| 4,857,041 A | 8/1989 | Annis et al. |
| 4,865,031 A | 9/1989 | O'Keeffe |
| 4,932,962 A | 6/1990 | Yoon et al. |
| 4,938,760 A | 7/1990 | Burton et al. |
| 4,969,892 A | 11/1990 | Burton et al. |
| 4,979,956 A * | 12/1990 | Silvestrini ............... 623/13.11 |
| 5,012,822 A | 5/1991 | Schwarz |
| 5,013,292 A | 5/1991 | Lemay |
| 5,019,032 A | 5/1991 | Robertson |
| 5,032,508 A | 7/1991 | Naughton et al. |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,544,664 A | 8/1996 | Benderev et al. |
| 5,562,689 A | 10/1996 | Green et al. |
| 5,591,163 A | 1/1997 | Thompson |
| 5,611,515 A | 3/1997 | Benderev et al. |
| 5,628,756 A | 5/1997 | Barker, Jr. et al. |
| 5,669,935 A | 9/1997 | Rosenman et al. |
| 5,807,403 A | 9/1998 | Beyar et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,944,732 A | 8/1999 | Raulerson et al. |
| 5,945,122 A | 8/1999 | Abra et al. |
| 5,972,000 A | 10/1999 | Beyar et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,053,935 A | 4/2000 | Brenneman et al. |
| 6,068,591 A | 5/2000 | Bruckner et al. |
| 6,071,290 A | 6/2000 | Compton |
| 6,106,545 A | 8/2000 | Egan |
| 6,110,101 A | 8/2000 | Tihon et al. |
| 6,117,067 A | 9/2000 | Gil-Vernet |
| 6,168,423 B1 | 1/2001 | Risvi |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van de Burg et al. |
| 6,382,214 B1 | 5/2002 | Raz et al. |
| 6,406,423 B1 | 6/2002 | Scetbon |
| 6,423,080 B1 | 7/2002 | Gellman et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 2001/0018549 A1 | 8/2001 | Scetbon |
| 2001/0023356 A1 | 9/2001 | Raz |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0099260 A1 | 7/2002 | Suslian et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |

FOREIGN PATENT DOCUMENTS

| | | |
|---|---|---|
| EP | 0 643 945 A2 | 7/1994 |
| EP | 1093758 A1 | 10/2000 |
| SU | 1225547 A1 | 4/1986 |
| WO | 93/17635 | 3/1993 |
| WO | WO 98/35616 A1 | 8/1998 |
| WO | WO 99/52450 A2 | 10/1999 |
| WO | WO 00/64370 A1 | 2/2000 |
| WO | 00/18319 | 4/2000 |
| WO | 00/57812 | 10/2000 |
| WO | 00/74594 A1 | 12/2000 |
| WO | 00/74613 A1 | 12/2000 |
| WO | 00/74633 A2 | 12/2000 |
| WO | 01/26581 A1 | 4/2001 |
| WO | WO 01/39670 A1 | 6/2001 |
| WO | 01/45589 A1 | 6/2001 |

| | | |
|---|---|---|
| WO | 01/56499 A1 | 8/2001 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/071953 A2 | 9/2002 |
| WO | WO 02/078552 A1 | 10/2002 |

OTHER PUBLICATIONS

Holschneider, C. H., et al., The Modified Pereyra Procedure in Recurrent Stress Urinary Incontinence: A 15–year Review, Obstetrics & Gynecology, vol. 83, No. 4, pp. 573–578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648–652 (Apr. 1998).

Klutke, Carl et al., The Anatomy of Stress Incontinence: Magnetic Resonance Imaging of the Female Bladder Neck and Urethra, The Journal of Urology, vol 143, pp. 563–566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294–296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Leach, Gary E., et al., Female Stress Urinary Incontinence Clinical Guidelines Panel Report on Surgical Management of Female Stress Urinary Incontinence, American Urological Association, vol. 158, pp. 875–880 (Sep. 1997).

Leach, Gary E., MD, Bone Fixation Technique for Transvaginal Needle Suspension, Urology vol XXXI, No. 5, pp. 388–390 (May 1988).

Loughlin, Kevin R. et al., Review of an 8–Year Experience with Modifications of Endoscopic Suspension of the Bladder Neck for Female Stress Incontinence, The Journal of Urology, vol. 143, pp. 44–45 (1990).

McGuire, Edward J. et al., Experience with Pubovaginal Slings for Urinary Incontinence at the University of Michigan, Journal of Urology, vol. 138, pp. 90–93(1987).

McGuire, Edward J., M.D., The Sling Procedure for Urinary Stress Incontinence, Profiles in Urology, pp. 3–18.

McGuire, Edward J. et al., Abdominal Fascial Slings, Slings, Raz Female Urology, p 369–375 (1996).

McKiel, Charles F. Jr., et al, Marshall–Marchetti Procedure Modification, vol 96, pp. 737–739 (Nov. 1966).

Mitek Brochure, Therapy of Urinary Stress Incontinence in Women Using Mitek GIII Anchors, by Valenzio C. Mascio, MD.

Morgan, J. E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Parra, R. O., et al, Experience with a Simplified Technique for the Treatment of Female Stress Urinary Incontinence, British Journal of Urology, pp. 615–617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical.

Pereyra, Armand J. et al, Pubourethral Supports in Perspective: Modified Pereyra Procedure for Urinary Incontinence, Obstetrics and Gynecology, vol. 59, No. 5, pp 643–648 (May 1982).

Petros, Peter E. Papa et al., Part IV: Surgical Applications of the Theory—Developement of the Intravaginal Sling Pklasty (IVS) Procedure, Scandinavian Journal of Neurourology and Urodynamics, Sup 153, pp. 53–54 (1993).

Petros, Peter E. Papa et al., The Role of a Lax Posterior Vaginal Fornix in the Causation of Stress and Urgency Symptoms: A Preliminary Report, Acta Obstet Gynecol Scand, vol 69, Sup 153, pp. 71–73 (1990).

Raz, Shlomo, et al., The Raz Bladder Neck Suspension Results in 206 Patients, The Journal of Urology, pp. 845–846 (1992).

Raz, Shlomo, MD, Modified Bladder Neck Suspension for Female Stress Incontinence, Urology, vol. XVII, No. 1, pp. 82–85 (Jan. 1981).

TVT Tension–free Vaginal Tape, Gynecare, Ethicon, Inc., 23 pages (1999).

Waxman, Steve et al., Advanced Urologic Surgery for Urinary Incontinence, The Female Patient, pp. 93–100, vol 21 (Mar. 1996).

Webster, George D., Female Urinary Incontinence, Urologic Surgery, pp. 665–679.

Winter, Chester C., Peripubic Urethropexy for Urinary Stress Incontinence in Women, Urology, vol. XX, No. 4, pp. 408–411 (Oct. 1982).

Zimmern, Phillippe E. et al., Four–Corner Bladder Neck Suspension, Vaginal Surgery for the Urologist, vol 2, No. 1, pp. 29–36 (Apr. 1994).

Handa et al, Banked Human Fascia Lata for the Suburethral Sling Procedure: A Preliminary Report, Obstetrics & Gynecology, vol. 88 No. 6, 5 pages (Dec. 1996).

Staskin et al., A Comparison of Tensile Strength Among Three Preparations of irradiated and Non–Irradiated Human Fascia Lata Allografts, SPSS/PC+™ Base System Users Guide, Version 5.0, 6 pages Dec. 1992.

Donald R. Ostergard et al., Urogynecology and Urodynamics Theory and Practice, pp. 569–579 (1996).

John C. Burch, Urethrovaginal Fixation to Cooper's Ligament for Correction of Stress Incontinence, Cystocele, and Prolapse, Am. J. Obst. & Gyn, vol. 31, pp. 281–290 (1961).

G. A. McIndoe et al., The Aldridge Sling Procedure in the Treatment of Urinary Stress Incontinence, Aust. N Z Journal of Obstet Gynecology, pp. 238–240 (Aug. 1987).

J. Kersey, The Gauze Hammock Sling Operation in the Treatment of Stress Incontinence, British Journal of Obstetrics Gynecology, pp 945–949 (Oct. 1983).

John H. Ridley, Appraisal of the Goebell–Frangenheim–Stoeckel Sling Procedure, Am. J. Obst. & Gyn., vol. 95, pp. 714–721 (Jul. 1966).

J. E. Morgan, A Sling Operation, Using Marlex Polypropylene Mesh, for the Treatment of Recurrent Stress Incontinence, Am. J. Obst. & Gynecol, pp. 369–377 (Feb. 1970).

Stuart Stanton, Suprapubic Approaches for Stress Incontinence in Women, Journal of American Geriatic Society, vol. 38, pp. 348 (1990).

G. Narik, et al., A Simplified Sling Operation Suitable for Routine Use, Am. J. Obst. & Gyn., vol. 84, pp. 400–405 (1962).

Mickey Karram et al., Patch Procedure: Modified Transvaginal Fascia Lata Sling for Recurrent for Severe Stress Urinary Incontinence, vol. 75, pp. 461–463 (Mar. 1990).

Pat O'Donnell, Combined Raz Urethral Suspension and McGuire Pubovaginal Sling for Treatment of Complicated Stress Urinary Incontinence, Journal Arkansas Medical Society, vol. 88, pp. 389–392 (Jan. 1992).

Fred E. Bryans, Marlex Gauze Hammock Sling Operation with Cooper's Ligament Attachment in the Management of Recurrent Urinary Stress Incontinence, American Journal of Obstetrics and Gynecology, vol. 133, pp. 292–294 (Feb. 1979).

A. Korda et al., Experience with Silastic Slings for Female Urinary Incontinence, Aust NZ J. Obstet Gynaecol, vol. 29, pp. 150–154 (May 1989).

David H. Nichols, The Mersilene Mesh Gauze–Hammock for Severe Urinary Stress Incontinence, Obstetrics and Gynecology, vol. 41, pp. 88–93 (Jan. 1973).

Jeffrey P. Norris, et al., Use of Synthetic Material in Sling Surgery: A Minimally Invasive Approach, Journal of Endourology, vol. 10, pp. 227–230 (Jun. 1996).

Jong M. Choe et al., Gore–Tex Patch Sling: 7 Years Later, Urology, vol. 54, pp. 641–646 (1999).

David R. Staskin et al., The Gore–Tex Sling Procedure for Female Sphincteric Incontinence: Indications, Technique, and Results, World Journal of Urology, vol. 15, pp. 295–299 (1997).

C. Falconer, et al., Clinical Outcome and Changes in Connective Tissue Metabolism After Intravaginal Slingplasty in Stress Incontinent Women, The International Urogynecology Journal, vol. 7, pp. 133–137 (1966).

Mark D. Walters, Percutaneous Suburethral Slings: State of the Art, Presented at the conference of the American Urogynecologic Society, Chicago, (Oct. 2001).

Cook/Ob Gyn®, Urogynecology, Copyright Cook Urological Inc., pp. 1–36 (1996).

Shlomo Raz, Female Urology, pp. 80–86, 369–398, 435–442 (1996).

Irving L. Lichtenstein, et al., The Tension–Free Hernioplasty, The American Journal of Surgery, Scientific Papers, vol. 157, (Feb. 1989).

Jerry Blaivas, Commentary Pubovaginal Sling Procedure, Surgery for Female Urinary Incontinence, Current Operative Urology, pp. 93–101, (1990).

Edward J. McGuire et al., Experience with Pubovaginal Slings for Urinary Incontinence at the University of Michigan, Journal of Urology, V. 138, pp. 525–526 (1987).

J. Chassar Moir et.al., The Gauze–Hammock Operation, The Journal of Obstetrics and Gynaecology of British Commonwealth, vol. 75 No. 1, p. 1–9, (Jan. 1968).

C. Paul Hodgkinson et.al., Urinary Stress Incontinence in the Female, Department of Gynecology and Obstetrics, Henry Ford Hospital, vol 10, No. 5, p. 493–499, (Nov. 1957).

Armand J. Pereyra, M.D., F.A.C.S., A Simplified Surgical Procedure for Correction of Stress Incontinence in Women, West.J.Surg., Obst. & Gynec, p. 223–226, (Jul.–Aug. 1959).

Robert Zacharin, The Suspensory Mechanism of the Female Urethra, Journal of Anatomy, vol. 97, Part 3, pp. 423–427 (1963).

M. Asmussen et. al., Simultaneous Urethro–Cystometry with a New Technique, Scand J Urol Nephrol 10, p. 7–11 (1976).

Edward J. McGuire et al., Pubovaginal Sling Procedure for Stress Incontinence, The Journal of Urology, vol. 119, pp. 82–84 (Jan. 1978).

Jerry Blaivas et al., Pubovaginal Fascial Sling for the Treatment of Complicated Stress Urinary Incontinence, The Journal of Urology, vol. 145, pp. 1214–1218 (Jun. 1991).

Edward J. McGuire, M.D., Abdominal Procedures for Stress Incontinence, Urologic Clinics of North America, pp. 285–290, vol. 12, No. 2 (May 1985).

Jeffrey R. Woodside et al., Suprapubic Endoscopic Vesical Neck Suspension for the Management of Urinary Incontinence in Myelodysplastic Girls, The Journal of Urology, vol. 135, pp. 97–99 (Jan. 1986).

David A. Richardson et al., Delayed Reaction to the Dacron Buttress Used in Urethropexy, The Journal of Reproductive Medicine, pp. 689–692, vol. 29, No. 9 (Sep. 1984).

L. Henriksson et al., A Urodynamic Evaluation of the Effects of Abdominal Urethrocystopexy and Vaginal Sling Urethroplasty in Women with Stress Incontinence, Am. J. Obstet. Gynecol. vol 131, No 1, pp. 77–82 (Mar. 1, 1978).

Robert Zacharin et al., Pulsion Enterocele: Long–Term Results of an Abdominoperineal Technique, Obstetrics & Gynecology, vol. 55 No. 2, pp. 141 148 (Feb. 1980).

Thomas A. Stamey, M.D., Endoscopic Suspension of the Vesical Neck for Urinary Incotinence in Females, Ann. Surg., vol. 192 No. 4, pp. 465–471 (Oct. 1980).

Ulf Ulmsten et al., The Unstable Female Urethra, Am. J. Obstet. Gynecol., vol. 144 No. 1, pp. 93–97 (Sep. 1, 1982).

A. Ingelman–Sunberg et al., Surgical Treatment of Female Urinary Stress Incontinence, Contr. Gynec. Obstet., vol. 10, pp. 51–69 (1983).

Ulf Ulmsten et al., Different Biochemical Composition of Connective Tissue in Continent, Acta Obstet Gynecol Scand, pp. 455–457 (1987).

Bjarne C. Eriksen et al., Long–Term Effectiveness of the Burch Colposuspension in Female Urinary Stress Incontinence, Acta Obstet Gynecol Scand, 69, pp. 45–50 (1990).

H. Enzelsberger et al., Urodynamic and Radiologic Parameters Before and After Loop Surgery for Recurrent Urinary Stress Incontinence, Acta Obstet Gynecol Scand, 69, pp. 51–54 (1990).

Peter E. Papa Petros et al., An Integral Theory of Female Urinary Incontinence, Acta Obstetricia et Gynecologica Scandinavica, vol. 69 Sup. 153, pp. 7–31 (1990).

Peter E. Papa Petros et al., Pinch Test for Diagnosis of Stress Urinary Incontinence, Acta Obstet Gynecol Scand, vol 69, Sup 153, pp. 33–35 (1990).

Peter E. Papa Petros et al., Cough Transmission Ratio: An Indicator of Suburethral Vaginal Wall Tension Rather than Urethral Closure?, Acta Obstet Gynecol Scand, vol 69, Sup 153, pp. 37–39 (1990).

Peter E. Papa Petros et al., The Tuck Procedure: A Simplified Vaginal Repair for Treatment of Female Urinary Incontinence, Acta Obstet Gynecol Scand, vol 69, Sup 153, pp. 41–42 (1990).

Peter E. Papa Petros et al., The Autogenic Ligament Procedure: A Technique for Planned Formation of an Artificial Neo–Ligament, Acta Obstet Gynecol Scand, vol 69, Sup 153, pp. 43–51 (1990).

Peter E. Papa Petros et al., The Combined Intravaginal Sling and Tuck Operation an Ambulatory Procedure for Cure of Stress and Urge Incontinence, Acta Obstet Gynecol Scand, vol 69, Sup 153, pp. 53–59 (1990).

Peter E. Papa Petros et al., Cure of Urge Incontinence by the Combined Intravaginal Sling and Tuck Operation, Acta Obstet Gynecol Scand, vol. 69, Sup 153, pp. 61–62 (1990).

Peter E. Papa Petros et al., The Tethered Vagina Syndrome, Post Surgical Incontinence and I–Plasty Operation for Cure, Acta Obstet Gynecol Scand, vol 69, Sup 153, pp. 63–67 (1990).

Peter E. Papa Petros et al., Non Stress Non Urge Female Urinary Incontinence—Diagnosis and Cure: A Preliminary Report, Acta Obstet Gynecol Scand, vol 69, Sup 153, pp. 69–70 (1990).

Peter E. Papa Petros et al., The Role of a Lax Posterior Vaginal Fornix in the Causation of Stress and Urgency Symptoms: A Preliminary Report, Acta Obstet Gynecol Scand, vol 69, Sup 153, pp. 71–73 (1990).

Peter E. Papa Petros et al., Pregnancy Effects on the Intravaginal Sling Operation, Acta Obstet Gynecol Scand, vol 69, Sup 153, pp. 77–78 (1990).

Peter E. Papa Petros et al., An Analysis of Rapid Pad Testing and the History for the Diagnosis of Stress Incontinence, Acta Obstet Gynecol Scand, vol 71, pp. 529–536 (1992).

Peter E. Papa Petros et al., Bladder Instability in Women: A Premature Activation of the Micturition Reflex, Scandinavian Journal of Neurourology and Urodynamics, Sup 153, pp. 235–239 (1993).

Peter E. Papa Petros et al., Part I: Theoretical, Morphological, Radiographical Correlations and Clinical Perspective, Scandinavian Journal of Neurourology and Urodynamics, Sup 153, pp. 5–28 (1993).

Peter E. Papa Petros et al., Part II: The Biomechanics of Vaginal Tissue and Supporting Ligaments with Special Relevance to the Pathogenesis of Female Urinary Incontinence, Scandinavian Journal of Neurourology and Urodynamics, Sup 153, pp. 29–40 (1993).

Peter E. Papa Petros et al., Part III: Surgical Principles Deriving from the Theory, Scandinavian Journal of Neurourology and Urodynamics, Sup 153, pp. 41–52 (1993).

Peter E. Papa Petros et al., Part IV: Surgical Applications of the Theory—Development of the Intravaginal Sling Plasty (IVS) Procedure, Scandinavian Journal of Neurourology and Urodynamics, Sup 153, pp. 53–54 (1993).

Peter E. Papa Petros et al., An Anatomical Basis for Success and Failure of Female Incontinence Surgery, Scandinavian Journal of Neurourology and Urodynamics, Sup 153, pp. 55–60 (1993).

Peter E. Papa Petros et al., The Development of the Intravaginal Slingplasty Procedure: IVS II—(With Bilateral "Tucks"), Scandinavian Journal of Neurourology and Urodynamics, Sup 153, pp. 61–68 (1993).

Peter E. Papa Petros et al., Further Development of the Intravaginal Slingplasty Procedure—IVS III—(With Midline "Tuck"), Scandinavian Journal of Neurourology and Urodynamics, Sup 153, p. 69–71 (1993).

Peter E. Papa Petros et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, pp. 73–76 (1993).

Peter E. Papa Petros et al., The Further Development of the Intravaginal Slingplasty Procedure—IVS V—(with "Double Breasted" Unattached Vaginal Flam Repair and Permanent Sling)., Scandinavian Journal of Neurourology and Urodynamics, Sup 153, pp. 77–79 (1993).

Peter E. Papa Petros et al., The Intravaginal Slingplasty Procedure: IVS VI—Further Development of the "Double Breasted" Vaginal Flap Repair Attached Flap, Scandinavian Journal of Neurourology and Urodynamics, Sup 153, pp. 81–84 (1993).

Peter E. Papa Petros et al., The Free Graft Procedure for Cure of the Tethered Vagina Syndrome, Scandinavian Journal of Neurourology and Urodynamics, Sup 153, pp. 85–88 (1993).

Peter E. Papa Petros et al., The Posterior Fornix Syndrome: A Multiple Symptom Complex of Pelvic Pain and Abnormal Urinary Symptoms Deriving from Laxity in the Posterior Fornix of Vagina, Scandinavian Journal of Neurourology and Urodynamics, Sup 153, pp. 89–93 (1993).

John DeLancey, MD, Structural Support of the Urethra as it Relates to Stress Urinary Incontinence: The Hammock Hypothesis, Am J Obstet Gynecol, vol 170 No 6, pp. 1713–1723 (Jun. 1994).

Ulf Ulmsten et al., Intravaginal Slingplasty (IVS): An Ambulatory Surgical Procedures for Treatment of Female Urinary Incontinence, Scand J Urol Nephrol, vol 29, pp. 75–82 (1995).

Arieh Bergman et al., Three Surgical Procedures for Genuine Stress Incontinence: Five–Year Follow–Up of a Prospective Randomized Study, Am J Obstet Gynecol, vol 173 No 1, pp. 66–71 (Jul. 1995).

Peter E. Papa Petros et al., Urethral Pressure Increase on Effort Originates from within the Urethra, and Continence from Musculovaginal Closure, Scandinavian Journal of Neurourology and Urodynamics, pp. 337–350 (1995).

U. Ulmsten, Female Urinary Incontinence—A Symptom, Not a Urodynamic Disease. Some Theoretical and Practical Aspects on the Diagnosis a Treatment of Female Urinary Incontinence, International Urogynecology Journal, vol 6, (1 page) (1995).

U. Ulmsten et al., An Ambulatory Surgical Procedure Under Local Anesthesia for Treatment of Female Urinary Incontinence, International Urolgynecology Journal, vol 7, pp. 81–86 (1996).

Peter E. Papa Petros, Development of Generic Models for Ambulatory Vaginal Surgery—Preliminary Report,International Urogynecology Journal, 9 pages (1998).

U. Ulmsten et al., A Multicenter Study of Tension–Free Vaginal Tape (TVT) for Surgical Treatment of Stress Urinary Incontinence, International Urogynecology Journal, vol 9, pp. 210–213 (1998).

Peter E. Papa Petros et al., Medium–Term Follow–Up of the Intravaginal Slingplasty Operation Indicates Minimal Deterioration of Urinary Continence with Time, (3 pages) (1999).

Ulf Ulmsten et al., A Three Year Follow Up of Tension Free Vaginal Tape for Surgical Treatment of Female Stress Urinary Incontinence, British Journal of Obstetrics and Gynaecology, vol 106, pp. 345–350 (1999).

Raymond Rackley, MD., Synthetic Slings: Five Steps for Successful Placement, Urology Times, p. 46, 48, 49 (Jun. 2000).

Peter E. Papa Petros et al., Pelvic Floor Rehabilitation According to the Integrated Theory of Female Urinary Incontinence, Chapter 7, pp. 249–258 (no date).

Peter E. Papa Petros, New Ambulatory Surgical Methods Using an Anatomical Classification of Urinary Dysfunction Improve Stress, Urge and Abnormal Emptying, Int'l. Urogynecology Journal Pelvic Floor Dysfunction, vol. 8 (5), pp. 270–277 (1997).

Stuart Stanton,Springer–Verlag, Surgery of Female Incontinence, pp. 105–113 (1986).

Support™, Sub–Urethral Perineal Retro–Pubic Tensionless Sling, Matrix Medical (Pty) Ltd, (no date), 1 pg.

Raymond R. Rackley, M.D. et al. Tension–free Vaginal Tape and Percutaneous Vaginal Tape Sling Procedures, Techniques in Urology (2001), vol. 7, No. 2, pp. 90–100.

John Klutke, M.D. et al, The promise of tension–free vaginal tape for female SUI, Contemporary Urology, 7 pages (Oct. 2000).

TVT Tension–free Vaginal Tape, Gynecare, Ethicon, Inc., 23 pages (1999).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Peter E. Papa Petros et al., Cure of Stress Incontinence by Repair of External Anal Sphincter, Acta Obstet Gynecol Scand, vol 69, Sup 153, p. 75 (1990).

Peter Petros et al., Anchoring the Midurethra Restores Bladder–Neck Anatomy and Continence, The Lancet, vol 354, pp. 997–998 (Sep. 18, 1999).

Ross Decter, Use of the Fascial Sling for Neurogenic Incontinence Lessons Learned, The Journal of Urology, vol. 150 pp. 683–686 (Aug. 1993).

Julia Spencer et al., A Comparison of Endoscopic Suspension of the Vesical Neck with Suprapubic Vesicourethropexy for Treatment of Stress Urinary Incontinence, The Journal of Urology, vol. 137, pp. 411–415 (Mar. 1987).

Tohru Araki et al., The Loop–Loosening Procedure for Urination Difficulties After Stamey Suspension of the Vesical Neck, The Journal of Urology, vol. 144, pp. 319–323 (Aug. 1990).

George Webster et al., Voiding Dysfunction Following Cystourethropexy: Its Evaluation and Management, The Journal of Urology, vol. 144, pp. 670–673 (Sep. 1990).

Albert H. Aldridge, B.S., M.D., F.A.C.S., Transplantation of Fascia for Relief of Urinary Stress Incontinence, American Journal of Obstetrics and Gynecology, V. 44, pp. 398–411, (1948).

Victor Fray Marshall et al. The Correction of Stress Incontinence by Simple Vesicourethral Suspension, Surgery, Gynecology and Obstetrics, vol. 88, pp. 509–518 (1949).

Henry Roberts, M.D., Cystourethrography in Women, Deptment of Obstetrics and Gynaecology, University of Liverpool, May 1952, vol. XXXV, No. 293, pp. 253–259.

T.N.A. Jeffcoate, The Results of the Aldridge Sling Operation for Stress Incontinence, Journal of Obstetrics and Gynaecology, pp. 36–39 (1956).

W.E. Studiford: Transplantation of Abdominal Fascia for the Relief of Urinary Stress Incontinence, American Journal of Obstetrics and Gynecology, pp. 764–775 (1944).

W.R. Sloan et al., Stress Incontinence of Urine: A Retrospective Study of the Complications and Late Results of Simple Suprapubic Suburethral Fascial Slings, The Journal of Urology, vol. 110, pp. 533–536 (Nov. 1973).

G. Narik et. al., A Simplified Sling Operation Suitable for Routine Use, Gynecological and Obstetrical Clinic, University of Vienna, vol. 84, No 3, p. 400–405, (Aug. 1, 1962).

Jerry Blaivas et al., Type III Urinary Incontinence: Importance of Proper Diagnosis and Treatment, Surgical Forum, pp. 473–475, (1984).

* cited by examiner

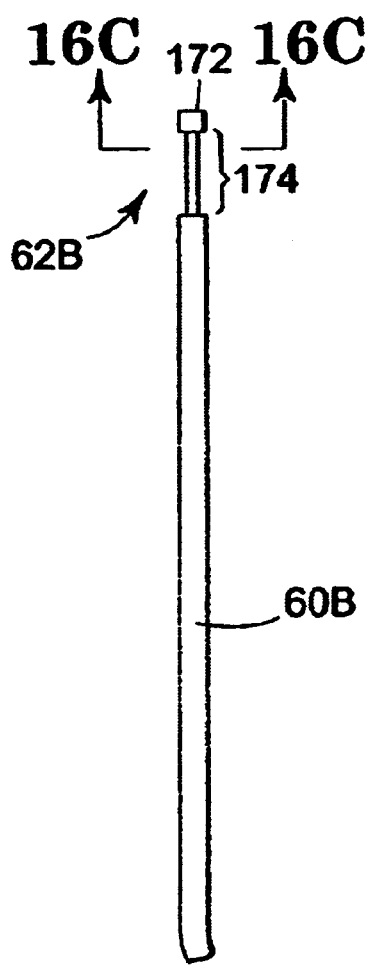
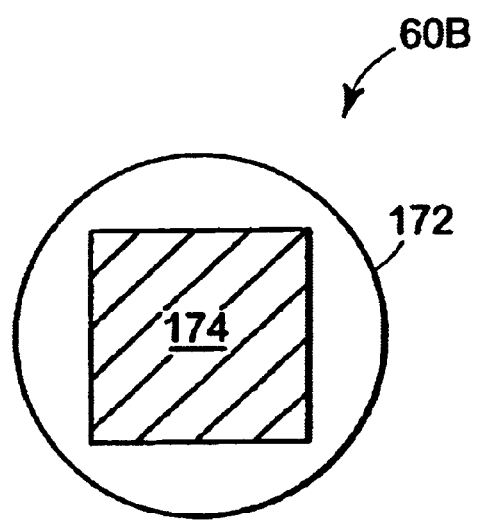
Fig. 16C
Fig. 16B

IMPLANTABLE ARTICLE AND METHOD FOR TREATING URINARY INCONTINENCE USING MEANS FOR REPOSITIONING THE IMPLANTABLE ARTICLE

CROSS REFERENCE TO RELATED APPLICATIONS

The present application claims priority of U.S. Provisional Application Serial No. 60/263,472, filed Jan. 23, 2001; and U.S. Provisional Application Serial No. 60/269, 829, filed Feb. 20, 2001; and U.S. Provisional Application Serial No. 60/281,350, filed Apr. 4, 2001; and U.S. Provisional Application Serial No. 60/295,068, filed Jun. 1, 2001; and U.S. Provisional Application No. 60/306,915, filed Jul. 20, 2001, each of whose contents are fully incorporated herein by reference.

BACKGROUND

Over 13 million American men and women of all ages suffer from urinary incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. FIG. 2 schematically illustrates female anatomy. The urethra 16 is the tube that passes urine from the bladder 14 out of the body. The narrow, internal opening of the urethra 16 within the bladder 14 is the bladder neck 18. In this region, the bladder's bundled muscular fibers transition into a sphincteric striated muscle called the internal sphincter. FIG. 3 schematically illustrates male anatomy. The urethra 16 extends from the bladder neck 18 to the end of the penis 22. The male urethra 16 is composed of three portions: the prostatic, bulbar and pendulus portions. The prostatic portion is the widest part of the tube, which passes through the prostate gland 24.

Incontinence may occur when the muscles of the urinary system malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder" "frequency/urgency syndrome" or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611, 515; 5,842,478; 5,860,425; 5,899,909; 6,039,686, 6,042,534 and 6,110,101.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The TVT Tension-free Vaginal Tape procedure utilizes a Prolene™ nonabsorbable, polypropylene mesh. The mesh is a substantially flat, rectangular knitted article. The mesh includes a plurality of holes that are sized to allow tissue ingrowth to help avoid infection. A plastic sheath surrounds the mesh and is used to insert the mesh. During the sling procedure, incisions are made in the abdominal (i.e. suprapubic) area and in the vaginal wall. Two curved, needle-like elements are each connected to an end of the vaginal sling mesh. A sling-free end of one of the needle-like elements is initially pushed through the vaginal incision and into the paraurethral space. Using a handle attached to the needle, the needle is angulated laterally (for example, to the right) to perforate the endopelvic fascia, guided through the retropubic space and passed through the abdominal incision. The handle is disconnected and the needle is then withdrawn through the abdominal wall, thereby threading a portion of the sling through the tissue of the patient. The handle is then connected to the other needle and the technique is repeated on the contralateral side, so that the mesh is looped beneath the bladder neck or urethra. The sling is positioned to provide appropriate support to the bladder neck or urethra. Typically a Mayo scissors or blunt clamp is placed between the urethra and the sling to ensure ample looseness of the sling. When the TVT mesh is properly positioned, the cross section of the mesh should be substantially flat. In this condition, the edges of the mesh do not significantly damage tissue. The sling ends are then cut at the abdominal wall, the sheath is removed and all incisions are closed.

Complications associated with the TVT procedure and other known sling procedures include injury to blood vessels of the pelvic sidewall and abdominal wall, hematomas, urinary retention, and bladder and bowel injury due to passage of large needles. Further, a separate cystoscopy procedure is usually required in order to confirm bladder integrity or recognize a bladder perforation after each insertion of the needle-like element. One serious disadvantage of the TVT procedure, particularly for surgeons unfamiliar with the surgical method, is the lack of information concerning the precise location of the needle tip relative to adjacent pelvic anatomy. If the needle tip is allowed to accidentally pass across the surface of any blood vessel, lymphatic duct, nerve, nerve bundle or organ, serious complications can arise. These shortcomings, attempts to address these shortcomings and other problems associated with the TVT procedure are disclosed in PCT publication nos. PCT WO 00/74613 and PCT WO 00/74594.

Additional problems are associated with the TVT and other sling procedures. Due to the tough fibrous nature of fascia and muscle tissues, forceps or similar instruments are needed to withdraw the needles through the abdominal wall. However, the smooth surface of the needles, which facilitates insertion through the tissues, prevents secure attachment of the forceps onto the needles, causing slippage or detachment of the forceps during the withdrawal procedure. Removal and reuse of the handle of the TVT product is also a cumbersome, time consuming process, requiring the surgeon to manually rotate the handle until the handle is unscrewed from the needle. Reusing the handle presents a contamination risk, particularly if the handle and screw threads are not properly cleaned and sterilized after use on one side of the patient.

The problems associated with improper placement of the TVT mesh are particularly troublesome. If the mesh is too loosely associated with its intended physiological environment, the mesh may be ineffective in supporting the urethra and treating incontinence. Several complications can arise from a mesh that is too tightly placed including retention, sling erosion and other damage to surrounding tissue such as the urethra and vagina.

Once the sheath is removed from the mesh of the TVT product, friction between the mesh and tissue keeps the mesh in position and it becomes very difficult to subsequently adjust the position of the mesh relative to tissue. Because the tension of the sling is an important part of the sling procedure, surgeons will nonetheless attempt to adjust the tension of a sling even after the sheath is removed. TVT mesh is elongate, substantially flat and elastic. When pulled on longitudinally, the TVT mesh deflects elastically. If insufficient adjustment force is applied, the sling will simply exhibit a memory property and return to its original, unacceptable position. As a result, surgeons are tempted to use a great deal of force in order to loosen a sling that is perceived to be too tightly associated with its intended physiological environment. If excessive force is applied, the mesh will plastically deform and the cross section of the mesh will become arcuate. Under excessive deformation, the holes of the TVT mesh become significantly smaller, and risk deterring tissue ingrowth. Without tissue ingrowth, the potential for infection is believed to increase. In the excessively deformed state, the edges of the mesh tend to curl up and present a relatively sharp, frayed surface. In this curled or deformed state, the edges of the TVT mesh present sharp surfaces that can readily abrade or otherwise damage adjacent tissue such as the urethra, bladder or vagina.

Attempts to reposition the TVT sling is likely to fail in two modes. First, the surgeon may apply insufficient elongation force to the mesh (e.g. with forceps), resulting in temporary elastic deformation of the mesh followed by a return by the mesh to its original, unacceptable position after the force is removed. Second, the surgeon may apply excessive force to the mesh resulting in the curling deformation described above with the attendant risk of tissue damage.

Additionally, an axially deformed sling necks down (i.e. decreases in width) and provides less cross sectional area to support the urethra. Thus, even if the edges do not curl, excessive deformation of the TVT sling risks adversely affecting sling performance. In the case of an improperly positioned sling, some surgeons will cut the TVT mesh and attempt to remove the mesh as reported in the literature.

There is a desire to obtain a minimally invasive yet highly effective device that can be used with minimal to no side effects. Such a device should reduce the complexity of a sling procedure, be biocompatible, adjustable, and non-toxic. The treatment methods using the device should reduce pain, operative risks, infections and post operative hospital stays. Further, the method of treatment should also improve the quality of life for patients.

BRIEF SUMMARY

The present invention comprises an implantable article suitable for treating urological disorders in patients. In one aspect, the present invention comprises a sling for treating urinary incontinence in a patient. The sling has first and second major surfaces, a pair of end portions, and a support portion for placement in a therapeutically effective position relative to a physiological environment intended to be supported. The support portion preferably has an axially elongate mesh, and a pair of ends. The present invention includes repositioning means, associated with the sling, for transferring either sling tightening or sling loosening forces along the sling to afford effective, permanent repositioning of the sling without adversely affecting the therapeutic effect of the sling. The repositioning means transfers sling tightening or sling loosening forces along the sling while avoiding permanent deformation of the sling. Preferably, the repositioning means is constructed to afford transfer at least some of a repositioning force applied to the sling to an end of the support portion.

Preferably the sling is sized and shaped for treating female incontinence with a surgical procedure that includes a vaginal incision, and the repositioning means is free of any structure that extends through the vaginal incision. Preferably, the sling includes a removable sheath and the repositioning means affords permanent tightening of the sling when the sling is partially implanted and the sheath is removed, by pulling on the sling and repositioning means at a suprapubic location.

The sling is preferably initially placed via an access incision such as a vaginal incision, and the repositioning means affords post operative loosening of the sling after the vaginal incision is closed without any subsequent vaginal incision and without any structure extending through the original vaginal incision.

The repositioning means preferably comprises at least one, unitary, non-separated filament threaded along the mesh and is attached to the mesh at the ends of the support portion. Alternatively, the repositioning means may comprise at least one filament integrally woven in the mesh, or it can comprise a plurality of filaments that are each threaded along substantially the entire length of the mesh. See FIG. 1B which illustrates three filaments 66b that are threaded along the entire length of the mesh. The filament may optionally extend from an edge of the support portion to another edge of the support portion.

The mesh may be woven, braided or knitted or other structures. It may be constructed from synthetic or non-synthetic materials, bioresorbable, permanent or non-permanent materials. In a preferred embodiment, when the mesh of the support portion is woven, the repositioning means comprises a portion of the support portion that is more tightly woven than another portion of the support portion.

Preferably, instead of a separate elongate member, the repositioning means may comprises a portion of the mesh that is more tightly woven than another portion of the sling.

In a preferred embodiment, the repositioning member is woven in a weave pattern along the mesh so that the weave pattern affords an indication of proper sling orientation after implantation. For example, a majority of the repositioning member may protrude above the second major side of the support portion of the sling.

Optionally, a sheath may be included in the assembly. The sheath can include sheath indicia means for assisting the surgeon in properly orienting the sling relative to the urethra or separation means selected from the group consisting of tear scores, perforations or holes. Preferably, the sheath comprises first and second sections that overlap adjacent the support portion of the sling.

In a preferred embodiment, the repositioning means comprises a one piece, elongate member threaded in the mesh and extending axially along substantially the entire length of the sling, and wherein the one piece, elongate member is attached to the sling at the ends of the support portion. Optionally, the sling may include a means for locating and detaching the one piece, elongate member, such as loops in the elongate, one piece member at the ends of the support portion.

Other optional features may be provided for the article of the present invention. For example, the repositioning means may include a handle situated in the support portion.

In another aspect, the present invention comprises a method of treating urinary incontinence in a patient comprising the steps of establishing a pathway in tissue on both sides of a patient's tissue intended to be supported, the pathways extending between an abdominal wall of the patient and a pubic space of the patient; atraumatically dilating the pathways after the establishment of the pathways; introducing a sling material into the pathways while the pathways are being atraumatically dilated; positioning the sling material in the pathways in a therapeutic relationship relative to the tissue of the patient that is intended to be supported (e.g. the urethra), and so that the sling extends upward toward the abdominal wall; and repositioning the sling to support the urethra of the patient.

The method affords both tightening and loosening of the sling during the surgical procedure. Preferably, the step of establishing a pathway comprises making an original vaginal incision and the step of repositioning the sling occurs after the vaginal incision is closed and is accomplished without any structure passing through the original vaginal incision. The step of repositioning the sling may occur post or perioperatively.

BRIEF DESCRIPTION OF THE DRAWINGS

Other features and advantages of the present invention will be seen as the following description of particular embodiments progresses in conjunction with the drawings, in which:

FIG. 16B is a side view of a portion of an embodiment of needle according to the present invention;

FIG. 16C is a sectional view of a needle according to the present invention; taken approximately along the lines of 16C—16C in FIG. 16B;

FIGS. 18A—18E illustrate one embodiment of the handle of the present invention, wherein:

FIG. 18A is a perspective view of the handle;

FIG. 18B is a sectional view of the handle, showing elements in a disassembled condition;

FIG. 18C is a sectional view of the handle of FIG. 18A;

FIG. 18D is a sectional view of the handle of FIG. 18A showing elements in a locked position;

FIG. 18E is a perspective view of the handle of FIG. 18A showing elements in an unlocked position;

FIGS. 29A through 29D are perspective views sequentially showing the insertion of a needle suprapubically according to one aspect of the present invention, wherein:

FIG. 29A shows the needle just passing an abdominal incision;

FIG. 29B illustrates the needle as the surgeon seeks to identify the tactile feel of the resistance provided in part by the posterior portion of the pubic bone;

FIG. 29C shows the needle as it passes along the posterior surface of the pubic bone which may be used as an anatomical guide for a surgeon as the needle approaches a vaginal incision;

FIG. 29D illustrates the needle as it passes out of a vaginal incision;

DETAILED DESCRIPTION

The following description is meant to be illustrative only and not limiting. Other embodiments of this invention will be apparent to those of ordinary skill in the art in view of this description.

Figure 4:
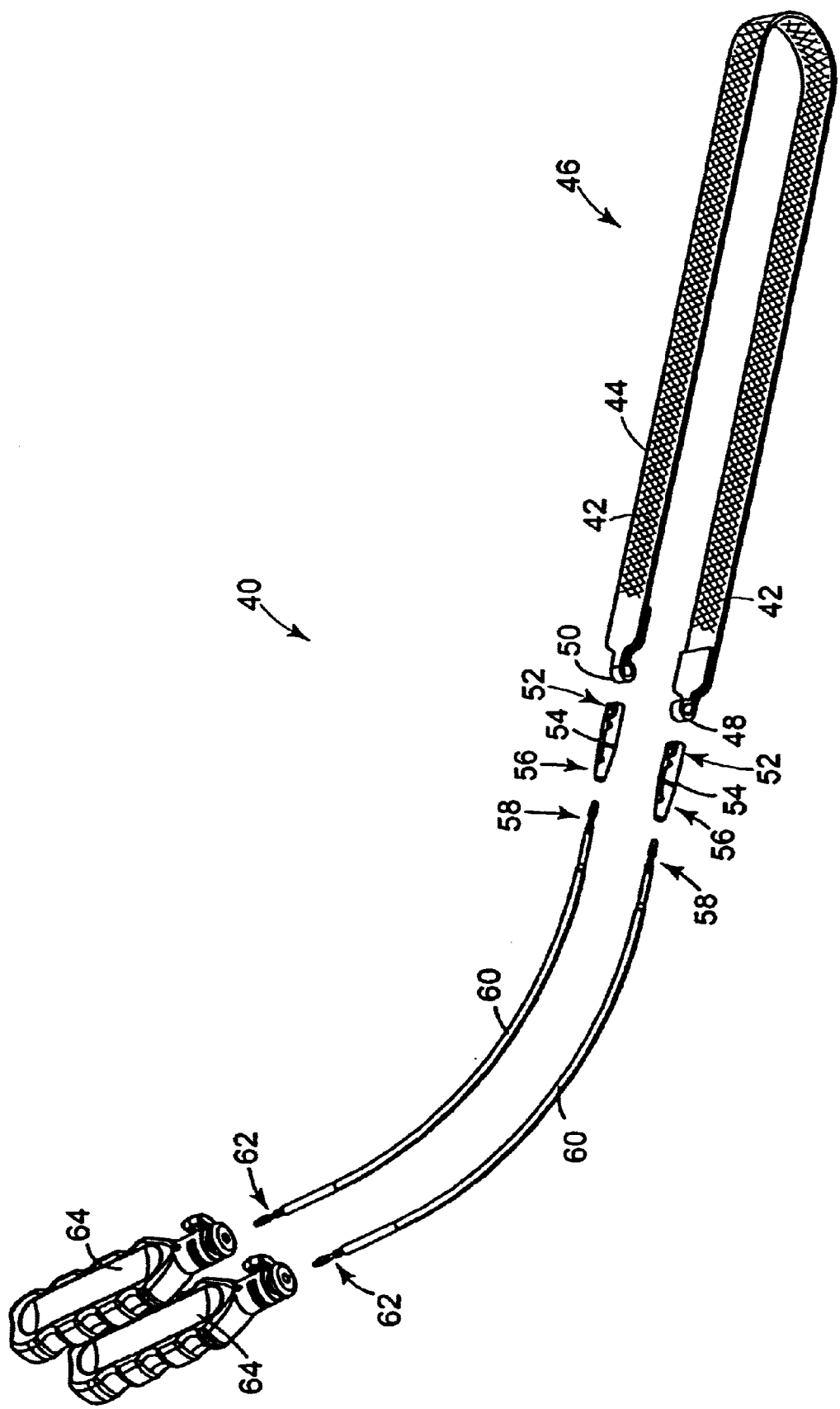
FIG. 4 is a perspective view of one embodiment of the sling delivery system of the present invention, showing the sling delivery system disassembled.

Referring to FIG. 4, an embodiment of assembly 40 in accordance with the present invention includes a sling assembly 46 that includes a sling 42 for treating incontinence. The present invention is particularly suitable for treating stress urinary incontinence (SUI) diagnosed with urethral hypermobility or intrinsic sphincter deficiency in both men and women. Although the invention as disclosed herein generally refers to SUI, treatment of other urological disorders, such as urge incontinence, mixed incontinence, overflow incontinence, functional incontinence, prolapse (e.g. vaginal), enteroceles (e.g. of the uterus), rectoceles and other non-urological disorders, are also included within the scope of the present invention. It is contemplated that the present invention may also be utilized in conjunction with other procedures, such as, but not limited to, procedures for addressing cystocele prolapse, vaginal prolapse and anatomic hypermobility.

The sling assembly 46 preferably includes an implantable member (e.g. a hammock, sling or strip) 42 within a protective sheath 44. The sheath 44 is used during insertion of the strip 42. After the sling 42 is implanted, the sheath 44 is removed and discarded.

Each of the two ends 48, 50 of the elongate sling assembly 46 attaches to a first end 52 of a dilator 54 or needle-sling connector. The dilator 54 dilates a needle track for ease of sling introduction and positioning within the patient. A second end 56 of each dilator 54 is sized and shaped to quickly and securely connect to a first end 58 of a slim, arc-shaped needle 60. An adjustable handle 64 is preferably removably and repositionably attached to a second end 62 of the needle 60. Each end 58, 62 of the needle 60 is preferably keyed to allow for convenient, secure attachment of the needle 60 relative to the handle 64 and dilator 54. In a preferred embodiment, the key feature prevents rotation of the dilator 54 relative to the needle 60. Alternatively, the handle 64 may be rigidly affixed to the needle 60.

Figure 1:
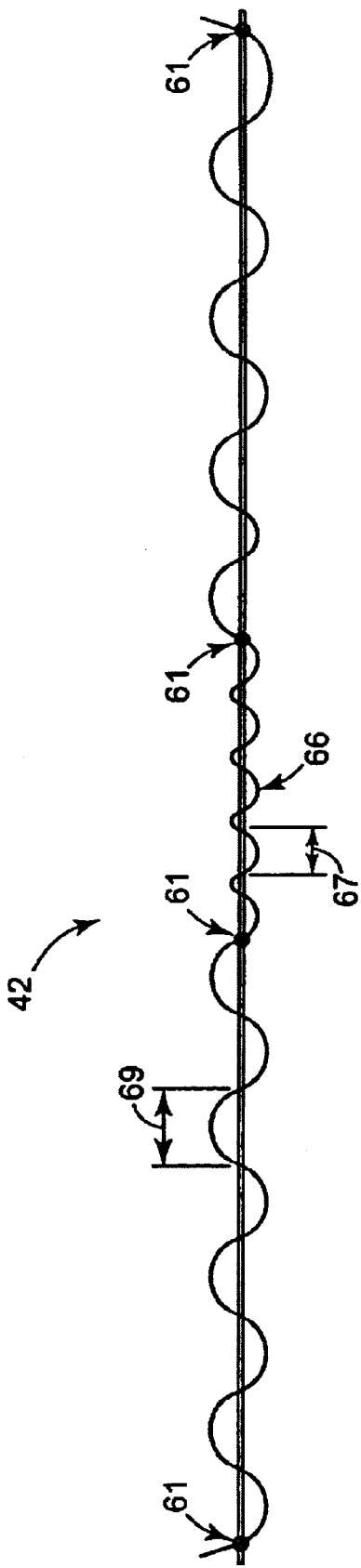
FIG. 1 is a side view of a sling according to one aspect of the present invention.
Figure 1A:
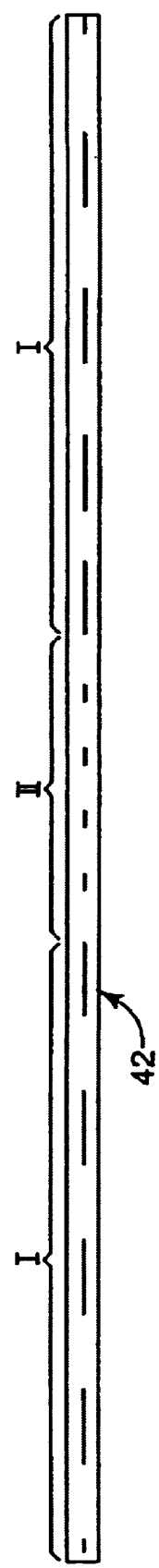
FIG. 1A is a top view of a sling according to another aspect of the present invention.
Figure 1B:
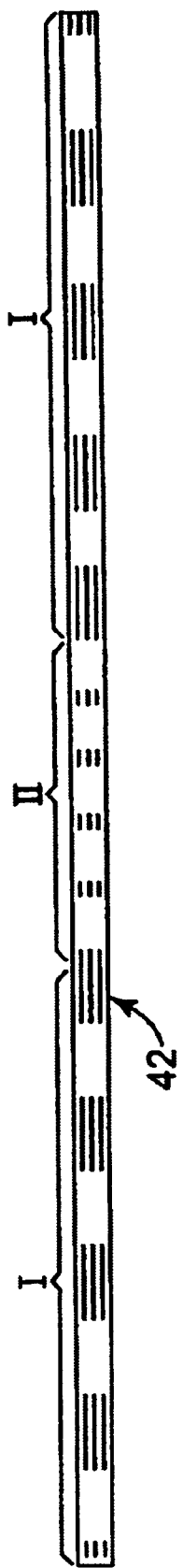
FIG. 1B is a top view of a sling according to another aspect of the present invention.
Figure 2:
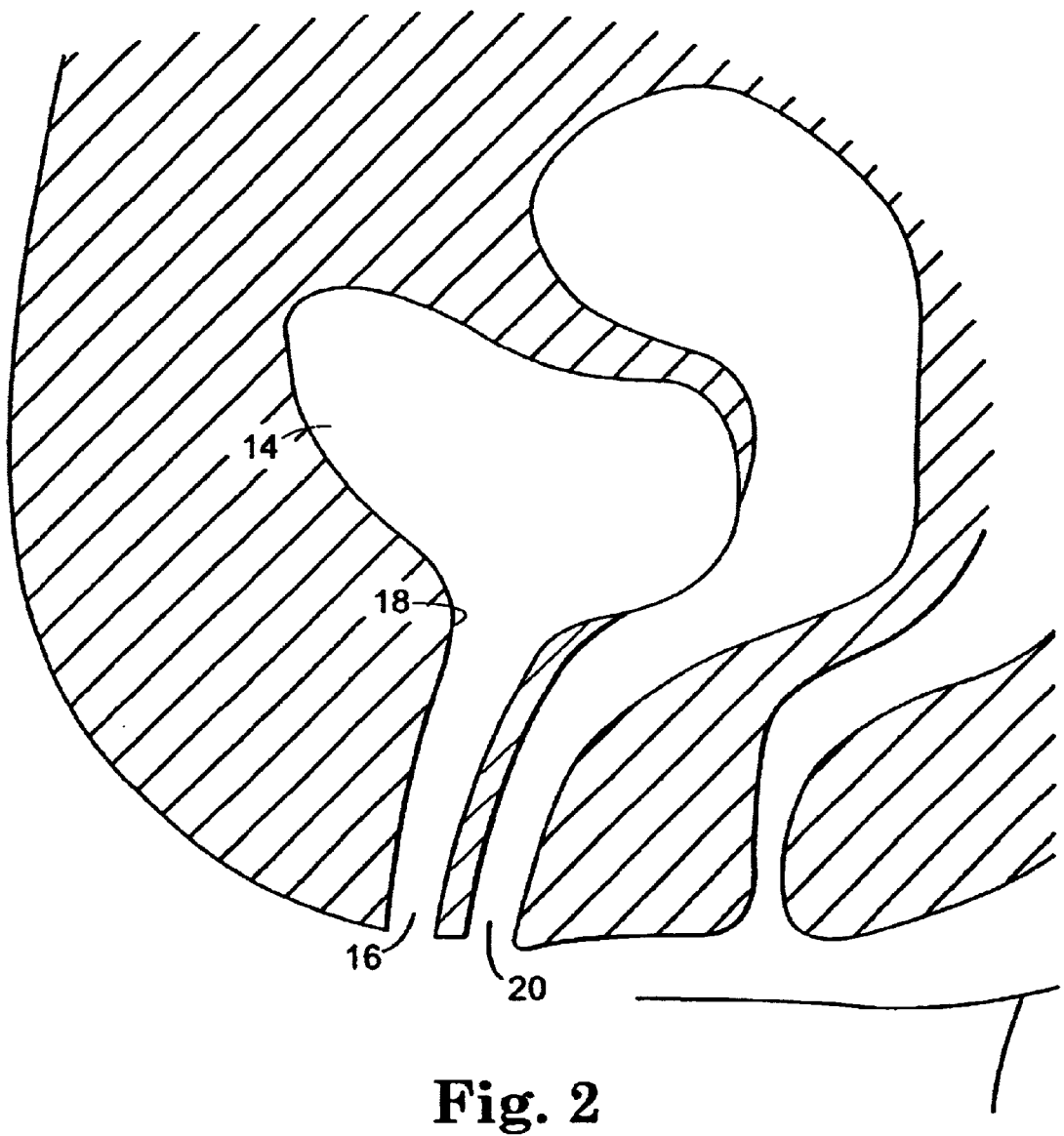
FIG. 2 is a schematic view of the female urinary system.
Figure 3:
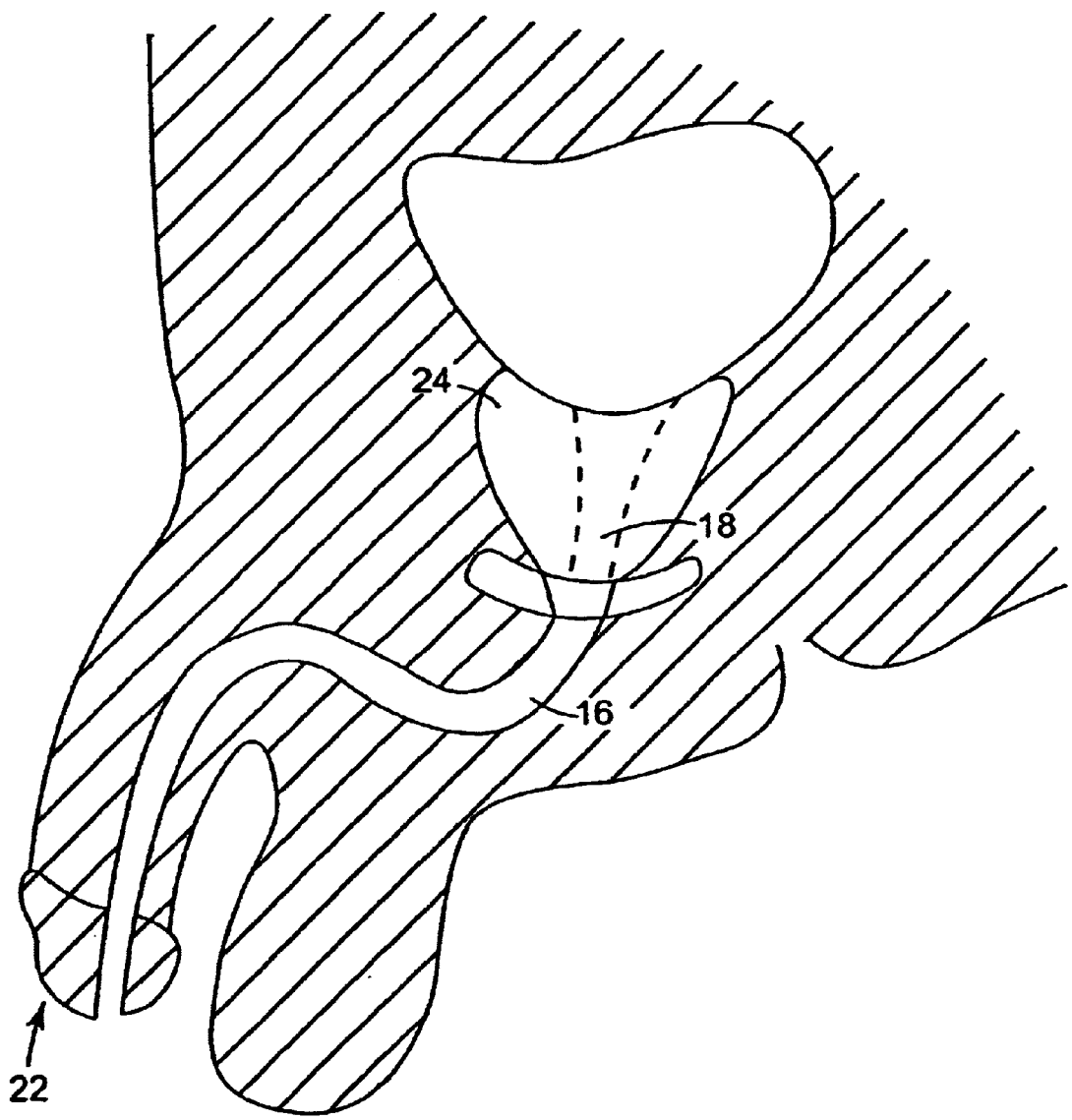
FIG. 3 is a schematic view of the male urinary system.

Referring to FIGS. 1 and 1A, the sling 42 preferably comprises first and second major surfaces, a pair of end portions I, and a support portion II for placement in a therapeutically effective position relative to a physiological environment intended to be supported (e.g. near the urethra). In one aspect of the present invention, the sling 42 preferably has a tension adjustment or control member 66 associated with the sling 42, for transferring sling adjustment forces from one portion of the sling 42 to other portions of the sling 42 such as the ends 61 of a support portion II of the sling (see FIGS. 1 and 1A). The member 66 affords effective repositioning of the sling 42 while avoiding undesirable permanent deformation of the sling 42. In the embodiment of the present invention depicted in FIGS. 1 and 1A, the tension adjustment member is a filamentary member. The tension adjustment member 66 is preferably threaded along the length of sling 42. More preferably, the tension adjustment member 66 is connected at some points. For example, if the sling 42 comprises a synthetic mesh material, then the filament may be affixed at the junctures 61 between the support portion II and the end portions I.

Figure 5:
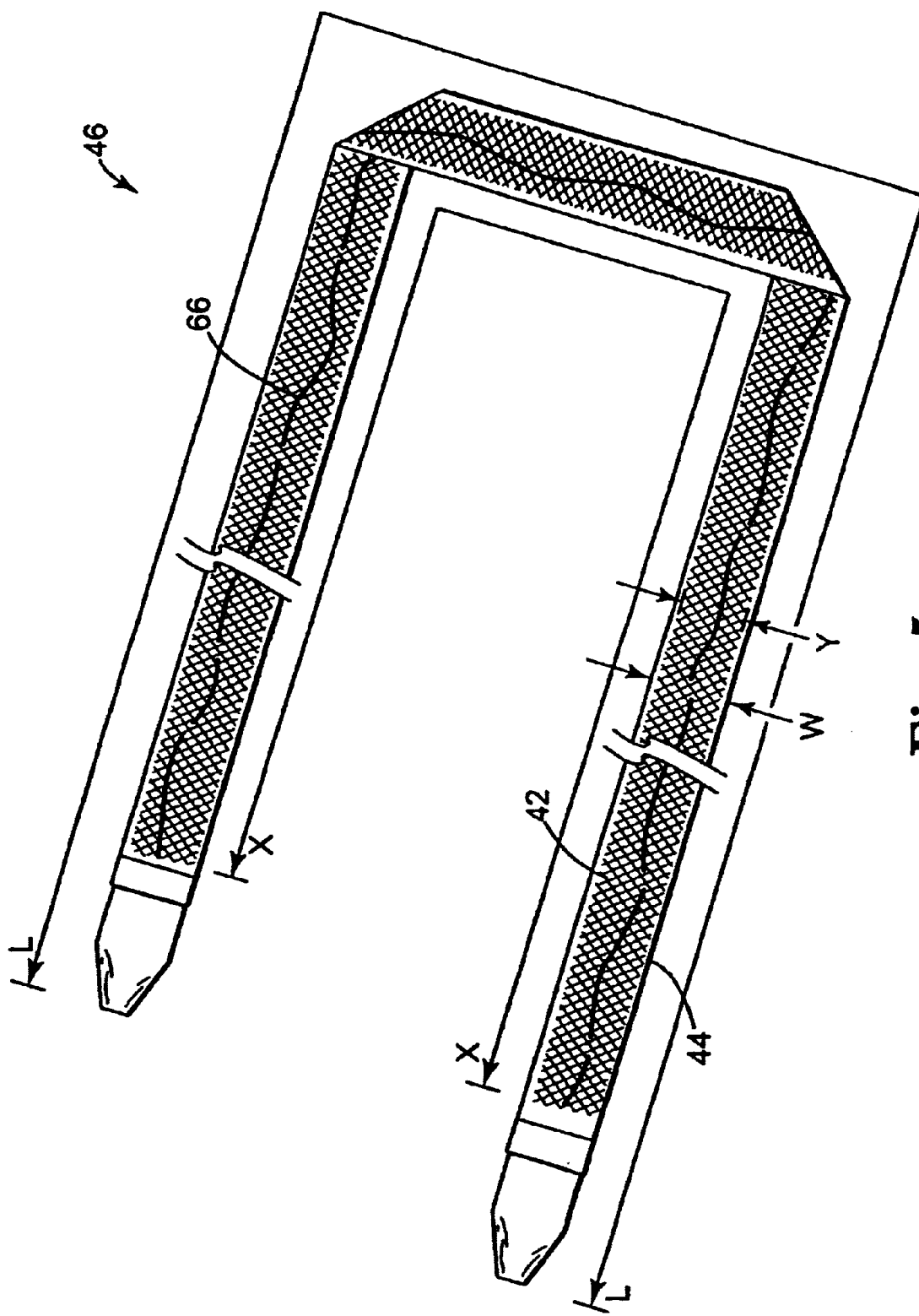
FIG. 5 is a perspective view of one embodiment of a sling assembly of the present invention.

The sling 42 is preferably at least substantially surrounded by the protective sheath 44, as shown in FIGS. 4 and 5. The sling 42, tension control element 66 and sheath 44 are made of biocompatible materials having sufficient strength and structural integrity to withstand the various forces exerted upon these components during an implant procedure and/or following implantation within a patient. Preferably, the protective sheath 44 is constructed of a material that affords visual examination of the implantable sling material 42 and that affords convenient passage of the assembly 46 through tissue of the patient.

Preferably, the overall dimensions of the sling assembly 46, including individual sheath 44, sling 42 and tension control member 66, are sufficient to extend from an abdominal incision, to an undersurface of the urethra and back to another abdominal incision with additional size to account for the imprecision associated with the range of human anatomy sizes. In a preferred embodiment, the sheath length L of the device 40 of the present invention is approximately within the range of 52.0 cm to 58.5 cm (20.5 inches to 23.0 inches), sheath width W is approximately within the range of 1.0 cm to 1.63 cm (0.482 inch to 0.642 inch) and sheath material thickness is approximately within the range of 0.127 mm to 0.203 mm (0.005 inch to 0.008 inch), respectively. The associated sling 42 has a length X, width Y and thickness approximately within the range of 49 cm to 51 cm (19.3 inches to 20.1 inches), 1.0 cm to 1.2 cm (0.394 inch to 0.472 inch) and 0.508 mm to 0.711 mm (0.020 inch to 0.028 inch), respectively. In addition, the length of the tension control element 66 should be approximately equivalent to or slightly longer than the length of the sling 42 to tighten or loosen the sling 42 after it is placed in the body. Alternative lengths, widths and thicknesses can also be used.

Figure 41:
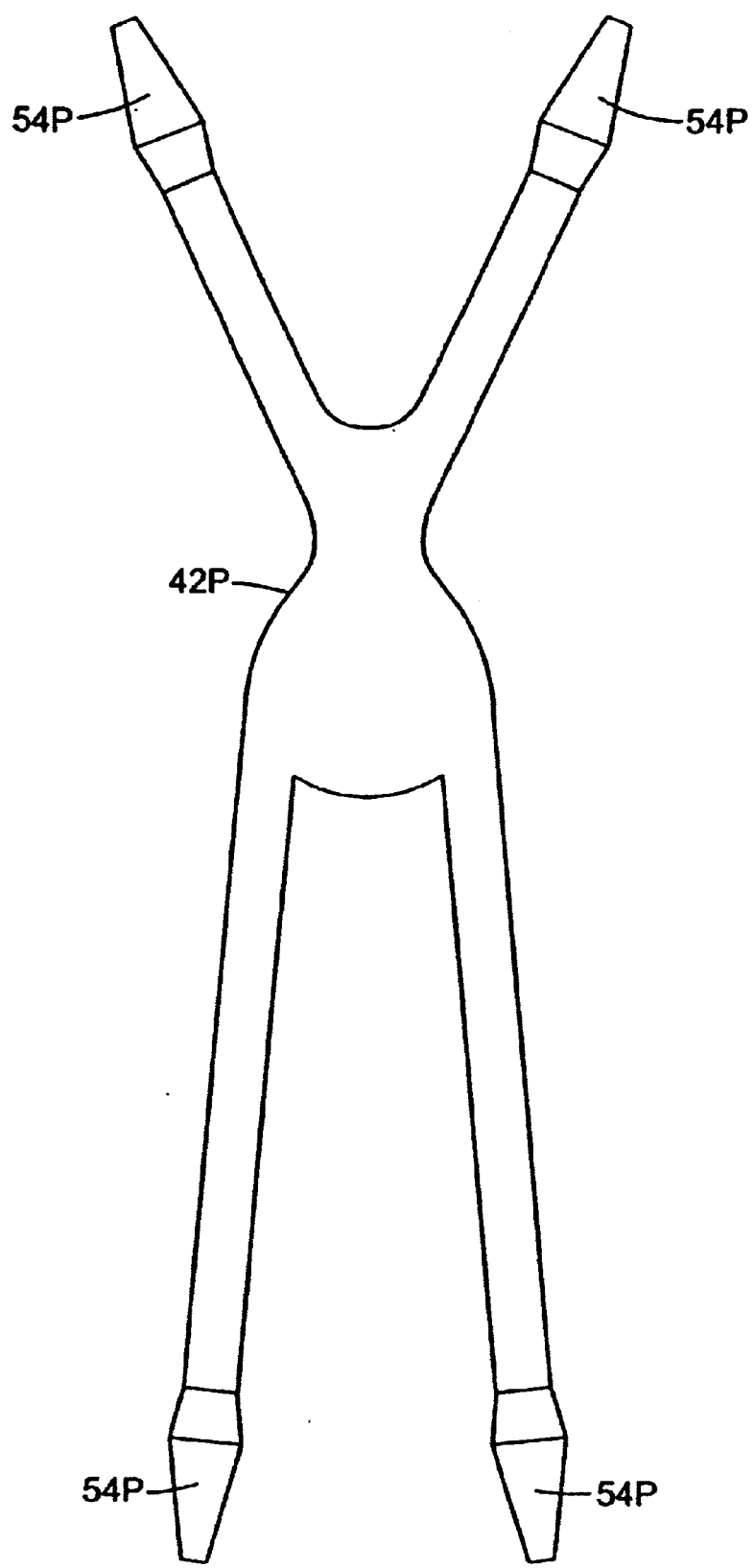
FIG. 41 is a top view of an alternative sling embodiment according to the present invention.

As used herein, the term "sling" is used generally to include a wide variety of shapes and sizes, materials and treatments. While the sling 42 is preferably rectangular for treating SUI in females, other shapes are also contemplated. Depending on the treatment addressed (e.g. to provide hammock support for the bladder or bladder neck, or to address a rectocele, enterocele or prolapse) the sling may be any of a wide variety of shapes. As an example, the sling may be of the general shape of the slings described and shown in Moir et al., *The Gauze-Hammock Operation*, Journal of Obstetrics and Gynaecology of the British Commonwealth, Volume 75, No. 1, Pps. 1–9 (1968). FIG. 41 illustrates another example of a shape of a sling 42G according to the present invention. This sling shape is believed to be useful for providing a hammock support for an anatomical structure such as the bladder or the juncture between the bladder and bladder neck.

In one embodiment, the sling 42 is made of a mesh material. The mesh material comprises one or more woven or inter-linked filaments or fibers that form multiple fiber junctions throughout the mesh. The fiber junctions may be formed via weaving, bonding, ultrasonic welding or other junction forming techniques, including combinations thereof. In addition, the size of the resultant openings or pores of the mesh should be sufficient to allow tissue in-growth and fixation within surrounding tissue. As an example, not intended to be limiting, the holes may comprise polygonal shaped holes with diagonals of 0.132 inches and 0.076 inches. The quantity and type of fiber junctions, fiber weave, pattern, and material type influence various sling properties or characteristics. Non-mesh sling configurations are also included within the scope of the invention. As another example, not intended to be limiting, the mesh may be woven polypropylene monofilament, knitted with a warp tricot. The stitch count may be 27.5 courses/inch (+ or −2 courses ) and 13 wales/inch (+ or −2 wales). The thickness of this example is 0.024 inches.

In a preferred embodiment, the mesh material of the sling 42 comprises a flexible, polypropylene monofilament that resists weakening or degradation when implanted within a patient. One such material is Marlex™ material. Other mesh and non-mesh materials including, but not limited to, synthetic biomaterials, allografts, homografts, heterografts, autologous tissues, materials disclosed in U.S. Provisional Applications Ser. Nos. 60/263,472, 60/281,350 and 60/295,068, whose contents are fully incorporated herein by reference, synthetic materials (such as metallics, polymerics, and plastics) and any combination of such materials may also be used with the device of the present invention. Specific examples of synthetic sling materials include, but are not limited to polypropylene, polyethylene, nylon, PLLA and PGA. Preferably, the sling material should cause minimal to no reaction with body tissues and fluids and indefinitely retain its particular material characteristics/properties. Further, portions or all of the sling 42 may be configured or fabricated from a material to either promote or prevent tissue in-growth, or are resorbable to accomplish the desired purpose.

In another embodiment of the invention, the sling 42, sling assembly 46 or portions thereof, may have one or more substances associated therewith through a process such coating. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, enhance visualization, indicate proper sling orientation, resist infection or other effects. For example, a dye may be coated on one surface of the sling 42. The dye provides the practitioner/surgeon with a visual indicator to aid in properly orienting the sling 42 at the target site within the patient and to avoid undesirable twists along the length of the sling 42. As another example, the sling may be coated by the process described in U.S. Pat. Nos. 5,624,704; 5,756,145; 5,853,745; 5,902,283 and 6,162,487 (the entire contents of which are hereby incorporated by reference).

The sling 42 of the present invention need not have additional sutures or other anchoring devices. Upon implantation, a portion of the sling 42 is passed and/or woven through various layers of abdominal/pelvic tissue. The frictional forces created between the sling 42 and patient tissue prevents movement and loss of tension once the sling 42 is properly located at the target site within the lower abdominal area of the patient. As a result, the sling 42 remains securely in place, even when subjected to various increased abdominal pressures.

The sling 42 is designed to remain within the body of a patient as an implant for a predetermined therapeutically effective amount of time. The sling may be non-absorbable, absorbable or resorbable, including any combinations of these material properties, depending on the desired treatment. For example, portions of the sling 42 or sling assembly 46 may be constructed of a bioabsorbable material designed to last for a predetermined period of time within the patient, that should be sufficiently long to afford treatment of the patient's need. The general characteristics of the sling material and design should be such as to withstand the various forces exerted upon it during implantation (for example, frictional forces associated with tissue resistance) and after implantation (for example, increased abdominal or bladder pressure caused by coughing, laughing, sneezing, or lifting). Preferably, the sling 42 is configured to exploit the healing process and provides adequate support to correct incontinence.

The sling assembly 46 preferably has a feature that assists the surgeon in placing the sling 42 in a therapeutically effective anatomical position. The precise, final location of the sling 42 will depend on a variety of factors including the particular surgical procedure(s) performed, and any preconditions of the patient such as scar tissue or previous surgeries. For example, it may be preferred to place the sling 42 in close proximity to, but not in contact with, a mid portion of the urethra 16 to treat incontinence. In a male patient, the sling 42 may be placed proximate, but not in contact with the bulbar urethra.

Figure 7:
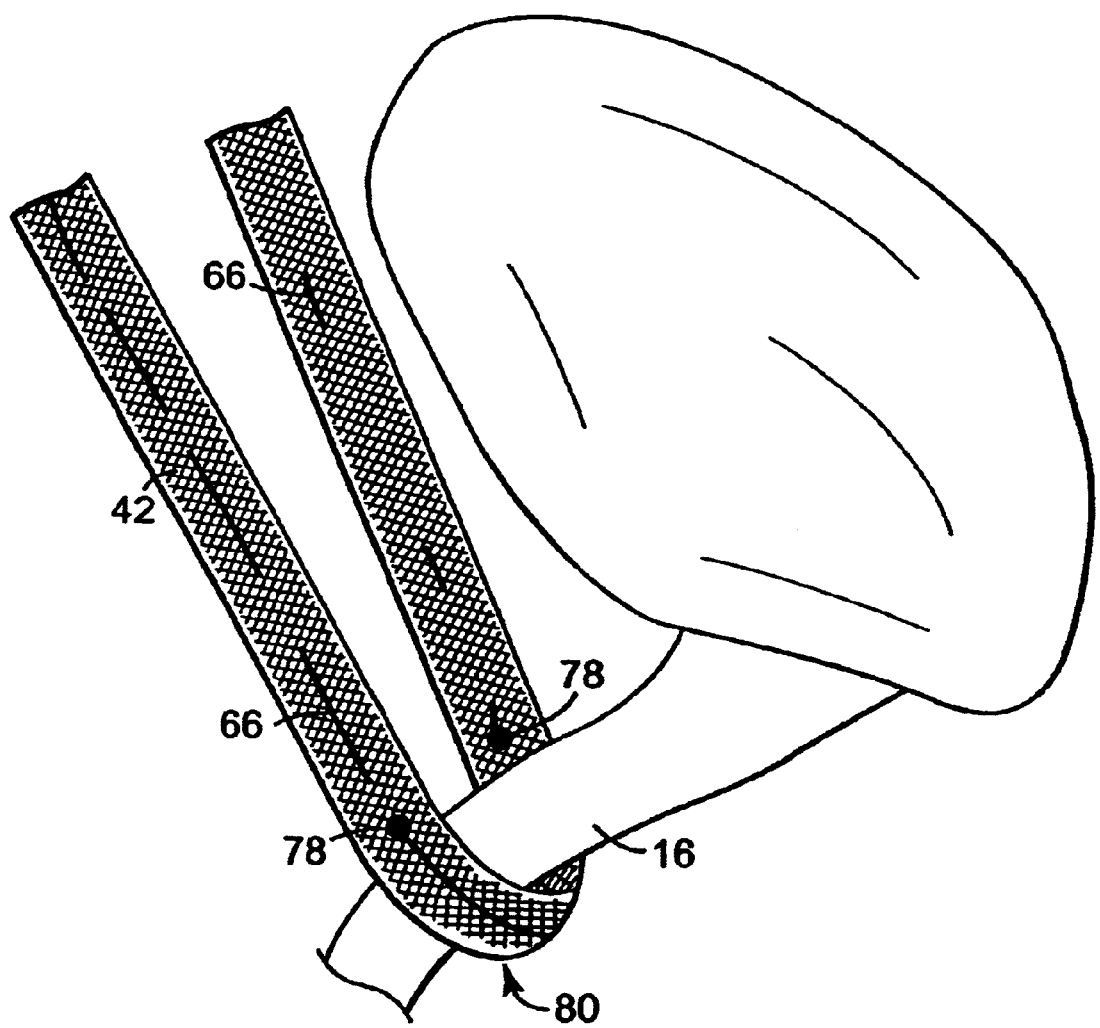
FIG. 7 is a side perspective view of one embodiment of the implanted sling of the present invention.

Several different embodiments of tension adjustment member are within the scope of the present invention. Referring to the embodiment shown in FIG. 7, a mesh sling 42 is shown. A tension adjustment member 66 is woven into the sling and attached to the sling 42 via two attachment points 78 located near the midsection 80 of the sling 42 and also corresponding to locations near each side of the urethra 16.

Other attachment configurations for member 66 are also included within the scope of the claimed invention. The tension adjustment member 66 may be a separate element (e.g. threaded along the length of the sling 42) or it may be an integral part of the sling matrix. The tension adjustment means may comprise one filament threaded along the mesh. Alternatively, more than one filament may be used. The tension adjustment member 66 shown in FIGS. 1 and 1A is attached to the mesh at the ends of the middle portion II. Alternatively, the tension adjustment means may comprise at least one filament that is integrally woven in the mesh and that has extension properties that are different than the other filaments that form the mesh.

The tension adjustment means may be threaded axially along the sling mesh, through the middle of the sling or adjacent its ends. Preferably, this is done at the time of manufacture to provide an assembly that is conveniently used during a surgical procedure, without requiring the surgeon to assemble the sling and tension adjustment means during a surgical procedure. In one embodiment, the tension adjustment means 66 may comprise a plurality of elements woven axially along the sling. The plurality of elements may be parallel or non-parallel. For example, the elements may cross in the support portion II. As another example, the tension adjustment means may comprise a portion of the support portion that is more tightly woven than another portion of the support portion.

Preferably, the tension adjustment member is a continuous, uninterrupted member, as opposed to a member in separate pieces. A continuous, uninterrupted member allows the sling to be tightened and loosened and provides a plurality of locations that can be grasped along the sling 42 to modify the tension of the sling. Also preferably, the member extends the entire length of the sling, from one end to the other. A continuous, uninterrupted member allows the entire sling to be repositioned as opposed to merely isolated portions of the sling.

The tension adjustment member 66 may comprise a monofilament element or a braided member. The tension adjustment member 66 may be constructed from a biodegradable material or a non-biodegradable material or combinations thereof. The monofilament may be round, flat or other shapes to aid in fixation or identification.

The position adjustment member 66 enables surgeons to easily tighten or loosen the sling tension during the surgical procedure, even after the surgeon removes the sheath 44. To reduce the tension of the sling 42 using the position adjustment member 66, the surgeon contacts the sling 42 and position adjustment member 66 adjacent the urethra and pulls away from the urethra. The tension of the sling may be increased by grasping the sling 42 and position adjustment member 66 above the abdominal incision and pulling upward. One or both ends of the sling 42 and position adjustment member 66 may be grasped to increase the tension of the sling 42. Affording adjustment of the sling 42 position after removal of the sheath 44 facilitates proper sling placement and helps avoid complications such as retention and sling erosion arising out of improper sling placement.

The various configurations, properties or characteristics of the position adjustment member 66 may vary or remain constant along the length of the position adjustment member 66. For example, the position adjustment member 66 may be made of a variety of materials including, but not limited to, Prolene, nylon, polypropylene, Deklene™, poly-L-lactide (PLLA), polyethylene glycol (PGA), polyester and any combination of materials. Depending on the desired treatment, the member 66 or portions thereof, may be absorbable, non-absorbable and/or resorbable. If the member 66 is constructed from an absorbable, bioabsorbable or bioresorbable material or the like, then the member 66 may be optionally left in the sling 42 after the surgical procedure. This offers the advantage of affording the use of the tension adjustment member 66 in a minimally or non-invasive near term, post operation sling tension adjustment procedure.

Figure 37:
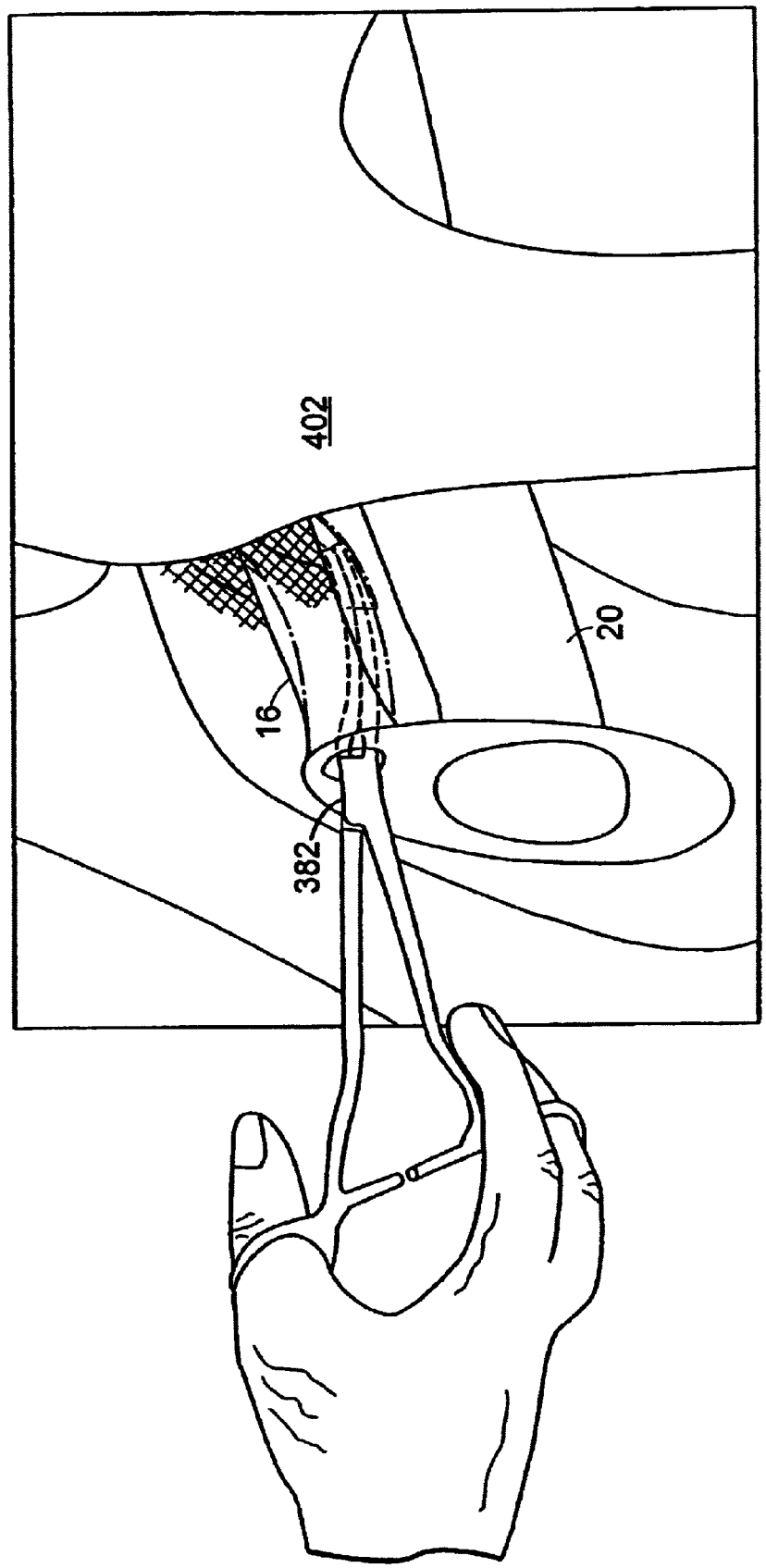
FIG. 37 is a perspective view of another method of adjusting the tension of the sling, showing a method of loosening the tension of the sling either during or even after the surgical procedure.

FIG. 37 illustrates an example of a post operative sling tension adjustment procedure. For example, the patient may be experiencing slight retention shortly after the surgical procedure and the surgeon may wish to slightly loosen the sling 42. While the surgeon may make a slight dissection in the vagina 20 to reach the member 66, the surgeon may also have the option of placing a blunt instrument 382 into the urethra 16 and slightly deflecting the urethra to thereby loosen the tension of the sling in a lasting fashion. In contrast, if this step were attempted with prior art slings, the elastic nature of such slings would likely result in temporary, elastic deformation of the sling without a lasting change in the position of the sling. The prior art procedure also risks loss of sling functionality as previously described.

The individual fibers or filaments comprising the tension adjustment member 66 may be extruded, woven, braided, spun, knitted, non-woven or have other similar configurations. Member 66 properties, such as tensile strength, elongation at break point, stiffness, surface finish, etc., may be similar to or different from those of the sling 42 and may vary along the length of the member 66.

In one embodiment, the tension adjustment member 66 may be secured to the assembly 40 by attaching one or more ends of the tension adjustment member 66 to the sheath 44. In another embodiment, the tension adjustment member 66 is secured to the device 40 simply by interlacing or weaving the tension adjustment member 66 at predetermined points along the length of the sling 42. In yet another embodiment, the tension adjustment member 66 may include one or more points of attachment along the length of the sling 42. The tension adjustment member 66 may be attached to the sling assembly 46 via knotting, weaving, bonding, ultrasonic welding or other attachment techniques, including combinations thereof, to prevent tension adjustment member 66 detachment during and/or following sling implantation.

Preferably, the tension adjustment member 66 is knotted at preselected locations along the length of the sling 42 without any additional elements added to the assembly to connect the member 66 to the sling 42. Knotting allows attachment of the member 66 to the sling 42 without additional securement structure. This embodiment avoids contact between such additional retaining structure and tissue and any attendant complications. The knot may comprise a single throw, half hitch knot, square knot; single overhand knot, a slipknot or a heat formed knot. Optionally, a loop or other shape may be formed in the member 66 adjacent the end 61 of the support portion II to afford convenience in identifying the end 61 of the support portion II. Such a loop or other shape may be conveniently located and cut should it be desired to remove the portion of the member 66 associated with the support portion II.

It is noted that, in an embodiment with a continuous length position adjustment member 66 that is anchored at a plurality of locations 61 (as shown in FIGS. 1 and 1A), when a user grasps a mid portion II of the sling 42 and member 66 and pulls, some of the pulling force is distributed or transmitted from the grasped location to a plurality of attachment points 61. This is believed to assist in providing a sling that is more effectively repositioned in a permanent fashion.

Figure 6:
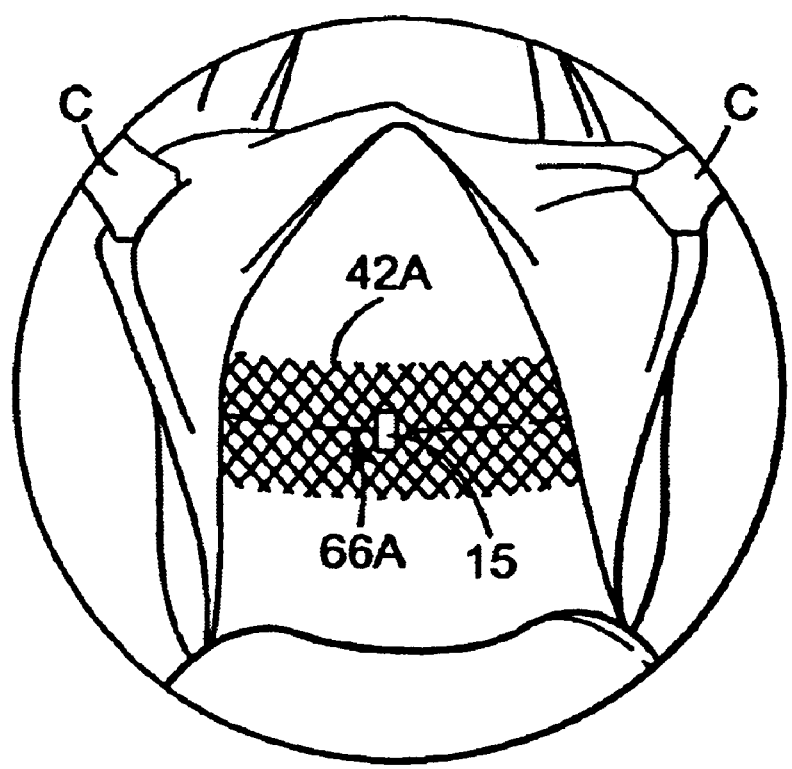
FIG. 6 is an end view showing a vaginal incision and a sling properly located according to an aspect of the present invention.

The means 66 for adjusting the tension or anatomical location of the sling 42 may optionally comprise a means for indicating proper orientation of the sling 42. Referring to FIG. 1, the tension adjustment element 66 is woven along the length of the sling 42. In the support portion II of the sling 42, the tension adjustment element 66 is woven more frequently 67 than the less frequent weave 69 of the element 66 in the end portions I of the sling 42. Additionally, as shown in FIGS. 1 and 1A, a majority of the element 66 is woven above one major side surface of the sling 42 in the support portion. As shown in FIG. 6, the major side of the sling with the majority of protruding tension adjustment means 66A is located opposite the urethra. If the material of the element 66A is constructed of a different color, shape or size relative to the material of the sling 42A, the surgeon may more readily visualize proper placement of the sling 42A.

Figure 8A:
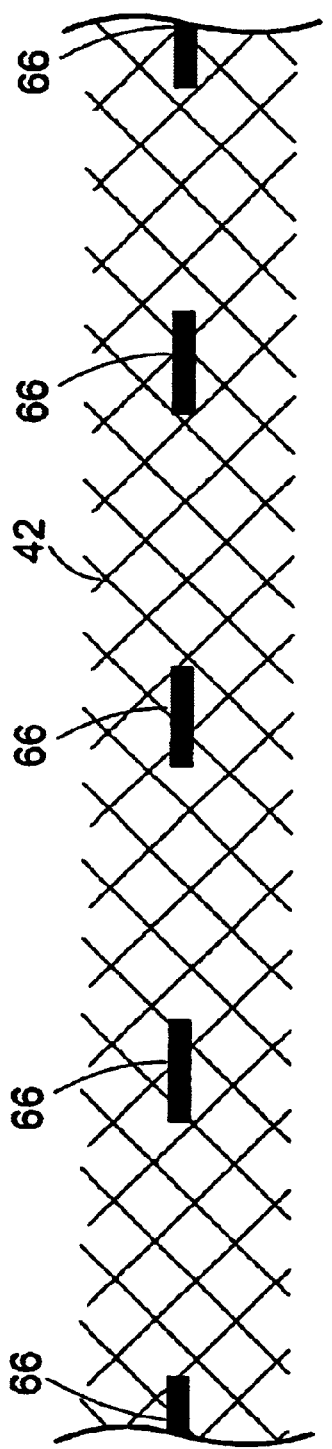
FIG. 8A is a top view of sling showing a side of the sling that is preferably placed facing the urethra.
Figure 8B:
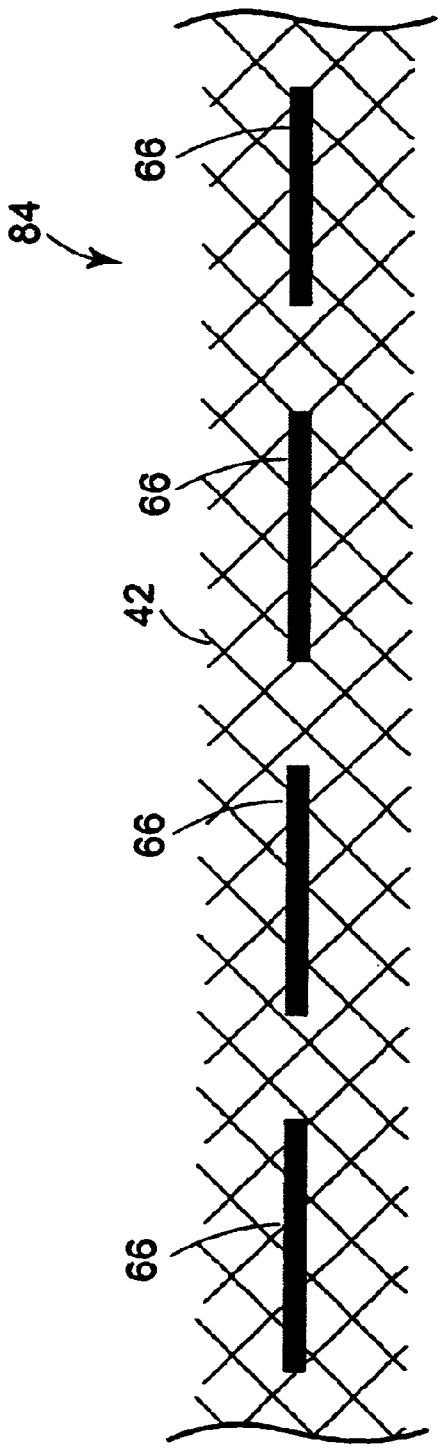
FIG. 8B is a top view of the sling of FIG. 8A, showing the side of the sling opposite the side of the sling shown in FIG. 8A, which side is preferably positioned opposite the urethra.
Figure 8C:
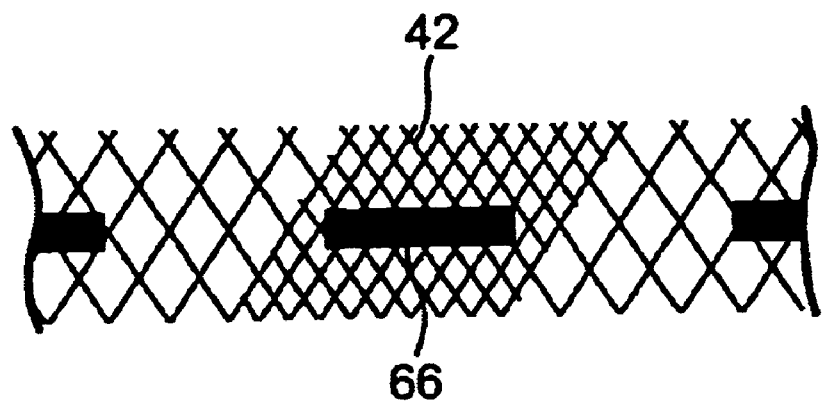
FIG. 8C schematically illustrates examples of adjustment members.

Referring to the embodiment of the invention shown in FIGS. 8A and 8B, the tension adjustment member 66 is woven approximately along the centerline or axial length of the sling 42. In one embodiment, the weave pattern of the tension adjustment member 66 is used as an indicator of proper sling orientation after implantation. For example, the weave pattern on a first major side surface 82 of the sling 42, shown in FIG. 8A, has small segments or loops of exposed member 66. The second major side surface 84 (i.e. opposite side 82 or reverse side) of the sling 42, shown in FIG. 8B, has larger segments or loops of exposed tension adjustment member 66. Upon implantation of the sling 42, the first surface 82 of the sling 42, having minimal lengths of filament segments or loops protruding above the material of the sling 42, is preferably positioned to face the urethra 16 of the patient. It is preferred that this first surface 82 of the sling 42 face the urethra 16 to minimize filament 66-urethra contact, particularly during adjustment of the sling 42, and to assist the surgeon in identifying the location of the member 66.

In another embodiment of the invention, one or more substances may be associated with the member 66 by, for example, a coating process. The coatings may be selected from the same group mentioned above with respect to coatings for the sling 42. The substances may be used to enhance treatment effects, indicate proper sling orientation, enhance tension adjustment member visibility, and resist infection or other effects. For example, the tension adjustment member 66 may be dyed a contrasting color (e.g. blue) with respect to the sling color (e.g. white). The contrasting color of the tension adjustment member 66 provides the surgeon with a visual indicator that can be used to confirm proper sling orientation. In addition to coating substances, other components including, without limitation, tags, labels or indicia may also be used to indicate proper sling orientation or enhance tension adjustment member 66 visibility/identification.

FIG. 6 illustrates a sling 42A in a proper position. The surgeon may look through the vaginal incision and view substantially all of the position adjustment member 66A protruding above a support 11 (see FIG. 1A) or middle portion of the sling 42A when the sling 42A is properly placed. If only a minor portion of the position adjustment member 66A is visible protruding above a major surface of the sling 42A, then the sling is misplaced and corrective action should be taken. Once the sling 42A is located in its final position, the portion of the position adjustment member 66A in the support portion II of the sling (see FIG. 1A) may optionally be cut or released at the ends 61 of the support portion II and removed prior to closing the vaginal incision. Optionally, the sling 42A may include a means for conveniently locating and cutting the tension member 66A at this point to assist in removal of that portion of the tension member 66. As described above, that means may comprise a loop or other shape in the tension member 66. Alternatively, but not preferably, a structure attached to the position adjustment member 66 my be used to facilitate visualization, maneuverability and cutting of the position adjustment member 66.

Also optionally, the sling 42A may include a means for grasping the sling 42A and/or the tension member 66A in the support portion II of the sling. For example, the means may comprise a small handle 15 attached to the tension member 66 in the support portion II of the sling 42A.

Referring to FIGS. 4 and 5, the sling 42 and tension adjustment member 66 may be at least partially housed within a sheath 44. Preferably, the sheath 44 is made of a relatively transparent and flexible material having a smooth outer surface. The transparency of the sheath 44 enables a manufacturer or user of the device 40 to view the sling and tension adjustment member 66 encased within the sheath 44 and visually determine whether the sling 42 assembly contains any defects, such as a twisted sling, detached tension adjustment member 66, torn sling fibers or other related flaws, as well as orientation within the sheath. In addition, the sheath provides a protective covering for the sling 42 and tension adjustment member 66 which also resists bacterial and viral contamination of these components.

In a preferred embodiment, the sheath 44 is made of polyethylene. Other materials including, without limitation, polypropylene, nylon, polyester or Teflon may also be used to fabricate the sheath 44. The sheath material should be flexible and provide sufficient structural integrity to withstand the various forces exerted on the sheath 44 throughout the sling delivery procedure. In general, the sheath 44 is configured to have sufficient flexibility to facilitate user manipulation and adequate structural strength to withstand the various forces applied to the sheath 44 during delivery and/or positioning of the sling assembly 46. It should also conveniently separate from the sling material 42 after the sling 42 is implanted without materially changing the position of the sling 42.

Figure 9A:
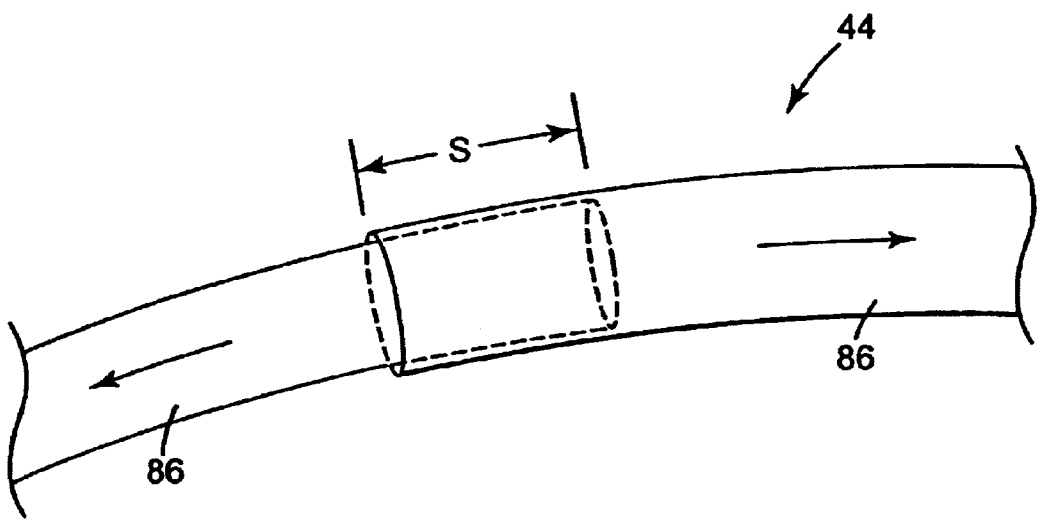
FIG. 9A is a perspective view of an embodiment of sheath according to the present invention.

As shown in FIG. 9A, the sheath 44 preferably comprises two elongate sections 86, portions of which detachably and telescopically overlap near the middle portion 80 of the sling (not shown). In a preferred embodiment, the length S of the overlapping section is approximately 3.8 cm (1.5 inch). However, alternative lengths may also be used. The length is preferably sufficient to resist exposure of most of the sling 42 and tension adjustment member 66 prior to sheath 44 removal. In addition to resisting sling exposure, the overlapping section may also be used as a visual indicator for the practitioner or user of the device. In particular, positioning the overlapping portion of the sheath 44 under the bladder neck or urethra 16 ensures proper sling placement (e.g. symmetrical sling placement) and tension within the patient. Additionally, orientation indicia (not shown) may be placed on the overlapping portion to indicate proper orientation of the sling relative to the urethra 16.

Alternatively, other configurations of the sheath 44 are within the scope of the present invention. In particular, the sheath may be unitary as opposed to telescoping with perforations, holes, scores or tear lines designed to allow separation and removal of the sheath 44.

Figure 9B:
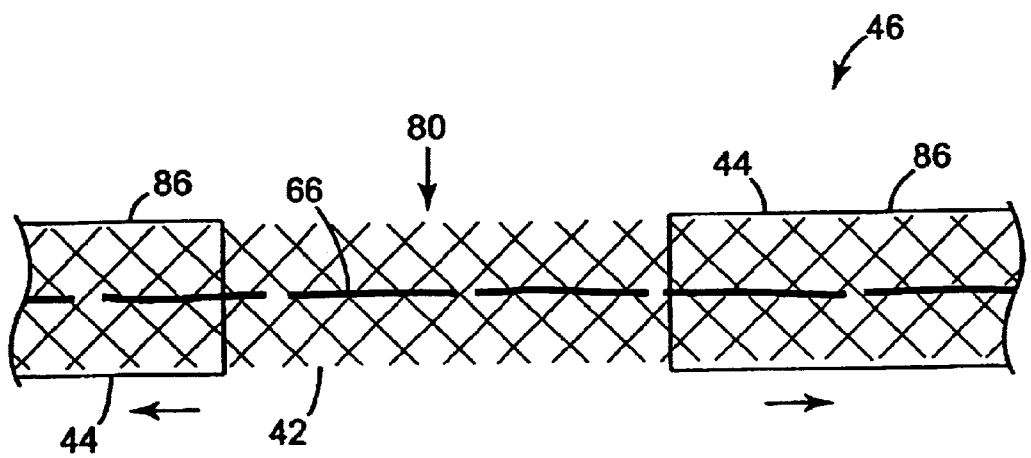
FIG. 9B is a bottom view of a sheath and sling assembly according to the present invention after slight removal of the sheath.

During sheath removal, the first section 86 and the second section 86 of the sheath 44 are slid off the sling 42 by pulling each end of the sheath 44 away from the middle portion 80 of the sling assembly 46 (as shown by reference directional arrows in FIG. 9B). Removal of the sheath 44 causes separation of the overlapping sheath sections, thereby exposing the sling 42 and tension adjustment member 66. In addition, the smooth outer surface of the sheath 44 provides a relatively frictionless surface to facilitate passage of the sheath 44 through the various tissues. The relatively frictionless motion also avoids disturbing the position of the sling 42 relative to the anatomy of the patient.

In another embodiment of the invention, the sheath 44, or a portion thereof, is associated with one or more substances including those substances identified with respect to the member 66 and sling 42. The substances may be used to enhance sheath removal, identify twists along the sheath 44 (and thereby indicate proper sling orientation), indicate cutting/separation points, indicate center-point, resist infection or provide other desirable effects. For example, a first surface of the sheath 44 may include a colored stripe that should lie opposite the urethra 16 or bladder neck to ensure proper sling orientation. Thus, the stripe provides the practitioner/surgeon with a visual indicator to aid in properly orienting the sling assembly 46, and ultimately the sling 42, within the patient.

The ends of the sheath are preferably connected to a dilator. Alternatively, the sheath may be connected to the sling, and the sling can be associated with the dilator. The number of dilators will depend on factors such as the shape of the sling. For example, the sling 42P shown in FIG. 41 includes four dilators 54P.

At least two dilators are preferred. The sling 42 shown in FIG. 4 includes two dilators. The first end 48 and second end 50 of the sheath 44 are preferably configured for attachment to a dilator 54.

The dilator 54 is a component that atraumatically creates and/or expands the passageway through the tissues for sling assembly delivery. The dilator 54 includes a means for associating with a needle 60. The dilator 60 is preferably short relative to a needle 60 for ease of passage of the assembly and to reduce the overall amount of tissue that is deflected at one time. Preferably, the dilator is less than 2.5 inches in length, and more preferably, it is less than one inch in length. The maximum radius of a dilator 54 is preferably less than 10 mm, more preferably less than 7.5 mm, even more preferably less than 5 mm. The tip of the dilator 54 is preferably blunt, as, in preferred embodiments, the leading tip of the dilator 54 will pass through tissue that has already been pierced by a needle 60.

The dilator 54 may be made from a variety of biocompatible and sterilizable materials including, without limitation, acetal, Delrin®, Acrylonitrile-Butadiene-Styrene (ABS), polyethylene, nylon and any combination of materials. Alternatively, the sheath 44 may be additionally or solely connected to an end portion of the sling 42.

The dilator 54 preferably includes means for associating with a surgical needle 60. In a preferred embodiment, the association means affords a permanent affixation between the dilator 54 and the needle 60. By "permanent affixation", it is meant that it would be very difficult to manually separate the dilator from the needle after they have become permanently affixed. After implantation of the sling 42, to separate the sling 42 from the dilator 54/needle 60, the surgeon cuts an end of the sling 42 as described more fully below. The association means preferably affords quick and convenient attachment of the dilator 54 to the needle 60 to avoid wasting time in the midst of a surgical procedure. The attachment should also be secure to avoid separation of the needle 60 and dilator 54 while the combination is passed through tissue.

The dilator 54 also includes a means for association with the sling 42 and/or the sheath 44. For example, the dilator 54 may be preattached to the sling 42 and/or sheath 44, particularly if the sling is a synthetic material. Alternatively, the dilator may include means for conveniently attaching to a sling material (e.g. cadaveric or autologous sling material) just prior to sling placement.

Referring to the embodiment of FIGS. 10A–10E, the dilator 54 may be approximately 3.1 cm (1.2 inches) in length. The dilator 54 preferably includes a gentle taper 88 near its second end 56. The dilator is sized and shaped to provide atraumatic passage through body tissue. The taper 88 and relatively smooth outer surface of the dilator 54 facilitate atraumatic passage of the dilator 54 and attached sling assembly 46 through the various tissues of the patient. The presence of the dilator 54 allows a gentle transition between the diameter of the needle, to the shape of the dilator, and finally to the sling assembly 46, as opposed to prior art assemblies, where the structure of the sling assembly abruptly increases the profile of the needle and thereby the size of the structure that must pass through tissue.

Figure 10A:
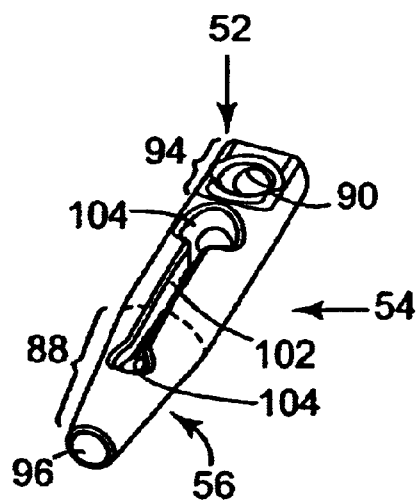
FIG. 10A is a perspective view of a dilator according to an aspect of the present invention.
Figure 10B:
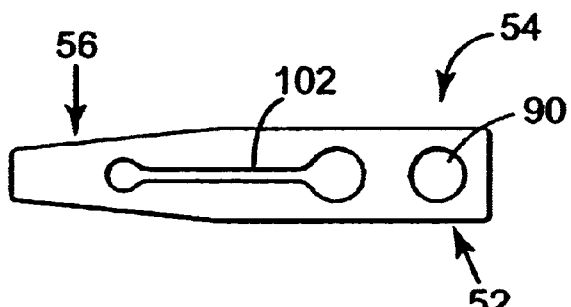
FIG. 10B is a top view of the dilator of FIG. 10A.
Figure 10C:
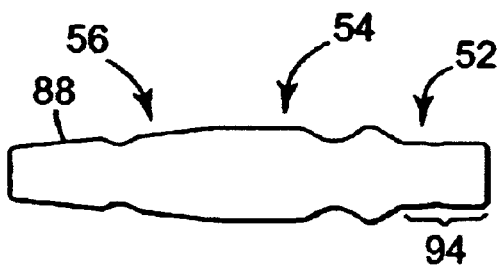
FIG. 10C is a side view of the dilator of FIG. 10A.
Figure 10D:
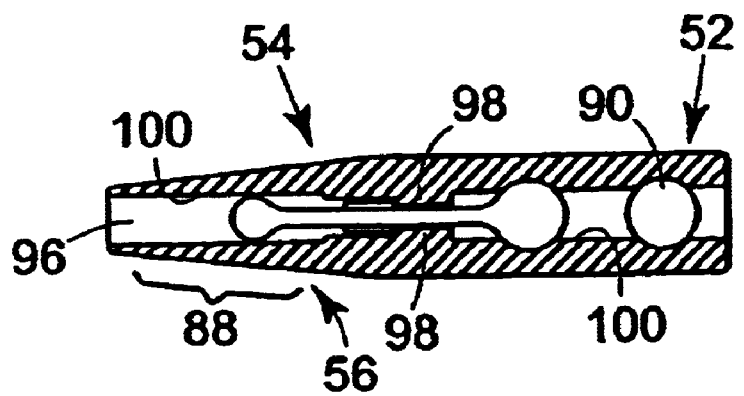
FIG. 10D is a sectional view of the dilator of FIG. 10A.
Figure 10E:
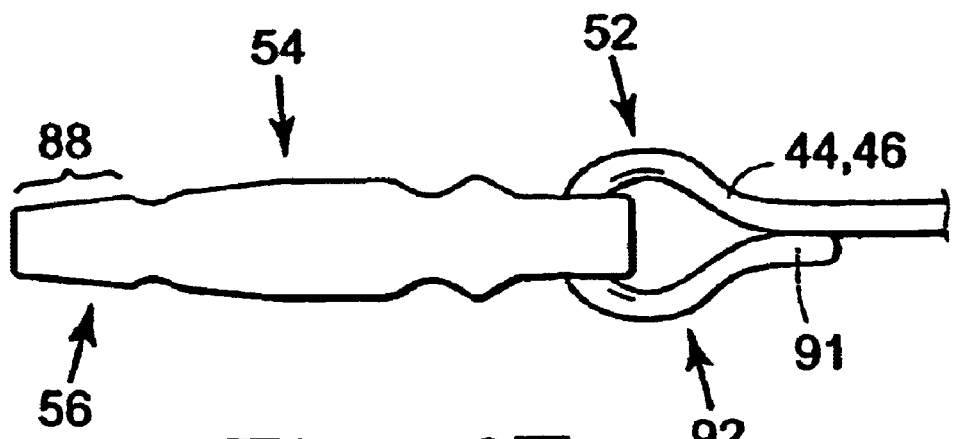
FIG. 10E is a side view showing a dilator assembled to either a sheath or sling according to aspects of the present invention.

Preferably, the first end 52 of the dilator 54 attaches to one end of the sling 42, or sheath 44 or sling assembly 46 (shown in FIG. 10E) and the second end 56 of the dilator 54 may be quickly attached or assembled to a needle 60 (not shown). The sheath 44 is preferably attached to the dilator 54 via a first opening or through-hole 90 located near the first end of the dilator 54. In this embodiment, the opening 90 operates as a universal sling material or assembly attachment point which can receive a variety of materials, such as fascia, autologous materials, synthetics, biologic tissues and any other similar tissues, including any combinations. The edge portion 91 of one end of the sheath 44 is threaded through the opening 90 of the dilator 54 and secured to the sheath 44, thereby forming a loop 92. The edge portion 91 may be fastened onto the sheath 44 via ultrasonic welding, bonding, melting, suturing, sealing or other attachment techniques. Further, as shown in FIGS. 10A and 10B, the first end 52 of the dilator 54 includes a cut-away section 94 to provide room to receive sling assembly material to reduce the overall profile of the sling assembly experienced by tissue during sling passage. Therefore, when the sheath is attached to the cut-away section, the additional sheath material is not apt to significantly increase the relative thickness, diameter or profile of the dilator 54.

Alternatively, for dilators 54 manufactured via molding techniques, the end of the sheath 44 may be encased within and secured to the first end 52 of the dilator 54 during the molding process. In yet another embodiment, the end of the sheath 44 may be fixedly attached within a longitudinal slot located near the first end 52 of the dilator 44 using an adhesive, ultrasonic welding or other attachment techniques.

Referring to FIGS. 10A–10D, the second end 56 of the dilator 54 includes a second opening or through-hole 96 that extends substantially internally along the longitudinal axis of the dilator 54. The second opening 96 has an internal diameter generally configured for convenient attachment to a needle 60 or similar sling-delivery device. In one embodiment, the internal diameter of the second opening 96 of the dilator 54 is approximately within the range of 0.239 cm to 0.318 cm (0.094 inch to 0.125 inch). A shoulder 98 located on the surface 100 of the second opening 96 of the dilator 54 and a complementary mating recess located on the surface of the first end of the needle 60 (see FIG. 4) securely and permanently attach or lock the dilator 54 and needle 60 together. Once the needle 60 is inserted into the dilator 54, they are preferably not separated thereafter. After the sling 42 is implanted, the connected needle 60 and dilator 54 are removed from the sling by cutting an end of the sling as described in greater detail below. Preferable, the needle 60 and dilator 54 are disposed.

One or more longitudinal slots 102 located on the outer surface of the dilator 54 and in communication with the second opening 96 allow the wall of the dilator 54 to expand in a radially outward direction when the first end of the needle 60 is inserted into the second opening 96 of the dilator 54. When the shoulder 98 of the dilator 54 passes the recess of the needle 60, the wall of the dilator 54 collapses around the needle 60 as the shoulder 98 seats into the recess, thereby securing the dilator 54 on the needle 60 and blocking separation of the dilator 54 and needle 60.

Although the invention has been described in terms of a shoulder 98 and mating recess, alternative dilator-needle attachment mechanisms such as bumps, grooves, slots, wedges, tabs and other mechanisms are also included within the scope of the claimed invention. The dilator 54 preferably includes one or more relief ports 104 to facilitate convenient needle connection. The relief ports 104 may be formed at the ends of the longitudinal slots 102 or at various high-resistance locations along the dilator 54. The relief ports 104 decrease the rigidity or resistance of radially outward expansion of the dilator wall and, reduce the amount of force required to insert or securely attach the needle 60 to the dilator 54. In yet another embodiment, superficial bands or rings, arc-shaped slots, superficial grooves or other mechanisms may be provided to provide improved expansion or attachment characteristics.

A portion of the dilator 54 includes a taper 88 having a decreasing profile toward the second end 96 of the dilator 54. The taper 88 preferably gently cams tissue out of the path of the sling assembly 46 as the sling assembly is inserted in the body. The taper 88 is also sized and shaped to reduce the amount of friction or resistance as the device is drawn through the tissues of the patient. The amount of force required to manipulate the device through the tissues is thereby reduced. This in turn provides the user of the assembly with additional control over device insertion and maneuverability through tissue and within the patient. In addition to tapered profiles, other dilator profiles such as conical, flared, frustoconical, pyramid-shaped, elliptical or other applicable profiles may also be used. Overall, the profile of the dilator 54 is preferably configured to provide easy dilation of the tissue to accommodate smooth passage of the sling 42/sling assembly 46 and subsequent collapse of the surrounding tissue to securely anchor the sling 42 into the tissue (after sheath removal).

Figure 12A:
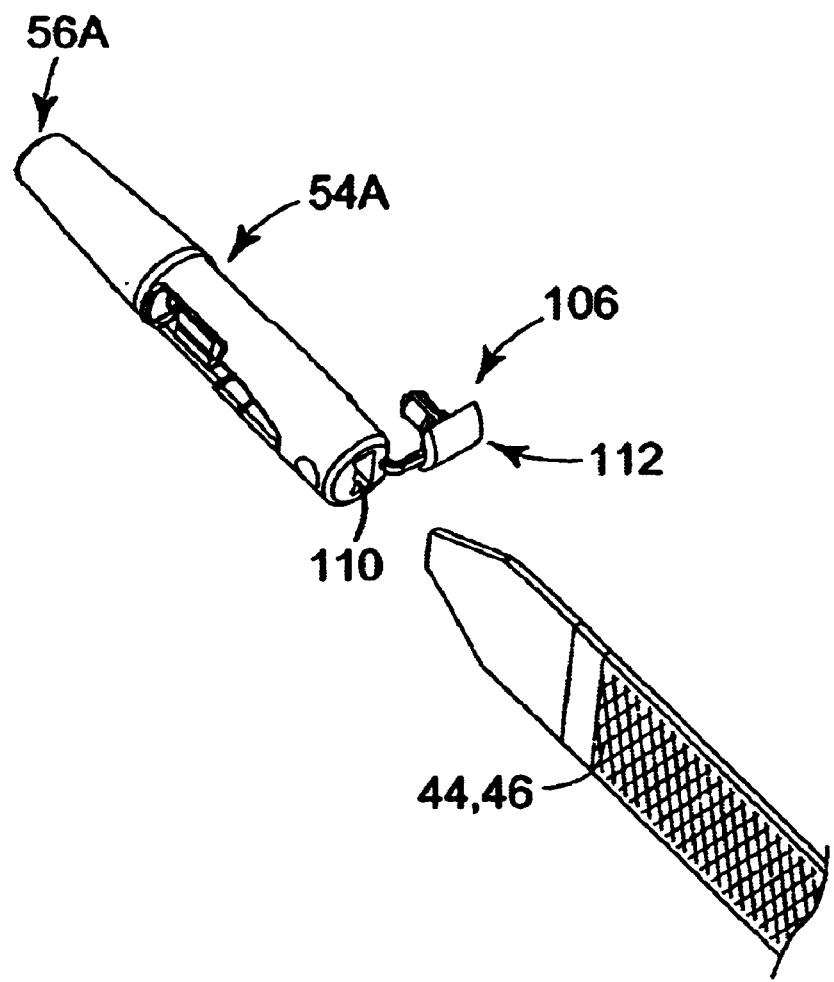
FIG. 12A is a perspective view of another embodiment of the dilator of the present invention and portions of a sling assembly or sling in a disassembled condition.
Figure 12B:
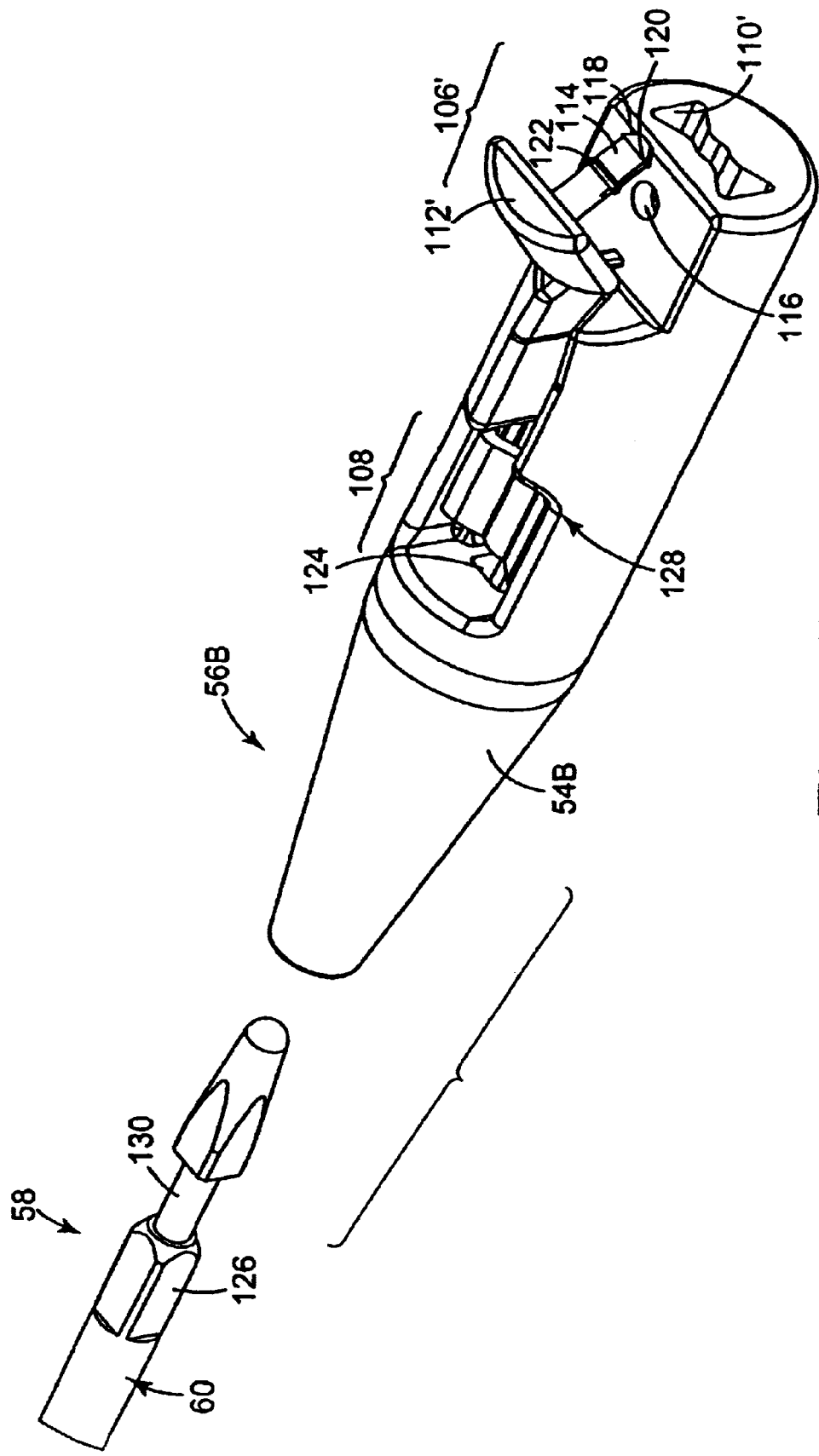
FIG. 12B is a perspective view showing the dilator of FIG. 12A and an insertion needle in a disassembled condition.

In other embodiments of the invention shown in FIGS. 12A and 12B, the dilator 54A or 54B includes a sling fastening snap mechanism 106 on one end of the dilator. The embodiment disclosed in FIG. 12A includes a keyed/locking mechanism on its other end. As shown in FIG. 12A, the first end of the dilator 54A includes a slot or slot-shaped opening 110 configured for convenient insertion of one end of a sling 42 (such as one made from autologous tissue) or sling assembly 46 either at the surgical site (e.g. by the operating room nurse or surgeon) or other location (such as manufacturing location). Additional shapes for the dilator opening 110 include, without limitation, oval, circular, square, rectangular and other shapes. The slot-shaped opening 110 is located along a portion of the longitudinal axis of the dilator 54A.

Referring to FIG. 12B, a snap-like element 112' is located on an outer surface near the first end of the dilator 54B. The snap-like element 112' includes a barb or spike 114 that fits within an opening 116 situated near the first end of the dilator 54B. The opening 116 for the barb 114, preferably configured perpendicular to the slot-shaped opening 110', is sized and shaped to match or mate with the barb 114 of the snap-like element 112'. When the barb 114 is fully seated within the opening 116 of the dilator 54B, the tip 118 of the barb 114 extends into the slot-shaped opening 110' of the dilator 54B. A first ridge 120 and a second ridge 122 located along the length of the barb 114 further secure and/or fasten the barb 114 within the opening 116 of the dilator 54B. Other fastening configurations including, but not limited to, bumps, shoulders, tabs, detents, tongue in grooves, snaps and any combinations of fastening means may also be used with the present invention.

During use, one end of the sling 42, sheath 44 or sling assembly 46 is inserted into the slot 110' of the dilator 54B. With the end of the sling 42/sling assembly 46 properly positioned within the slot 110', the barb 114 of the snap-like element 112' is inserted into the opening 116 of the dilator 54B. The barb 114 is fully seated within the opening 116 when both ridges 120, 122 pass through the opening 116 of the dilator 54B. This causes the tip 118 of the barb 114 to bear down on or penetrate a portion of the sling 42/sling assembly 46 extending within the slot 110' of the dilator 54B, thereby securely fastening the sling 42/sling assembly 46 to the dilator 54B.

A keyed/locking mechanism 108 is located near the second end 56B of the dilator 54B. As shown in FIG. 12B, a square-shaped opening 124 extends along a portion of the longitudinal axis near the second end 56B of the dilator 54B. The shape of the dilator opening 124 matches the square-shaped perimeter of the keying-segment 126 located near the first end 58 of the needle 60 and allows keyed-rotation of the dilator 54B at ninety-degree intervals. Other appropriate shapes for the dilator opening 124 may also be used provided that the shape of the opening 124 complements the corresponding keying-segment shape located near the first end 58 of the needle 60. When the first end 58 of the needle 60 is positioned within the dilator 54B, the square-shaped opening 124 of the dilator 54B together with the keying-segment 126 of the needle 60 prevents axial rotation of the dilator 54B relative to the needle 60 and, thus, twisting of the sling 42/sling assembly 46. This optional feature provides the practitioner or user of the assembly with improved control and maneuverability of the assembly before and during the insertion procedure.

The dilator 54B also includes a locking mechanism 128. Referring to FIG. 12B, the locking mechanism 128 comprises one or more tension-loaded ribs located within the longitudinal opening of the dilator 54B. The configuration of the ribs generally matches and corresponds to a complementary recess 130 located near the first end 58 of the needle 60. Thus, the first end 58 of the needle 60 is inserted through the longitudinal opening 124 of the dilator 54B until the ribs of the dilator 54B seat within the recess 130 of the needle 60. The dilator 54B is securely attached or locked onto the needle 60 when the dilator ribs are fully seated within the needle recess 130. Although the invention has been described in terms of a rib and complementary recess, alternative dilator-needle attachment mechanisms, such as those previously described, are also included herein.

Figure 13:
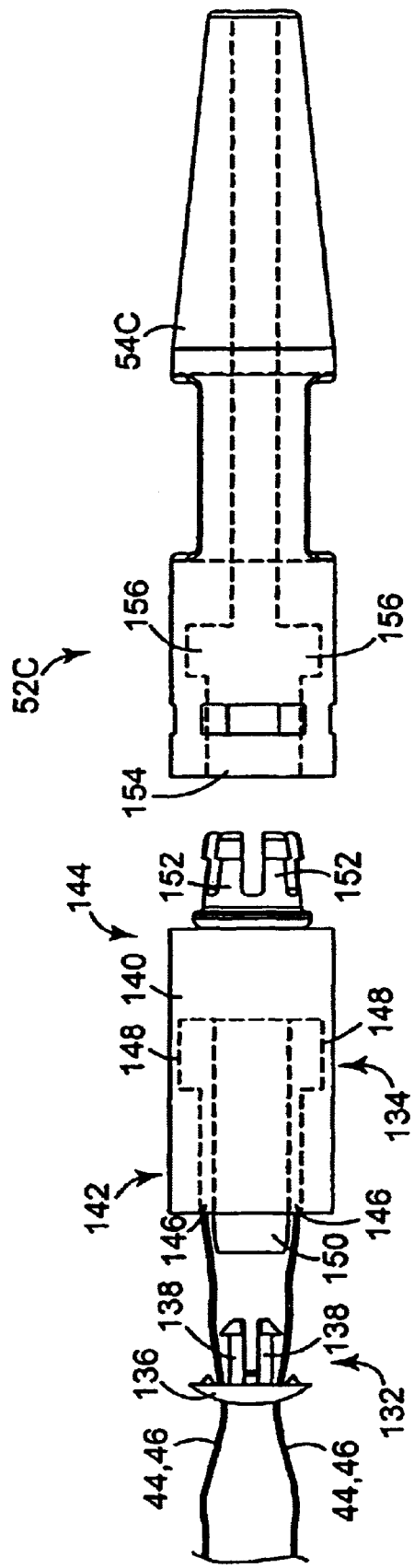
FIG. 13 is a side view of another embodiment of the dilator of the present invention and portions of a sling or sling assembly, showing the dilator in an unassembled condition.

Referring to FIG. 13, in an alternate embodiment of the invention, the sheath 44 (or sling 42 or assembly 46) is attached to the dilator 54C via a locking (or compression) collet 132 and adapter connector 134. The compression collet 132 comprises a ring-shaped portion 136 having one or more barbed snap tongs 138. The complementary adapter 134 comprises a cylindrical element 140 having a first end 142 and a second end 144. The internal profile near the first end 144 of the adapter connector 134 includes a tubular lumen or channel 146, having one or more recesses, shoulders, grooves or similar indentations 148, surrounding an internal prong 150. The second end 144 of the adapter connector 134 includes one or more barbed snap tongs 152, similar to the tongs 138 of the compression collet 132. In addition, the first end 52 of the dilator 54C includes a longitudinal opening 154 having one or more recesses, grooves, slots or related types of indentations 156 configured to engage the tongs 152 of the adapter connector 134.

In use, one end of the sling 42/sling assembly 46 of the present invention is configured into a tubular or appropriate shape that enables a sufficient portion of the end of the sling 42/sling assembly 46 to be inserted through the compression collet 132. The tongs 138 of the compression collet 132 are then inserted into the first end 142 of the adapter connector 134, causing the tongs 138 to snap into engagement with the adapter connector 134. The end portion of the sling 42/sling assembly 46 is compressed between the tongs 138 of the compression collet 132 and the internal prong 150 of the adapter connector 134, thereby securely fixing the sling 42/sling assembly 46 to the collet/adapter assembly. In a similar fashion, the tongs 152 of the adapter 134 are then inserted and snap-locked into the first end 52C of the dilator 54C, creating a secure fixation between the collet/adapter assembly and dilator 54C.

Figure 14A:
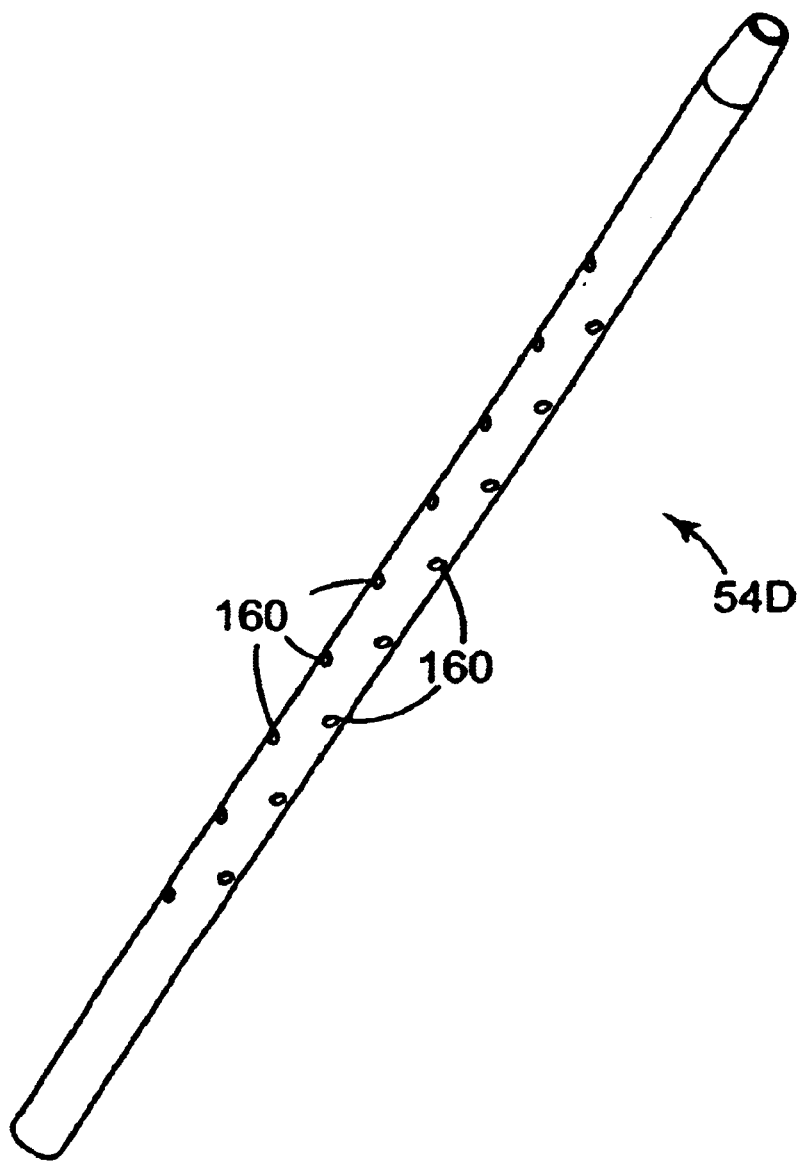
FIG. 14A is a perspective view of another embodiment of a dilator/cystoscopy aid of the present invention.
Figure 14B:
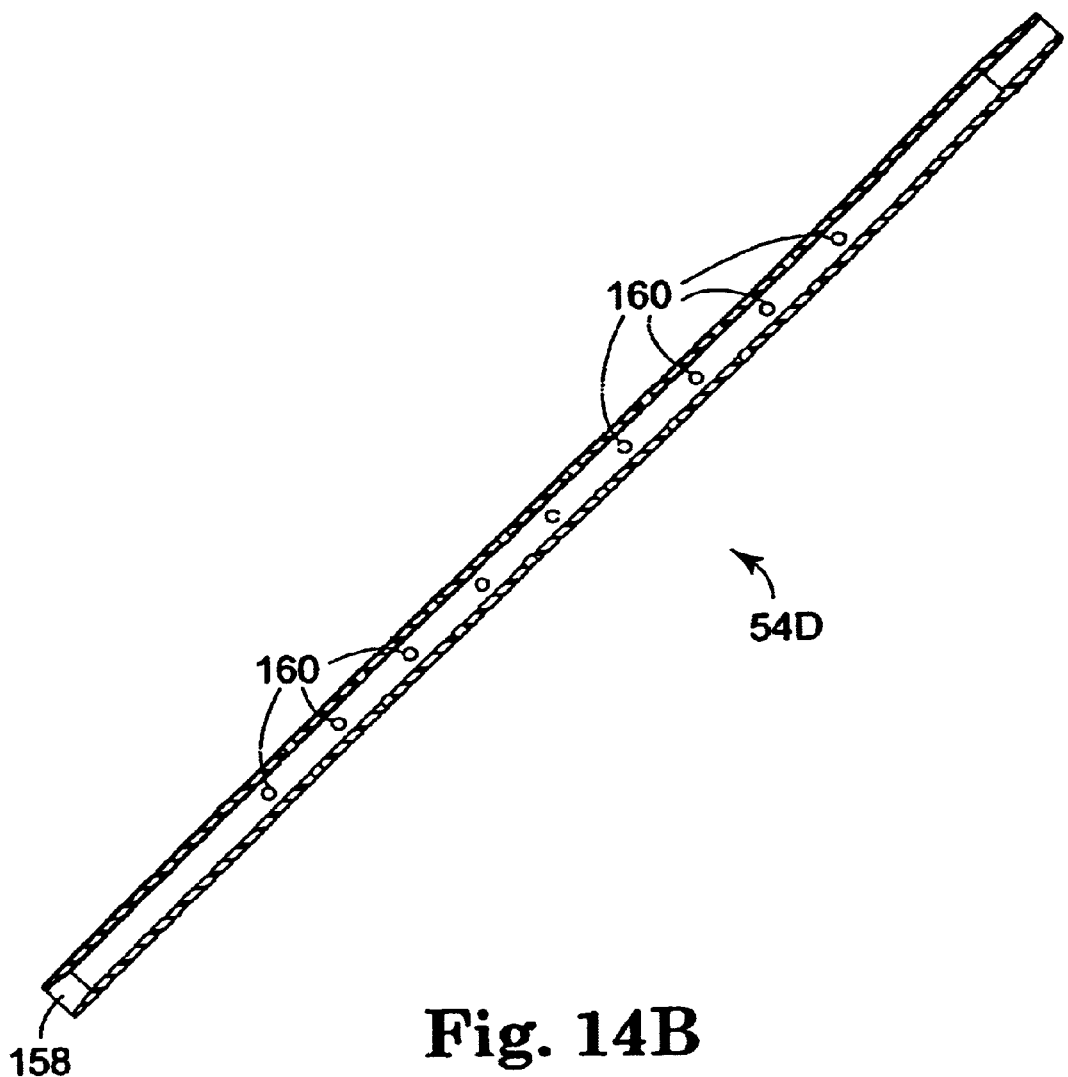
FIG. 14B is a sectional view of the dilator/cystoscopic aid of FIG. 14A.

In another embodiment of the invention, the length of the dilator 54D is substantially equivalent to the length of the needle 60 used for the sling delivery procedure. For example, as shown in FIGS. 14A and 14B, the dilator 54D comprises a hollow, atraumatic trocar-shaped component generally made of a soft, semi-flexible material, such as high density polyethylene, polypropylene, polyvinyl chloride (PVC), polytetrafluoroethylene (PTFE) or other similar materials, including combinations thereof. The material and design of the dilator 54D allows the dilator to be positioned over or passed along the length of the needle 60, thereby totally or partially encasing the needle 60, similar to an Amplatz sheath/dilator. In the spirit of convenience and brevity, this embodiment of the dilator 54D will be hereafter referenced as the cystoscopy aid 54D. Optionally, tongue and groove structure may be supplied in the needle 60 and cystoscopic aid 54D to guide the cystoscopic aid 54D along the needle 60.

Alternatively, the hollow portion or internal lumen 158 of the cystoscopy aid 54D may be sized and shaped to accommodate passage of a dilator 54 and/or sling 42 and/or sling assembly 46, similar to those previously described. As such, after the cystoscopy aids 54D are positioned over the needles 60, the dilators 54 and/or sling 42 and/or sling assembly 46 are connected onto the ends of the needles 60. The needles 60 and attached components are then pulled through the internal lumen 158 of the cystoscopy aids 54D until the sling 42 is positioned adjacent the target site or urethra 16 and the needles 60 connected components are withdrawn from the patient. With the sling 42 properly positioned in a therapeutically effective relationship with the urethra 16, the cystoscopy aids 54D are then removed from the patient, allowing the tissue to gently collapse around the sling 42. This configuration of the device allows components such as dilator 54, sling assembly and subsequent needle maneuvering to be performed substantially within the hollow portion 158 of the cystoscopy aid 54D, thereby reducing potential tissue trauma and infection.

In an alternate embodiment, one or more apertures or perforations 160, that function to facilitate verification of bladder and urethra integrity, are disposed along the length of the cystoscopy aid 54D. For example, during use, after the needles 60 have been inserted within the patient, the cystoscopy aid 54D may be pushed along the exterior surface of each needle 60. If the bladder has been punctured during needle insertion causing urine leakage or drainage within the patient, the urine or bladder fluid will enter the apertures 160 of the cystoscopy aid 54D and flow along the surface and out from the needle 60. This allows the practitioner to quickly and easily confirm urethra and bladder integrity.

Figure 14C:
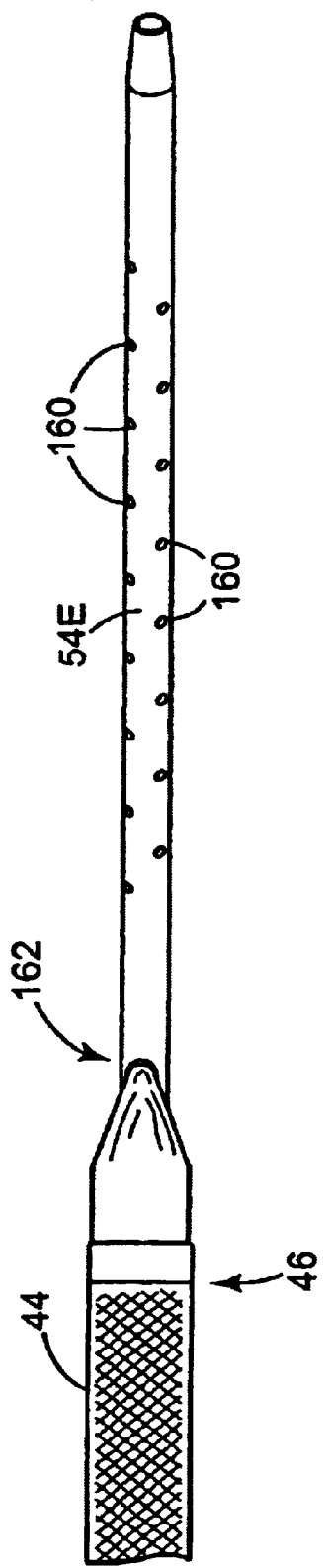
FIG. 14C is a side view of a cystoscopic aid/dilator attached to a sling assembly according to the present invention.

In another embodiment of the invention, shown in FIG. 14C, a first end 162 of the cystoscopy aid 54E is attached to an end of a sling 42, or sling assembly 46 or portions thereof. The sling 42/sling assembly 46 may be attached to the cystoscopy aid 54E using attachment mechanisms and techniques similar to those previously described throughout this disclosure. Following handle 64 removal, cystoscopy aid 54E is pushed along the exterior of a needle 60 to maneuver and properly position the sling 42/sling assembly 46 in a therapeutic position relative to anatomical structures such as the urethra or bladder.

Alternatively, the cystoscopy aid 54E or dilator 54 may include a hollow portion configured to house the sling assembly 46. In other words, the sling 42/sling assembly 46 would be folded, rolled or similarly configured for placement inside the hollow portion of the dilator or cystoscopy aid 54E. One role of the dilator 54E or cystoscopy aid 54E in this embodiment, similar to that of the sheath 44, is to reduce friction or tissue trauma as the sling 42 is drawn through the various tissues. It is noted that the sheath 44 is a wholly optional element of the present invention. The embodiment of the present invention shown in FIG. 14C is believed to potentially reduce sling assembly component contamination/exposure and wound infection.

Figure 15A:
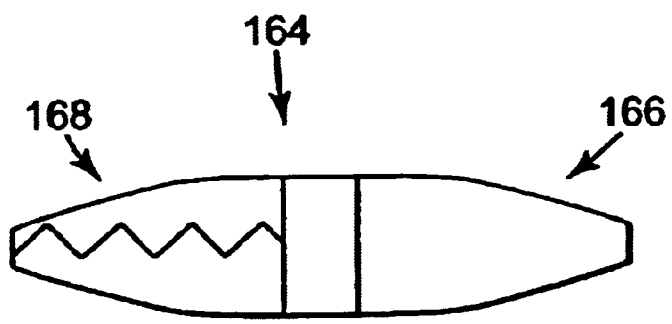
FIG. 15A is a side view of another embodiment of dilator according to another aspect of the present invention.
Figure 15B:
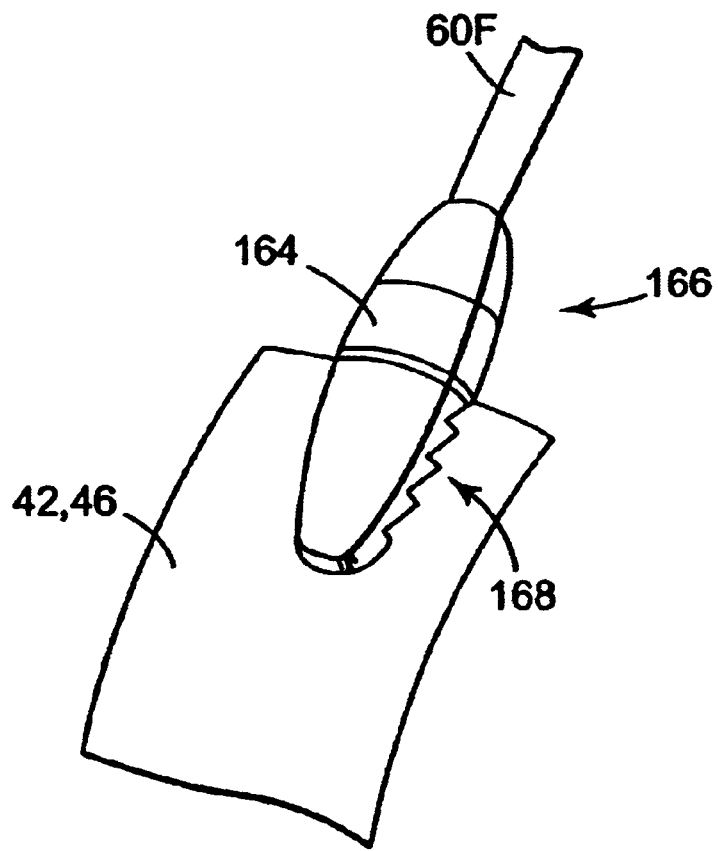
FIG. 15B is a perspective view of the dilator of FIG. 15A showing the dilator attached to a sling or sling assembly.

In an alternate embodiment of the invention, a set of grasping jaws 164 may incorporate a dilator, as shown in FIGS. 15A and 15B. Preferably, the jaws 164 are constructed from a bioabsorbable material. A first end 166 of the jaws 174 attaches to the needle 60 via a snap or quick fitting attachment. A second end 168 of the jaws 164 attaches or clamps onto the sling 42 or sling assembly 46. Optionally, the jaws 164 may serve to anchor the sling 42 within tissue of a patient.

The mechanism by which the jaws 164 attach to and release the sling 42 or sling assembly 46 may be similar to that of a bioptome. Other exemplary mechanisms such as a ball-detent used on a ratchet wrench, spring loaded clamps, memory alloys, and other mechanisms may also be used. The jaws 164 may optionally be operably connected to and controlled by the handle 64 of the device. Manipulation of the handle 64 causes the jaws 164 to open and close, thereby enabling the device to clamp onto and/or release the sling 42 or sling assembly 46. In addition, the handle 64 may be further manipulated to detach the jaws 164 or a portion thereof from the needle 60. As such, once the sling 42 or sling assembly 46 is properly located within the patient (further described below), the bioresorbable jaws 164 are detached from the needle 60 either inside or outside the body of the patient.

Figure 16A:
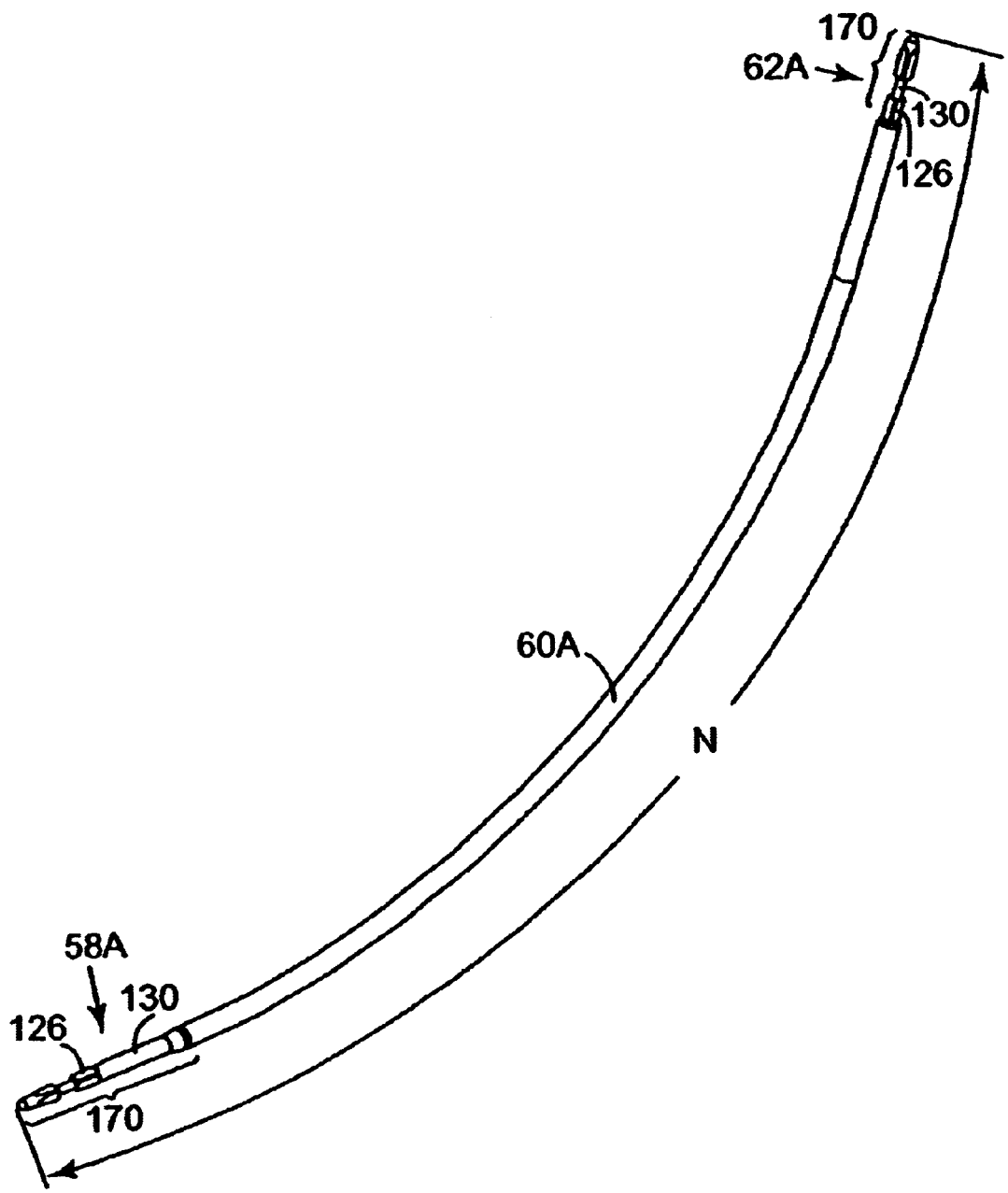
FIG. 16A is a side view of a needle of the present invention.

Referring to FIG. 16A, the needle 60 is generally curved or arcuate. Preferably, the needle is arc-shaped and includes a first end 58 and a second end 62. Although a variety of needle designs and/or configurations may be used including, without limitation, straight, bent, curved, arc-shaped, Stamey, Raz and other configurations, all references hereinafter will be made to an arc-shaped needle in the spirit of brevity and reader convenience.

Overall, the shape of the needle 60 should facilitate and provide controlled passage of the needle 60 through tissue, preferably from an abdominal incision to the vagina or, alternatively, from the vagina to an abdominal incision. The ends or tip of the needle 60 are preferably not sharpened, but may be tapered to afford easy passage through tissue while providing a blunt surface that avoids cutting sensitive tissue such as the bladder or urethra. In a preferred embodiment, the length N of the needle 60 is approximately within the range of 16.5 cm to 24.1 cm (6.5 inches to 9.5 inches) and has a preferred external diameter of approximately 3.175 mm (0.125 inch). It is preferred that the diameter of the needle 60 be small relative to the prior art to reduce tissue trauma.

The needle 60 is made of a malleable, yet durable, biocompatable surgical instrument materials such as, but not limited to, stainless steel, titanium, Nitinol, polymers, plastics and other materials, including combinations of materials. The needle 60 should have sufficient structural integrity to withstand the various forces (e.g. forces caused by dilator attachment, cystoscopy aid passage, and penetration/passage of the needle 60 through the various tissues) without undergoing any significant structural deformation. Optionally, the needles 60 could be sufficiently malleable to allow a practitioner or user of the device to modify the needle 60 to a desired shape and, thereby, optimize the procedural approach.

As shown in the embodiment of FIG. 16A, the first end 58 and second end 62 of the needle 60 may include a keying feature 170 affording secure association between the needle and handle 64 and/or dilator 54 and/or sheath assembly 46. In one embodiment, the keying feature 170 comprises a recess 130 and/or square-shaped portion 126. As previously described, the recess 130 and square-shaped portion 126 are designed for complementary engagement to the appropriate end of a dilator 54 or handle 64. Another embodiment of the invention includes a reversible keying feature. The reversible keying feature allows the handle 64 to be interchangeably attached yet securely affixed to either end of the needle 60. In a preferred embodiment, the needle 60 may be substantially symmetric about a centerpoint, that is, the radius of curvature of the needle 60 may be substantially constant and either a handle or a dilator may be attached to either end of the needle 60.

Figure 16D:
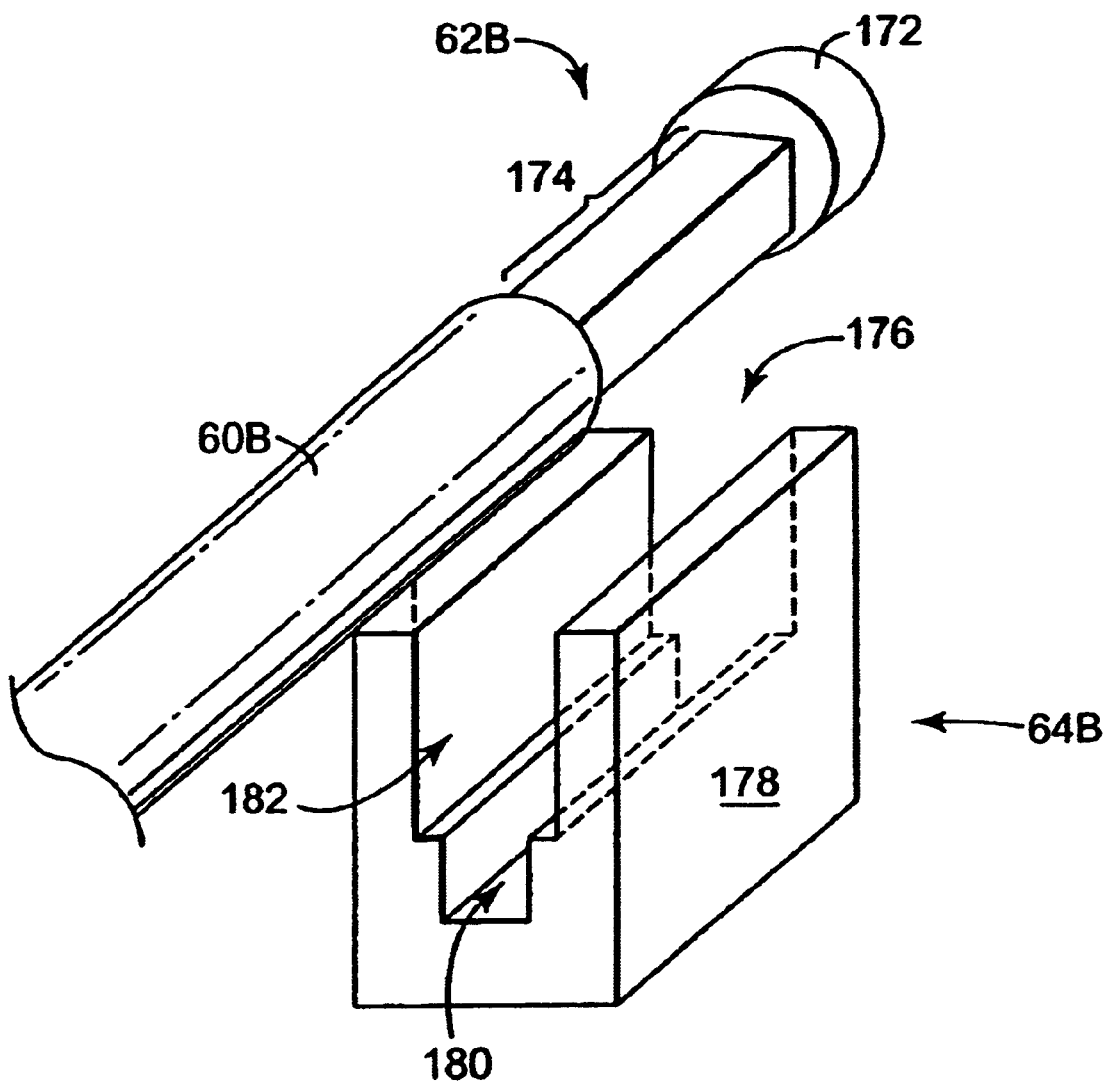
FIG. 16D is a perspective view of an end portion of a needle according to an aspect of the present invention.
Figure 16F:
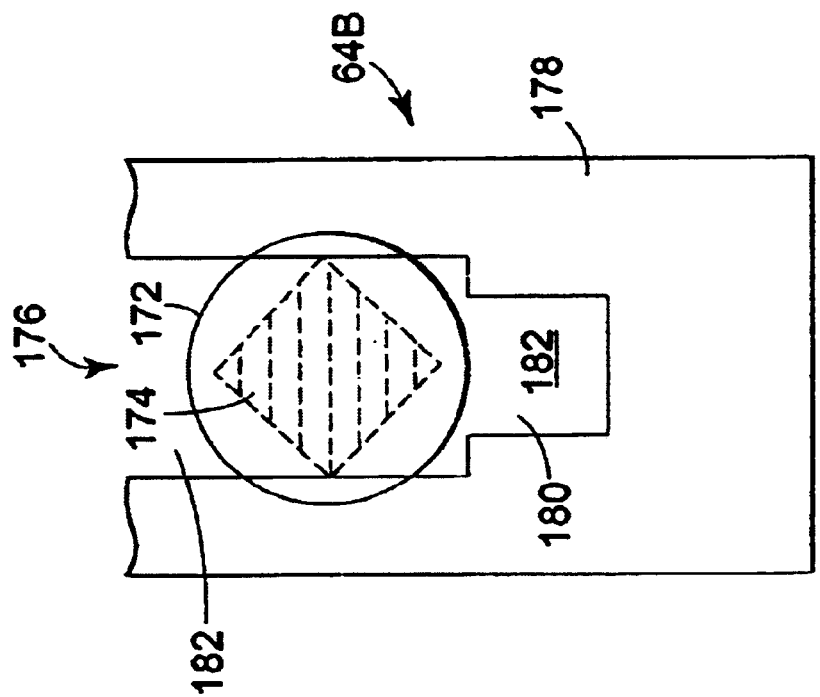
FIG. 16F is an end view of a needle in a seated position.
Figure 16E:
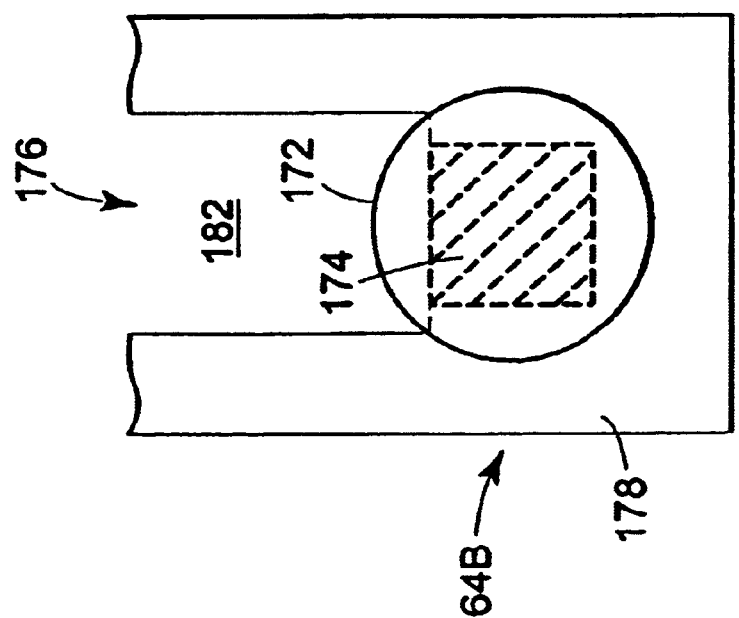
FIG. 16E is an end view of a needle in an unseated position.

In an alternate embodiment, the keying feature of the needle 60B comprises an end cap 172 and an elongate reduced width segment 174 having a square-shaped cross sectional profile, as shown in FIGS. 16B to 16D. The second end 62B of the needle 60 shown in these FIGS. is inserted into the keying feature or channel 176 that extends along the longitudinal axis of the handle 64B (partially shown in FIGS. 16D to 16F). When the needle 60B is properly positioned within the handle 64B, a yoke or other fastening component 178 receives and secures the elongate segment 174 in the narrow portion 180 of the channel 176, as shown in FIGS. 16D and 16E. The complementary configuration of the channel's narrow portion 180 and the needle's elongate segment 174 prevents the handle 64B from rotating around the axis of the needle 60B. In addition, this configuration may also provide additional needle/handle stability and improved tactile feedback for a user of the device.

The present invention may optionally include structure that allows the surgeon to change the orientation or position of the handle relative to the needle. The handle may be rotatably repositioned relative to the needle or, in some embodiments, the handle may be axially slidable and repositionable along the length of the needle. The handle may be repositioned in any orientation as determined by the surgeon or it may be indexed between a plurality of predetermined orientations depending on the particular embodiment of the present invention.

FIG. 16E illustrates the needle seated in a locked position relative to handle 64B. In order to rotate the handle 64B, a user or practitioner manipulates a trigger or button that actuates the fastening component 178 thereby causing the channel 176 to disengage from the elongate segment 174, as shown in FIG. 16F. In this position, segment 174 of the needle 60B is no longer seated in the handle 64B. With the elongate segment 174 positioned in the wider portion 182 of the channel 176, the needle 60B is free to rotate. However, the configuration of the needle's end cap 172 prevents the needle 60B from becoming completely disengaged from the handle 64B. Thus, the keying features maintain the needle 60B in proper alignment with the handle 64B when in the locked position and also allow a user to controllably rotate the needle 60B to obtain a desired handle 64B orientation.

Figure 17A:
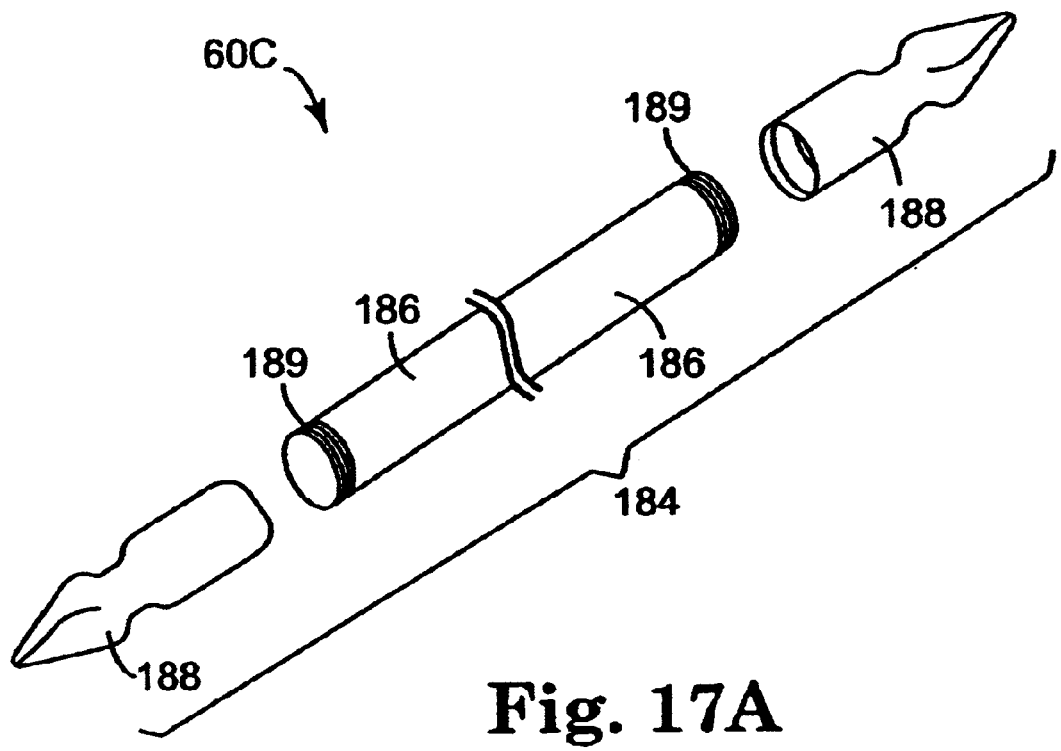
FIG. 17A is a perspective view of another embodiment of the needle of the present invention.
Figure 17B:
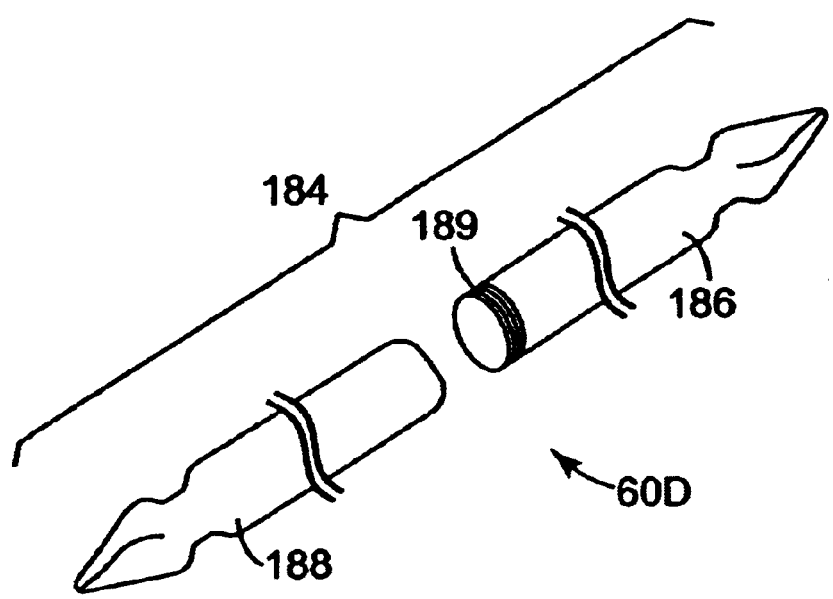
FIG. 17B is a perspective view of another embodiment of needle according to the present invention.

In an alternate embodiment of the invention, the needle 60C comprises an assembly 184 having one or more detachable components. For example, referring to embodiments shown in FIGS. 17A and 17B, the needle assembly 184 comprises a body portion 186 and one or more segments 188. An external thread 189 formed near the end of the body portion 186 allows needle segments 188, dilators 54, slings 42, or sling assembly 46 to be screwed onto the body portion 188 thereby forming the needle assembly 184. In addition, the devices may be easily removed by simply unscrewing them from the body portion 186 of the needle assembly 184. Other configurations or designs of the needle assembly 184 may include, but are not limited to, hollow or solid body portions 186, snap fit, memory alloy or latching mechanisms, internal threading or other designs.

In another embodiment, the handle 64 may be permanently attached to an end 62 of the needle 60. More particularly, the handle 64 may be rigidly affixed to the needle 60 so that substantially no relative movement may occur between the needle 60 and the handle 64.

Figure 18A:
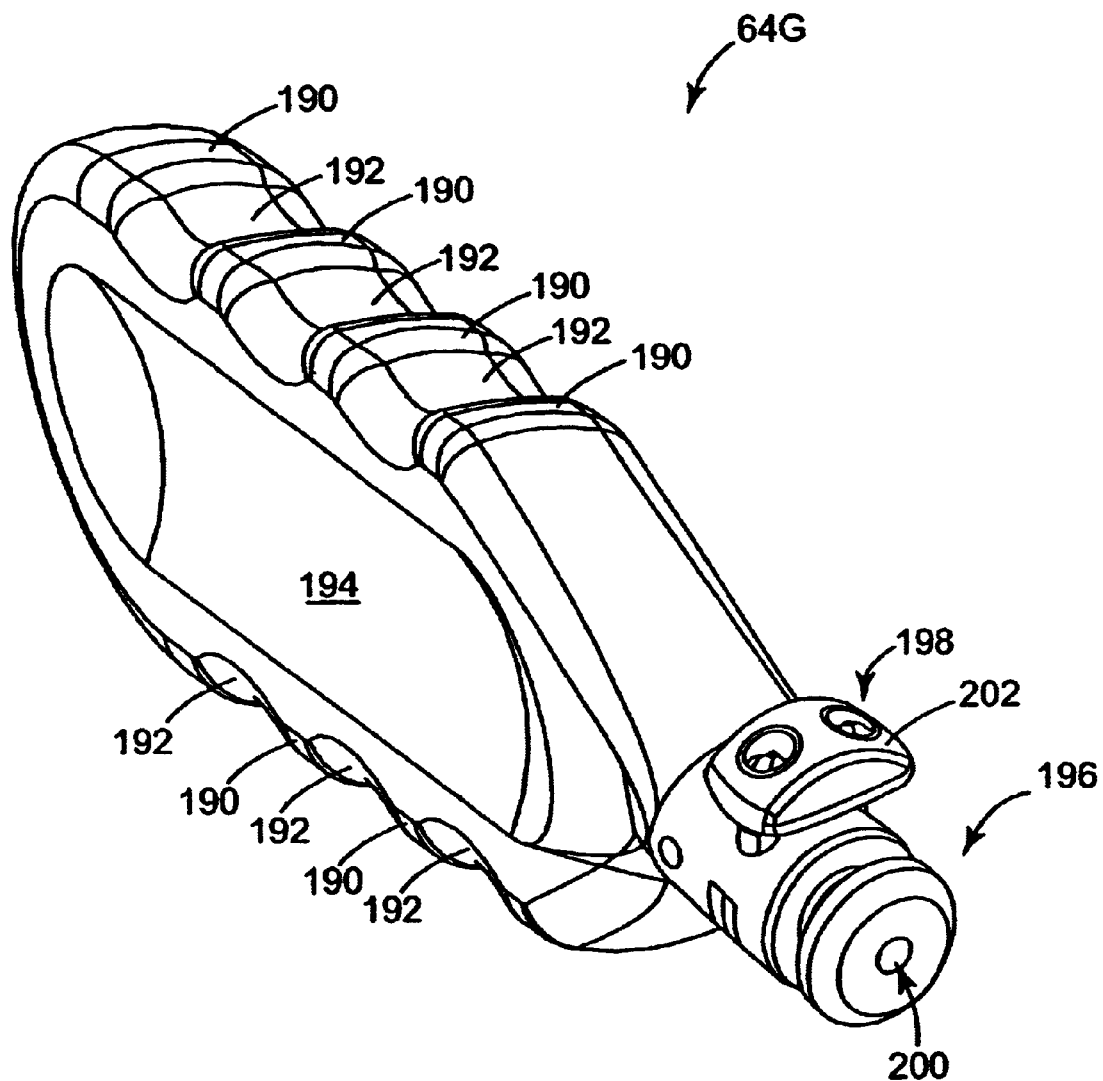

Referring to FIG. 18A, one embodiment of the adjustable handle 64G comprises a relatively smooth, ergonomic body made of delrin, ABS, nylon, polycarbonate, acetal, polyetherimide, polysulfone or other sterilizable materials. The body of the handle 64G may be hollow, solid or semi-solid. One or more surfaces of the handle include a plurality of ridges 190 and/or indentations 192 that provide an enhanced gripping surface for a user of the device. Alternatively, various portions of the surface of the handle 64G may also include grasping features such as bumps, grooves, ridges or other gripping means, that enable improved manipulation of the handle 64G. In addition, the handle 64G may include an indentation formed near the middle 194 of the handle 64G that provides a user of the device with better control of, and an improved grip on, the handle 64G.

Figure 18B:
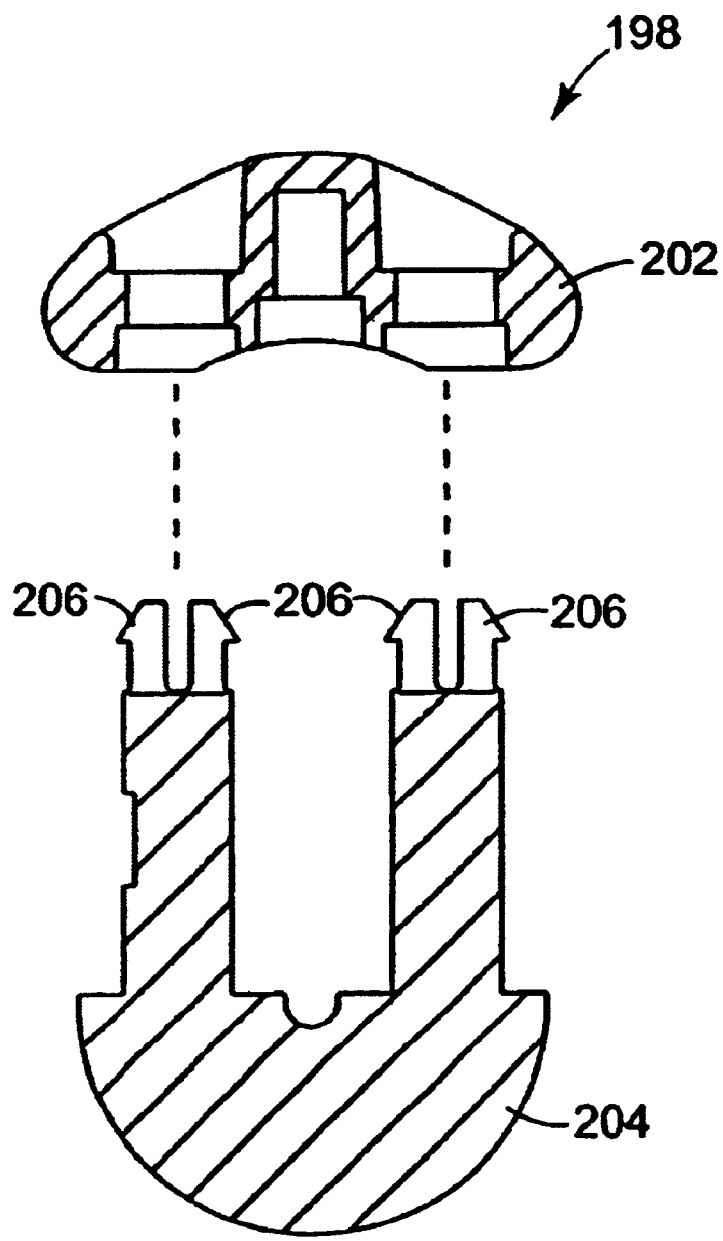
Figure 18C:
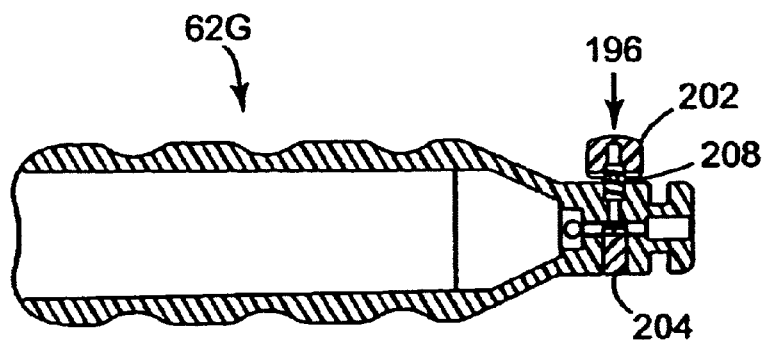

A push button 198 and keyed opening 200 are located near the needle attachment end 196 of the handle 64G shown in FIG. 18A and form a keying feature of the handle 64G. As shown in FIG. 18B, the push button assembly 198 comprises a button or knob-shaped component 202 that attaches to a yoke 204 (attachment locations indicated by dashed reference line). In particular, the yoke 204 is attached to the button 202 via snap tongs 206 that lock the button 202 and yoke 204 together. Prior to attachment, the button 202 and yoke 204, including a spring 208, are fitted within their respective grooves and/or slots formed near the needle attachment end 196 of the handle 64G, as generally shown in FIG. 18C. The spring 208 provides the appropriate tension to maintain the assembly in a locked position.

Figure 18D:
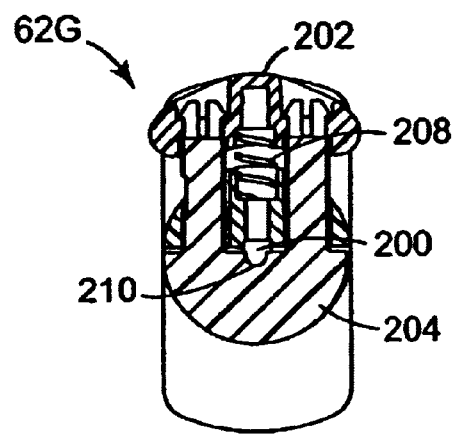
Figure 18E:
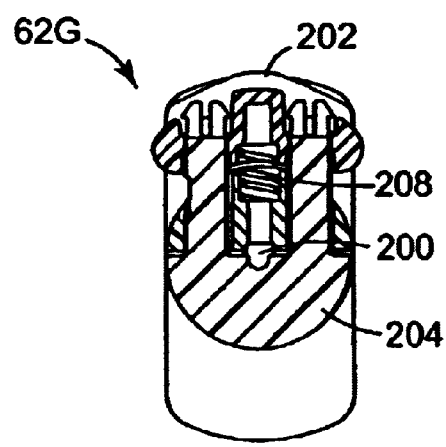

When the assembly is in a locked position (shown in FIG. 18D), the spring forces push the button 202 in a direction away from the longitudinal axis of the device. This in turn causes the groove or recess 210 of the attached yoke 204 to protrude within the keyed longitudinal opening 200 resulting in a non-square-shaped opening formed along an axial portion near the needle attachment end of the handle 64G. In the locked configuration, the handle 64G is securely attached in a stationary position on the needle 60. Pressing or pushing the button 202 inwardly toward the axis of the device unlocks the device and creates a square-shaped or keyed opening 200 for the needle 60. FIG. 18E illustrates a cross-section of the keyed, longitudinal opening 200 in an unlocked position.

The quick-release push button of the handle 64G enables a user of the device to easily attach or detach the handle 64G from the needle 60 or reposition the orientation of handle 64G relative to the needle 60, using one hand. While gripping the handle 64G, the user of the device simply depresses the push button 202 with one finger to unlock the handle. Still using a single hand to control the handle 64G, the user can then insert one end of the needle 60 into the keyed opening 200 of the handle 64G and, upon releasing the button 202, secure the handle 64G to the needle 60.

As previously disclosed, the needle 60 includes a similar keying feature configured for complementary engagement with the keyed portion of the handle 64G. These complementary, square-shaped keying features allow a practitioner or user of the device to rotatably index the handle 64G between predetermined positions located in ninety-degree increments around the needle axis. Thus, the practitioner may position the handle 64G in a preferred configuration on the needle 60 that provides the greatest comfort and ease of insertion. In addition, via the locking mechanism, the keying features also prevent the handle 64G from uncontrollably rotating around the axis of the needle 60, for instance, during a sling or needle insertion procedure. Although the invention has been described with respect to a square-shaped keying feature, other geometrical configurations and keying means are also included within the scope of the present invention.

Figure 19A:
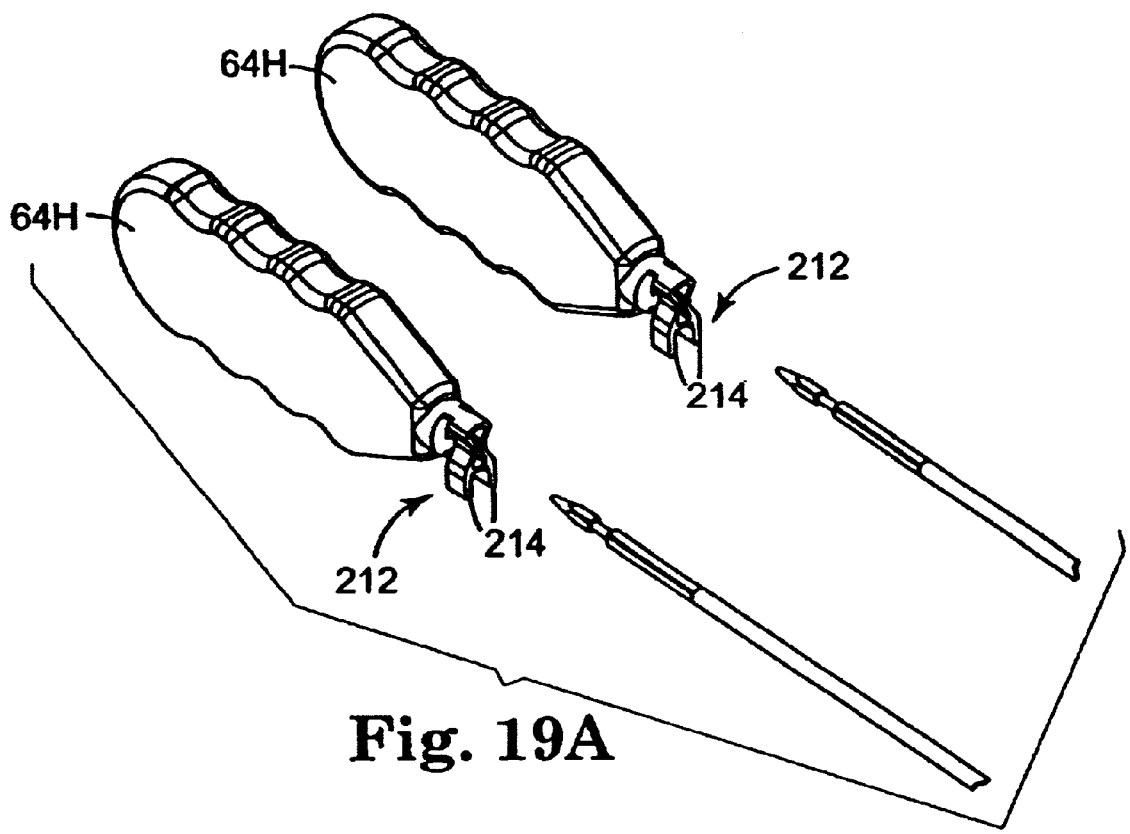
FIG. 19A is a perspective view of another embodiment of the handle of the present invention, showing two handles and portions of mating needles.
Figure 19B:
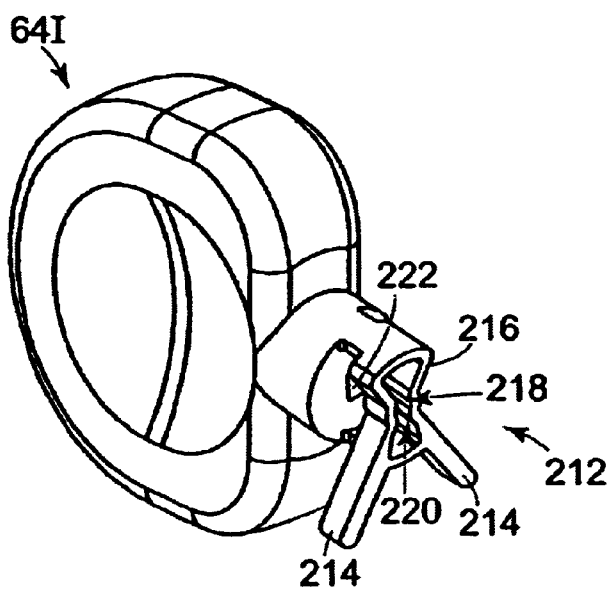
FIG. 19B is a perspective view of another embodiment of handle according to the present invention.
Figure 19C:
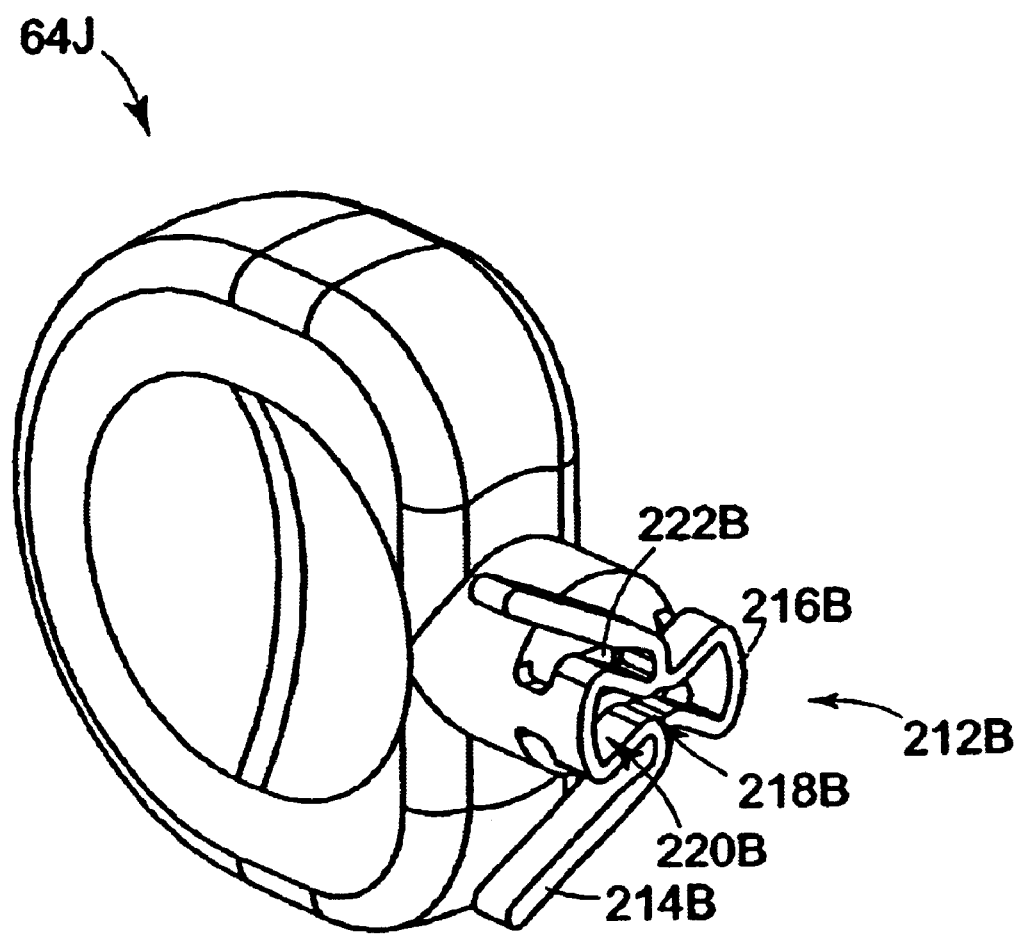
FIG. 19C is a perspective view of another embodiment of handle according to the present invention.

Another embodiment of needle attachment mechanism for a handle is shown in FIGS. 19A to 19C. The handle 64H includes a quick-release feature 212 comprising one or more levers 214 and an associated border or frame 216 that surrounds an opening 218. The opening 218 is generally located near the needle end of the handle 64 and along the longitudinal axis of the device. The frame 216 bordering the opening 218 may include various indentations or ridges 220 that provide improved gripping capabilities. In addition, the handle may also include a square-shaped keying feature 222 similar to the previously described keying features. A different shaped handle 64I is shown in FIGS. 19B and 19C.

During use, a practitioner or user of the device simply compresses the levers 214 of the handle 64H together using, for example, a thumb and forefinger. Compression of the levers 214 changes the configuration of the frame 216 and opening 218 to allow insertion of a needle 60 therein. The user of the device releases the levers 214 when the needle 60 is properly positioned within the handle 64I, causing a portion of the frame 216 to compress against a portion of the needle 60 (e.g., a recessed portion) thereby blocking axial movement of the needle relative to the handle 64I and securely attaching the handle 64I onto the needle 60. The handle 64I can be quickly released from the needle 60 by pressing on the handles 214.

Figure 20A:
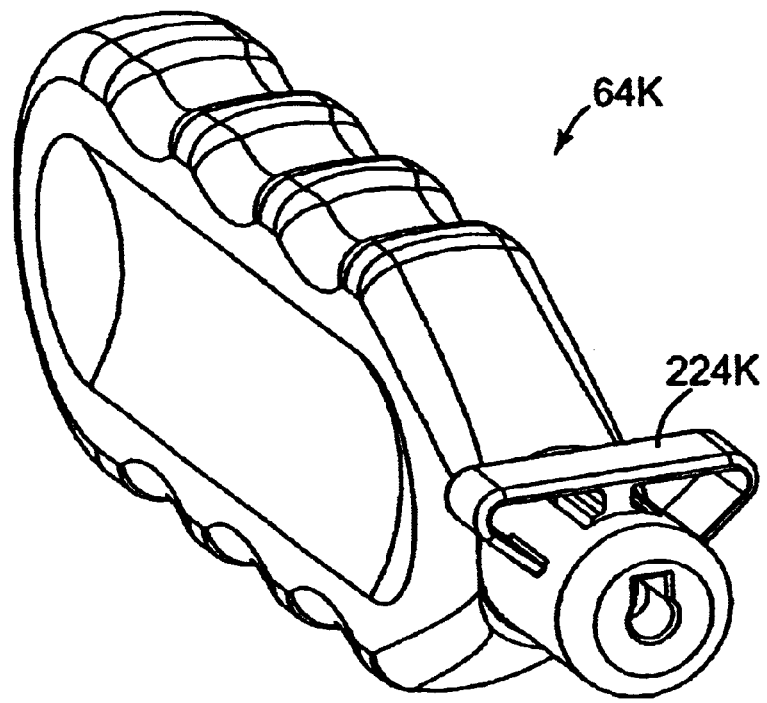
FIG. 20A is a perspective view of another handle according to the present invention.
Figure 20B:
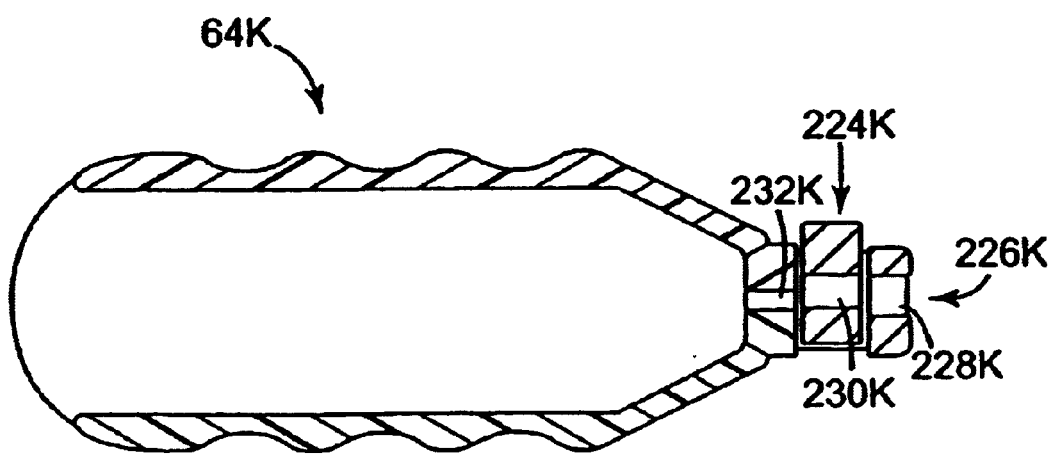
FIG. 20B is a sectional view of the handle of FIG. 20A.
Figure 20C:
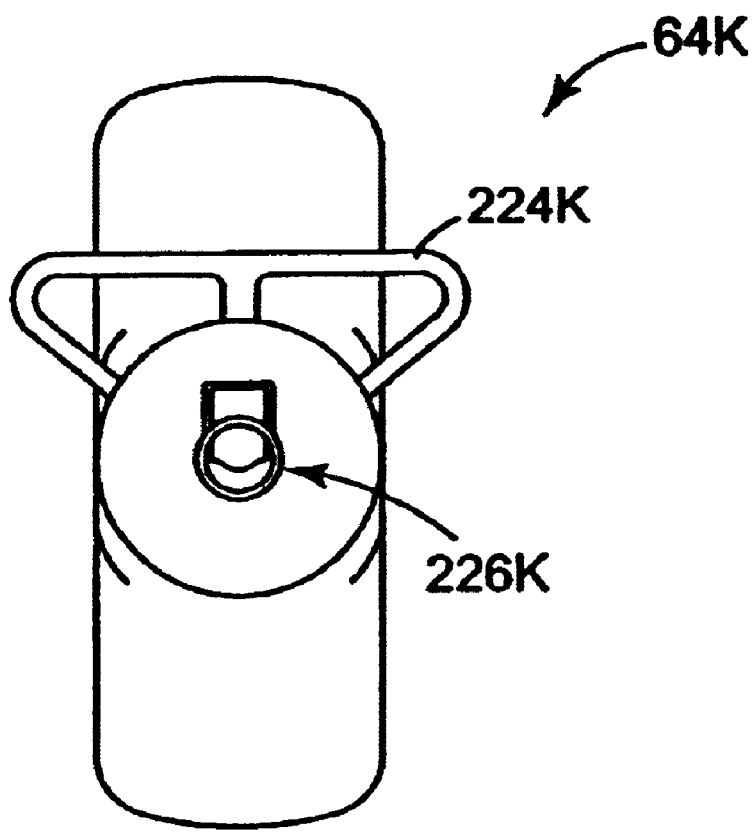
FIG. 20C is an end view of the handle of FIG. 20A.

Another embodiment of a quick-release feature for the handle 64K is shown in FIGS. 20A–20C. For this embodiment of the invention, the handle 64K may be made from a single molded or machined component. A quick-release button 224, located near the needle end of the handle 64K, controls a keyed needle-latching mechanism 226. As best seen in FIG. 20B, the needle latching mechanism 226 generally includes a geometrically shaped opening section 228, a locking section 230 and an end section 232. When a practitioner or user of the device depresses the quick-release button 224, the semi-resilient material of the handle 64K causes displacement of the locking section 230, thereby allowing the needle 60 (not shown) to be inserted into the latching mechanism 226 of the handle 64K. After the needle 60 and handle 64K are positioned or aligned according to user preference, the button 224 is released causing the locking section 230 to return to its initial configuration and, in so doing, seat within the complementary, recessed feature of the needle 60. This not only secures or locks the handle 64K onto the needle 60 but also prevents the handle 64K from rotating around the needle axis.

In another embodiment of the invention, the keyed, locking portion and/or quick release feature of the handle 64K may be located near the middle of the handle 64K, near the end of the handle 64K close to the needle (FIG. 18A) or at any preferred location on the handle 64K. A large or small section or length of the needle 60 may be housed within and contact the handle 64K of the device, thereby providing enhanced user-control and stabilization of the needle 60 relative to handle 64K. The increased surface contact between the needle 60 and handle 64K may also strengthen the associated gripping or frictional forces, resulting in improved locking or attachment capabilities of the device.

Figure 21A:
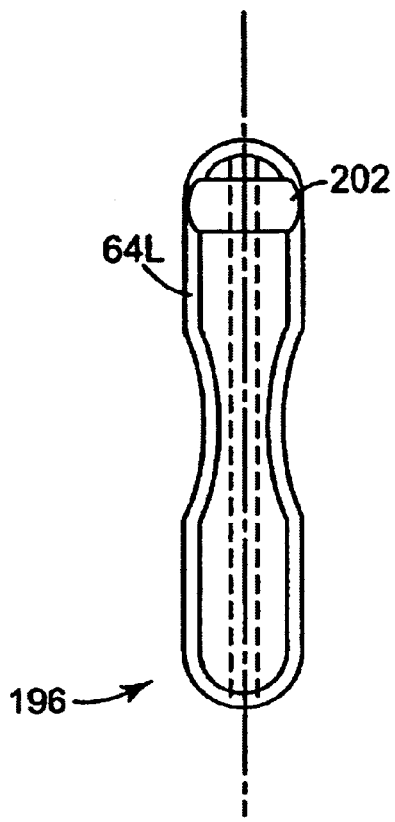
FIG. 21A is a side view of another embodiment of the handle of the present invention.
Figure 21B:
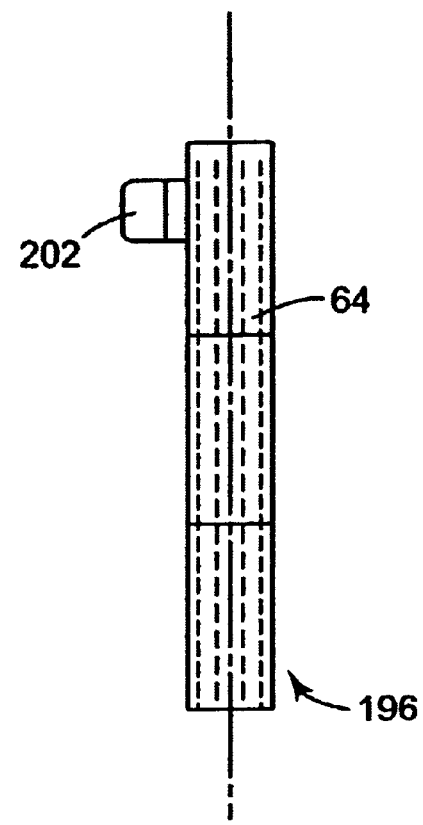
FIG. 21B is another side view of another embodiment of handle according to the present invention.

The associated quick-release feature (such as push button 198, button 224, levers 214, etc.) may also be positioned at any preferred location on the handle 64 of the present invention. For example, referring to FIGS. 21A and 21B, positioning the button 202 opposite to the needle insertion end 196 of the handle 64L may reduce or prevent accidental triggering of the button 202. Further, this particular design may provide additional ergonomic advantages for the user of the device. For example, the bottom could be flush or recessed with the surface of the handle.

Various configurations of the overall size, weight and shape of the handle 64 are also included within the scope of the claimed invention. Still referring to FIGS. 21A and 21B, another embodiment of the handle 64L comprises a compact profile. The smaller size of the handle 64L reduces the weight of the handle 64L, thereby making the device 40 less heavy at the top and better balanced. Alternatively, the handle 64L may also be configured to be permanently, but rotatably, affixed to the needle 60 (not shown). As such, the user or practitioner may rotate the handle 360° around the axis of the needle 60 and lock the handle 64L in position once the desired orientation is reached.

Figure 11:
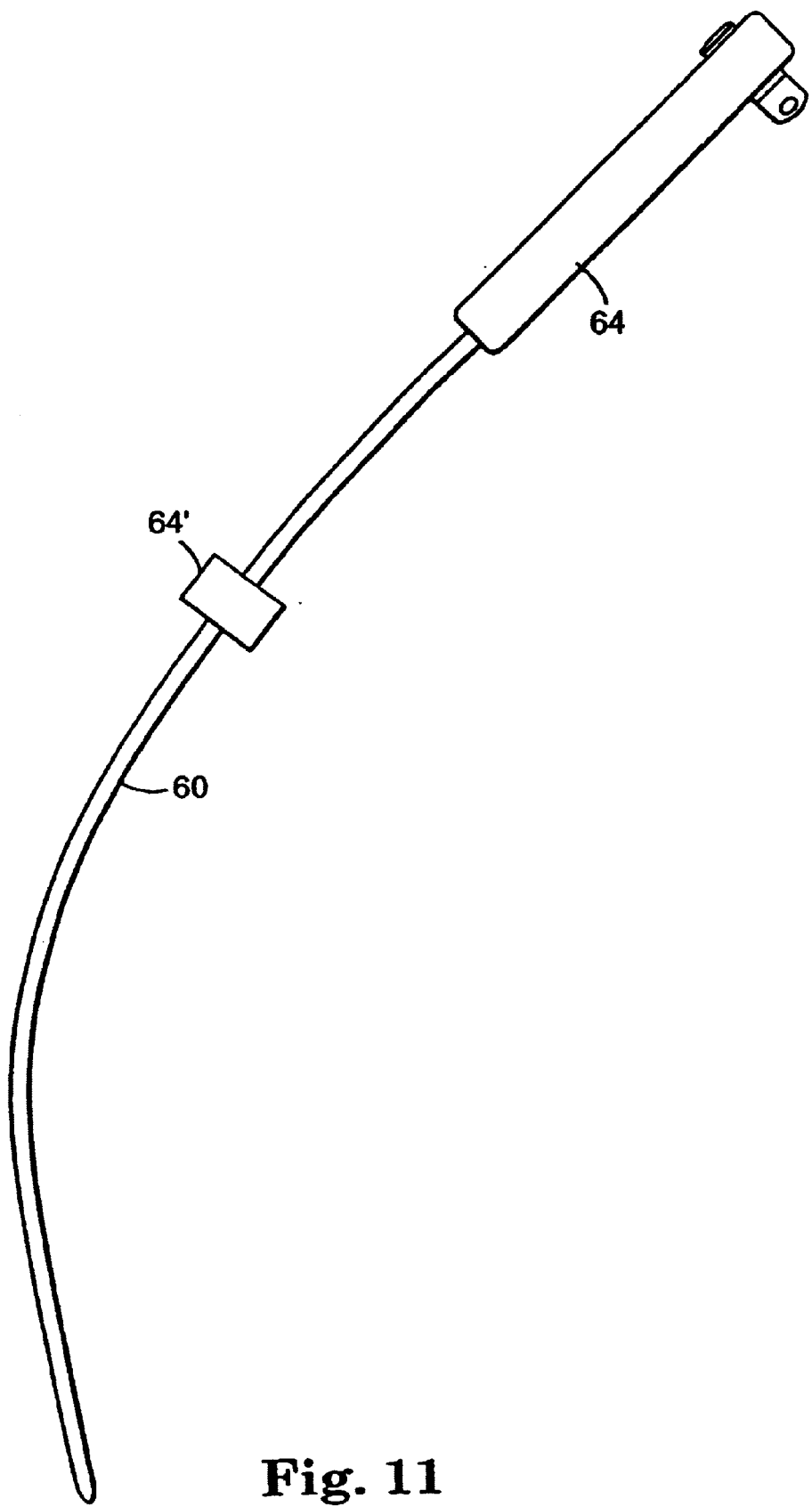
FIG. 11 is a side view of an embodiment of needle, handle and slidable handle according to an aspect of the present invention.

FIG. 11 illustrates an alternate embodiment of the present invention that includes a slidable second handle 64' which may be used alone or in combination with handle 64. In general, the slidable handle may provide additional ergonomic advantages and control during the needle insertion procedure. For example, when used in combination with the handle 64, the slidable handle 64' is initially positioned and optionally locked near the first end 58 of the needle 60. During needle insertion (further described below), the slidable handle allows the user or practitioner to maneuver the needle 60 more accurately along the insertion pathway. In the example of an initial suprapubic approach, after the slidable handle 64' comes close to or in contact with the abdomen, the slidable handle 64' is unlocked and repositioned closer to the handle 64. The slidable handle is then secured at the new position and locked in place, thereby allowing further insertion of the needle 60.

The second handle 64' may optionally be locked in a position that blocks inadvertent lurching of the needle 60 within the tissue. Preferably, the second handle 64' is sized and shaped to engage the abdominal tissue to act as a stop to prevent further penetration of the needle 60 until the second handle 64' is unlocked and moved to a location closer to the handle 64. This feature is believed to be useful in resisting uncontrolled passage of the needle 60 into the retropubic space after the end 58 of the needle 60 bursts through the tough rectus fascia. Once the rectus fascia is penetrated, the second handle 64' is unlocked and moved to a location closer to the handle 64 and the needle can be controllable passed through tissue.

Optionally, the second handle 64' may include means for affording sliding of the handle 64' toward the handle 64, but that resists movement of the handle 64' away from the handle 64. The means may comprise a plurality of ribs within handle 64' that engage the needle 60 and that are angled toward the handle 64.

Figure 22A:
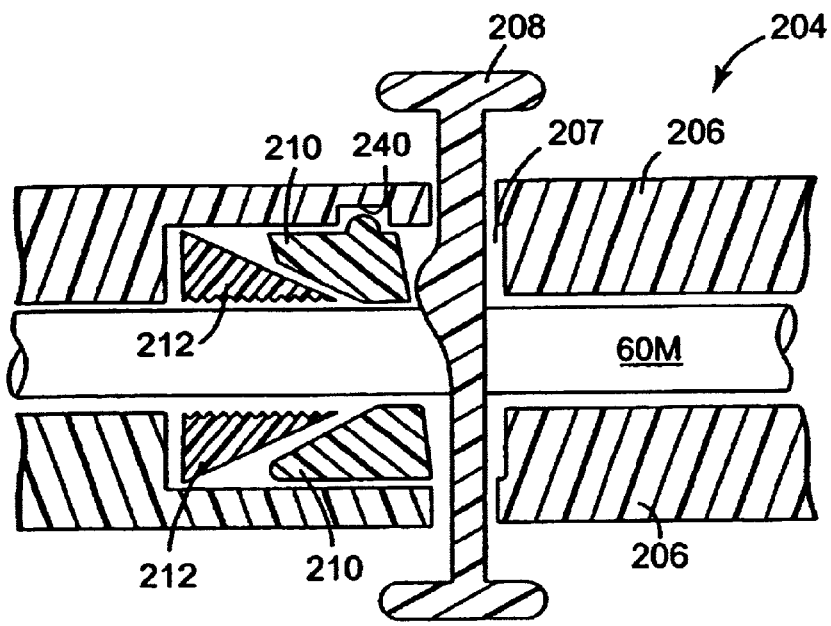
FIG. 22A is a side schematic illustration of one embodiment of a slidable handle and locking mechanism of the present invention.
Figure 22B:
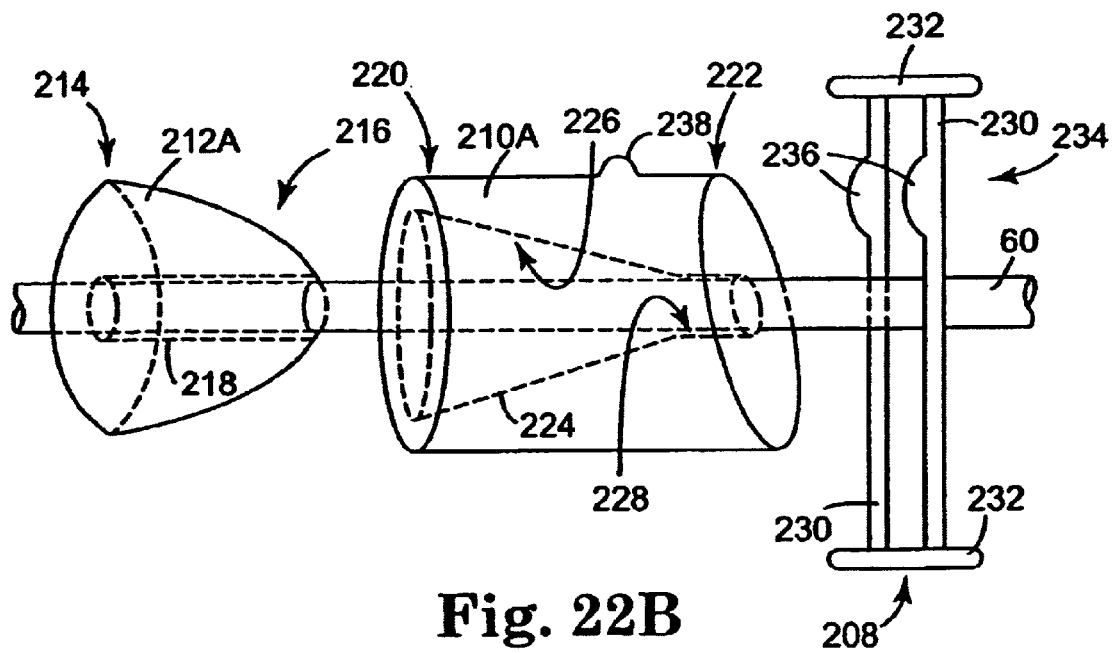
FIG. 22B is a schematic illustration of the slidable handle of FIG. 22A.

Referring to another embodiment shown in FIGS. 22A and 22B, a slidable handle 204 comprises a body portion 206 (partially shown in FIGS. 22A and 22B), latch 208, o-ring 210 and spring ring 212 contained in a handle cavity 207. In general, the body portion 206 and latch 208 may be made of delrin, ABS, nylon, polycarbonate, acetal, polyetherimide, polysulfone, or other sterilizable materials. In addition, the o-ring 210 and spring ring 212 may be made from high durometer polyurethane, teflon and other rigid or semi-rigid materials.

The frustro-concially shaped spring ring 212 comprises a first end 214, a second end 216 and a lumen 218. In general, the external diameter of the first end 214 of the spring ring 212 is greater than the external diameter near the second end 216 of the spring ring 212, thereby forming an inclined surface. The lumen 218, situated along the axis of the spring ring 212, is configured to slidably engage a needle 60.

Located adjacent to the spring ring 212 is a frusto-cylindrically shaped o-ring 210. The o-ring 210 comprises a first end 220, a second end 222 and a lumen 224 having a first surface 226 and a second surface 228. The first surface 226 of the lumen 224 is located near the first end 220 of the o-ring 210 and forms an incline configured for complimentary engagement with the inclined surface of the spring ring 212. In contrast, the second surface 228 of the lumen 224 is located near the second end 222 of the o-ring 210 and is designed to slidably engage the needle 60.

Adjacent to the o-ring 210 is a latch 208 comprising two posts 230 and two tabs 232, wherein similar ends of each post 230 are attached to a tab 232. In addition, the posts 230 border the needle 60 in perpendicular alignment with the needle axis, thereby forming, together with the tabs 232, a frame around a portion of the needle 60. One end 234 of each post 230 also includes a flange 236 that triggers the locking mechanism of the handle 204. The handle 204 is locked onto a needle 60 by depressing a tab 232 so that the flange 236 contacts a portion of the o-ring 210 and causes the o-ring 210 to engage the spring ring 212. The force of the o-ring 210 against the spring ring 212 compresses the longitudinal length and causes radial expansion and compression of the spring ring 212, thereby generating frictional forces among the spring ring 212, needle 60 and handle cavity 207. These frictional forces prevent needle movement in the longitudinal direction (i.e. along the needle axis). To prevent handle 204 rotation on the needle 60, a projection 238 may be formed on an external surface of the o-ring 210 and configured for complimentary engagement with an indentation 240 formed on an internal surface of the handle 204. Further, the handle 204 may be unlocked in a similar fashion by simply depressing the other tab 208 and, thereby, releasing the compressive forces which causes the components to disengage.

FIG. 22B illustrates an embodiment of lockable handle similar to that of FIG. 22A. Elements in FIG. 22B have been given reference characters similar to those of FIG. 22A, to which the suffix "B" has been added.

Figure 23A:
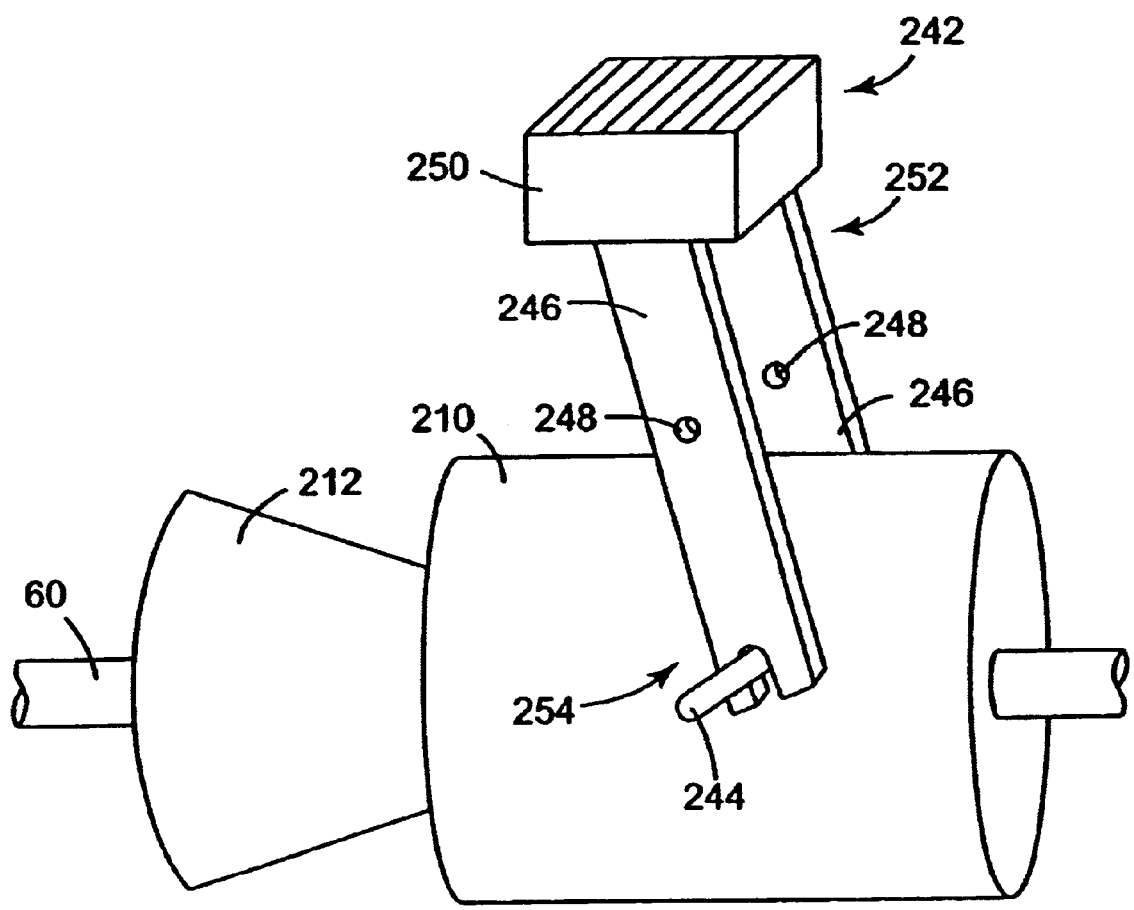
FIG. 23A is a schematic perspective view of another embodiment of slidable handle and locking mechanism of the present invention.
Figure 23B:
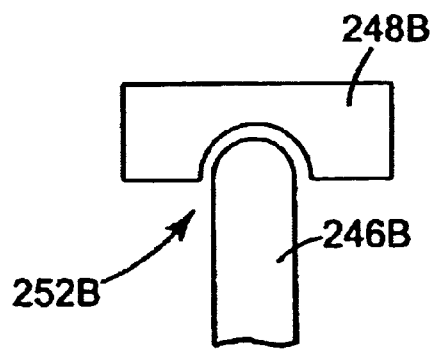
FIG. 23B is a schematic view of portions of the slidable handle and locking mechanism of FIG. 23A.
Figure 23C:
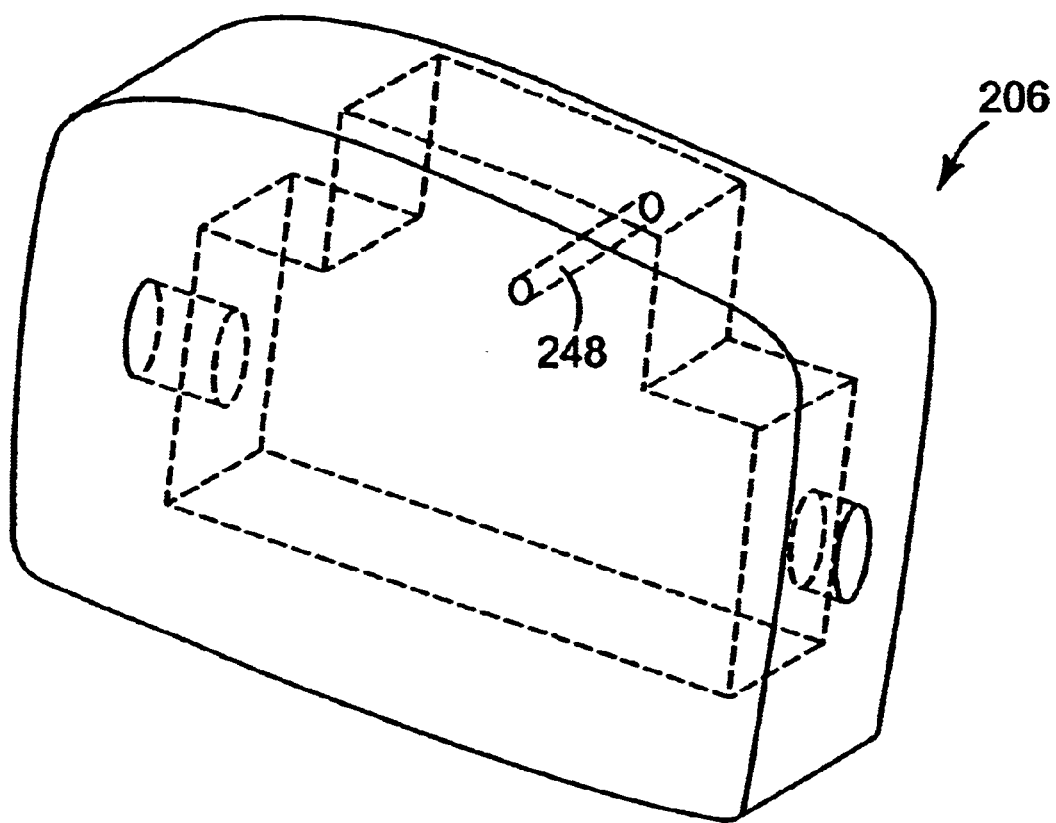
FIG. 23C is a perspective view of a portion of the handle of FIG. 23A.

Referring to FIGS. 23A–23C, an alternate embodiment of the slidable handle comprises a body portion, o-ring 212, spring ring 210 and slider 242 contained in a handle cavity. The o-ring 210 and spring ring 212 of this embodiment of the slidable handle 204 are similar to those previously described. However, the cylindrically shaped o-ring 210 includes at least one rod 244 extending perpendicular to the needle axis and partially projecting from the cylindrical surface of the o-ring 210.

The slider 242 of the handle 204 comprises two shafts 246, that pivot on a rod (not shown) about a pivot point 248, and a switch 250. In general, the shafts 246, switch 250 and rod 244 may be made from substantially the same materials, such as delrin, ABS, nylon, polycarbonate, acetal, polyetherimide, polysulfone or other similar materials. The first end 252 and second end 254 of each shaft are configured to securely engage the switch 250 and rod 244, respectively, thereby forming the slider assembly. The slider 242 in combination with the o-ring 219 and spring ring 212 are the mechanisms by which the needle 60 and handle 204 may be locked and unlocked.

For example, a user locks the handle 204 by pushing or pressing the switch 250 in one direction. This action causes the shafts 246 to move the o-ring 210 into complementary engagement with the spring ring 212. As previously described, the resulting frictional forces prevent linear displacement of the needle 60, thereby securely locking the handle 204 onto the needle 60. The handle 204 may be unlocked by simply pushing the switch 250 in the opposite direction.

In another embodiment, shown in FIGS. 24A–24D, the slidable handle comprises a body portion 206, upper block 256, lower block 258, load distributor 260 and force providing member 262 (e.g. a cam). The body portion 206 of the handle 204 may be made of materials similar to those described in previous embodiments. In addition, the lower and upper blocks 258, 256 may be made of high-density polyurethane, whereas the load distributor 260 and force providing member 262 may be made of a material with a high coefficient of friction.

Figure 24A:
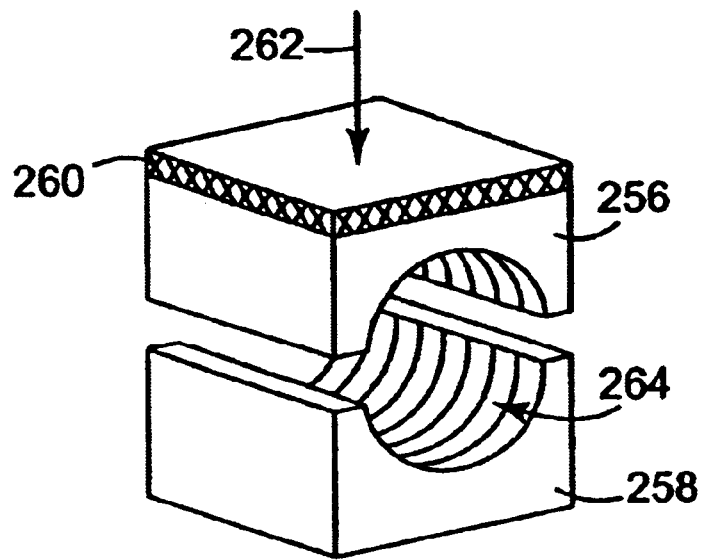
FIG. 24A is a perspective view of another embodiment of a slidable handle and locking mechanism of the present invention.
Figure 24B:
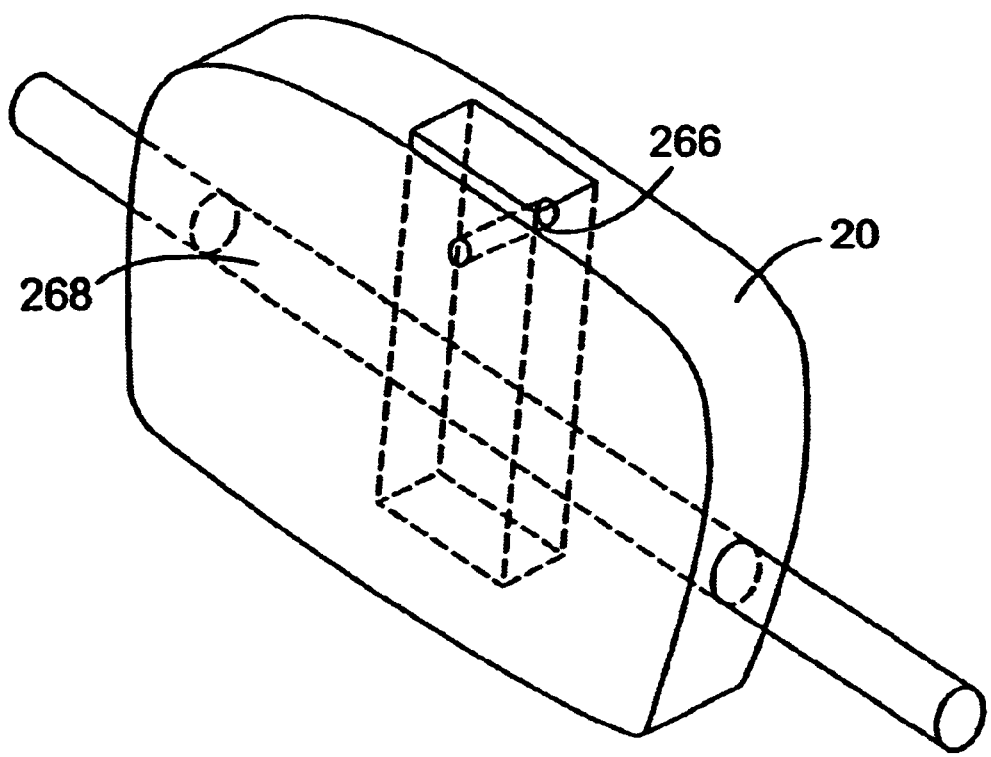
FIG. 24B is a schematic perspective view of portions of the handle introduced in FIG. 24A.
Figure 24C:
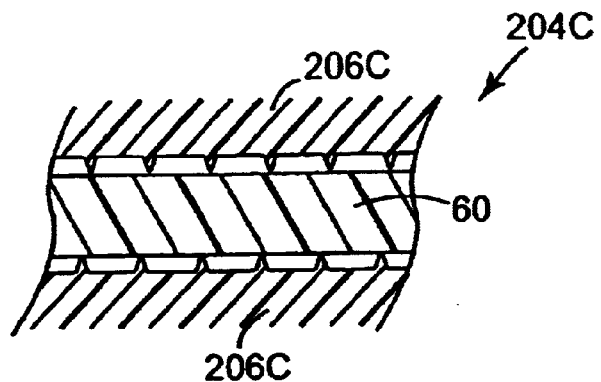
FIG. 24C is a sectional view of elements of another handle according to the present invention.

Referring to FIGS. 24A–24C, the generally square-shaped blocks 256, 258 include a channel 264 formed within a portion of each block. The channels 264 are configured to house a needle 60 when the blocks 256,258 are properly aligned within the handle body 206. In addition, ridges, bumps, or other similar gripping features are formed on the surface of each channel 264 to enhance the needle gripping capabilities of the blocks 256,258.

Figure 24D:
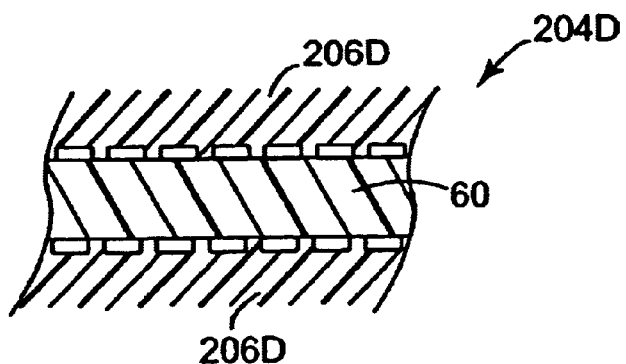
FIG. 24D is a sectional view of elements of another handle according to the present invention.
Figure 24E:
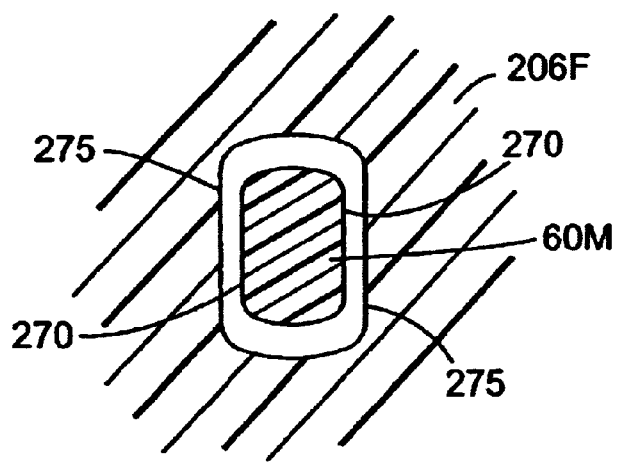
FIG. 24E is a sectional view of elements of another handle according to the present invention.

The handle of FIGS. 24A–24E locks onto a needle 60 by depressing the force providing member 262. The force providing member 262 forces the upper block 256 into close proximity with the lower block 258, subsequently compressing or sandwiching the needle 60 therebetween. The compression forces, which are evenly displaced via the load distributor 260, together with the gripping surfaces of the blocks 256,258 prevent linear displacement of the needle 60 relative to the handle when locked within the handle body 206, as shown in FIG. 24D. Although the gripping features should sufficiently prevent the handle body 206 from rotating about the needle axis, additional keying features may also be added. For example, the needle 60 and needle lumen 268 of the handle body 206 may include complementary features, such as flattened surfaces 270 shown in FIG. 24E, that provide added stability to the present invention.

Figure 25:
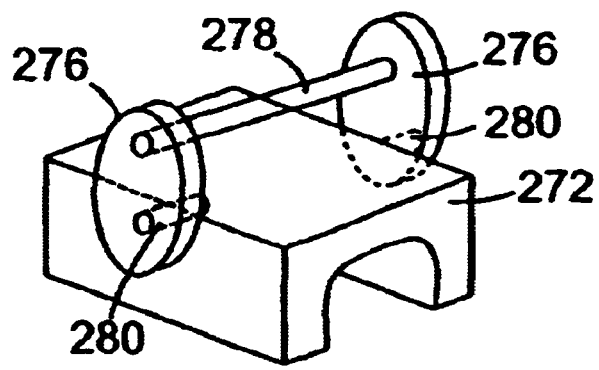
FIG. 25 is a schematic perspective view of elements of another handle according to the present invention.

Referring to FIG. 25, an alternate embodiment of the locking mechanism of the slidable handle 204 comprises an upper clamping block 272, lower block (not shown), two cams 276, a rod 278 and two pins 280. The needle is designed to be placed between the upper and lower blocks and sandwiched therebetween. Rotation of the wheel cams 276 provide balanced pressure on clamping block 272.

Figure 26:
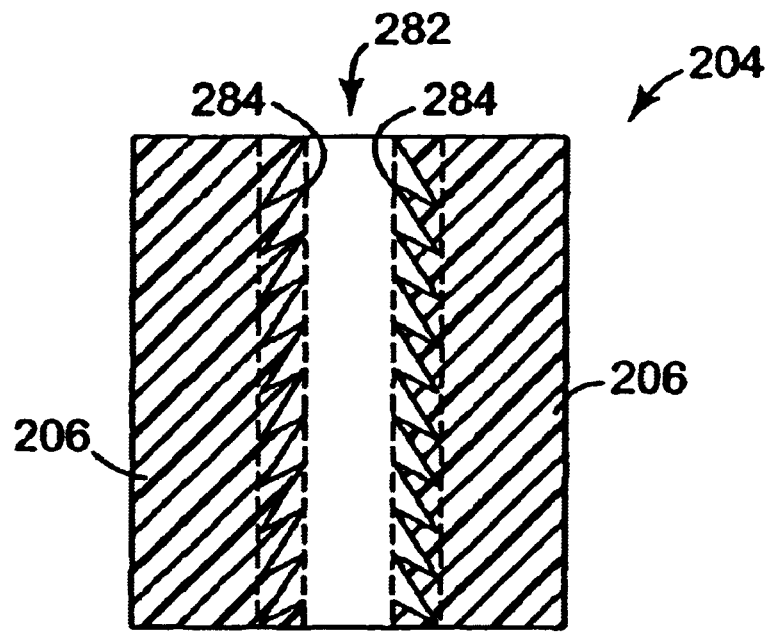
FIG. 26 is a sectional view of another embodiment of a slidable handle and locking mechanism of the present invention.

In another embodiment of the present invention, the slidable handle 204 comprises a body portion 206 and locking mechanism 282. The body portion may be made from silicone rubber or other elastomeric materials. As shown in FIG. 26, the body portion 206 includes a barbed inner lumen 284 that functions as the locking mechanism for the needle 60 (not shown). As such, the orientation of the barbs prevent the slidable handle 204 from sliding in one direction along the needle 60 (e.g. toward the end of the needle that is placed in the tissue), yet permit the handle 204 to slide in the opposite direction along the needle 60. This allows the practitioner to use the slidable handle 204 to control or guide the needle 60 through tissue and also reposition the slidable handle along the length of the needle 60.

Figure 27:
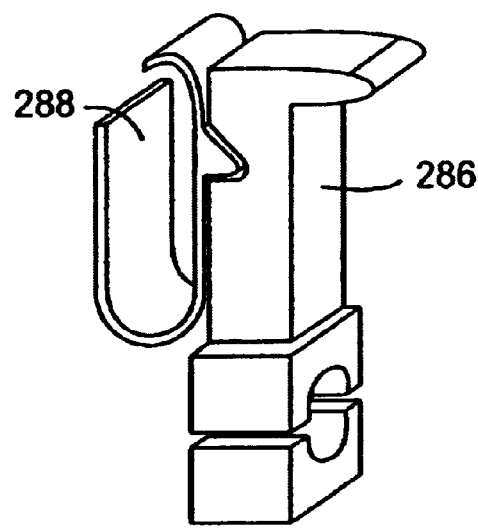
FIG. 27 is a perspective view of another embodiment of a locking mechanism of a slidable handle of the present invention.
Figure 28:
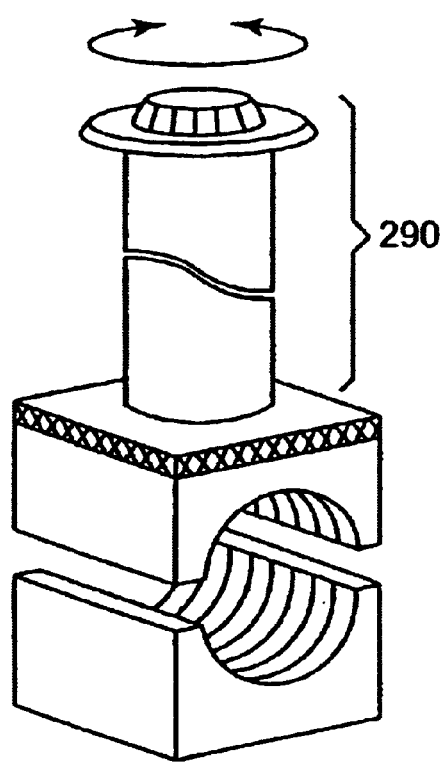
FIG. 28 is a perspective view of elements of another embodiment of locking mechanism of a slidable handle of the present invention.

Another embodiment of the locking mechanism is shown in FIG. 27. This mechanism is similar to the embodiment of the locking mechanism referenced in FIGS. 24A–24E. However, instead of depressing a cam 262, a user depresses a button 286 that latches into a mating release element 288. Yet another embodiment of a locking mechanism, shown in FIG. 28, comprises a screw-like device 290 that can be locked and unlocked simply by twisting or rotating a portion of the device 290. Other embodiments of locking mechanisms are also included within the scope of the claimed invention.

In another aspect, the present invention comprises a kit for treating a patient (e.g. for SUI). The kit preferably comprises at least two needles, an implantable material for supporting structure and at least two dilators. Two or more needles reduces the need to reuse a needle at a different location with a patient, thereby eliminating cross contamination issues. Additional needles, dilators and other elements may also be included for surgical convenience, for avoidance of contamination from one portion of the body to another, for ease of manufacturing or sterilization or for surgical requirements. For example, four needles may be utilized to implant the sling of FIG. 41. The needles would pass through abdominal incisions and through a vaginal incision.

Optionally, the sling 42 may includes a means for determining the tension in the sling. The tension determination means may comprise an element attached to the sling or incorporated in the sling that is capable of measuring sling tension.

The elements of the assembly of the present invention may be any color. Preferably, the elements are of constructed to be a color that contrasts with the intended physiological environment and with other elements. For example, the sling 42 is preferably white and the position adjustment member 66 may be blue. This helps the surgeon identify the location and discern the elements of the assembly.

EXAMPLES OF METHODS

Many methods are contemplated herein. Although the methods of use as disclosed herein generally relate to female incontinence conditions and treatments/procedures, male incontinence conditions and treatments/procedures are also included within the scope of the present invention. Procedures that address problems other than incontinence (e.g. cystocele, enterocele or prolapse) are also contemplated alone or in conjunction with the present invention. Further, the term "urethra," with respect to sling positioning, is used for brevity and reader convenience. It should be noted that the present invention is particularly suitable for placing a sling in a therapeutically effective position. The method may be utilized to support a variety of structures at different anatomical locations. As such, the terms "target site," "bladder", "urethro-vesical juncture", "vaginal vault", "U-V juncture" and "bladder neck" are also included within the scope of the present invention.

Referring now to FIGS. 29A through 30C, a preferred embodiment of surgical procedure for treating female incontinence is disclosed according to an aspect of the present invention. Initially, the patient is placed under local, spinal or general anesthesia. A small transverse incision 404 is made in the anterior vaginal wall 20 of a female patient followed by a transurethral dissection. Two small transverse suprapubic abdominal stab incisions 400 are also made near the back of the pubic bone (e.g. each about 1 cm from the midline, or alternatively, one large incision may be made) to allow for needle entry. Optionally, two paraurethral dissections (incisions next to the urethra) lateral to the midline may be created to allow the surgeon's finger to meet the end 58 of the needle 60 during the procedure.

A handle 64 is optionally adjusted relative to needle 60 according to surgeon preference and securely associated with the second end 62 of the needle 60. Optionally, the attachment and configuration of the needle-handle assembly may be adjusted or customized to user preference. The handle 64 may be optionally released from the needle 60 by pushing a button or compressing levers located on the handle 64. Once released, the handle 64 can then be rotated or displaced along an axis of the needle 60 to a preferred position. After the handle 64 is properly positioned on the needle 60, the button or levers are released, thereby causing the handle 64 to become securely attached to the needle 60.

Figure 29A:
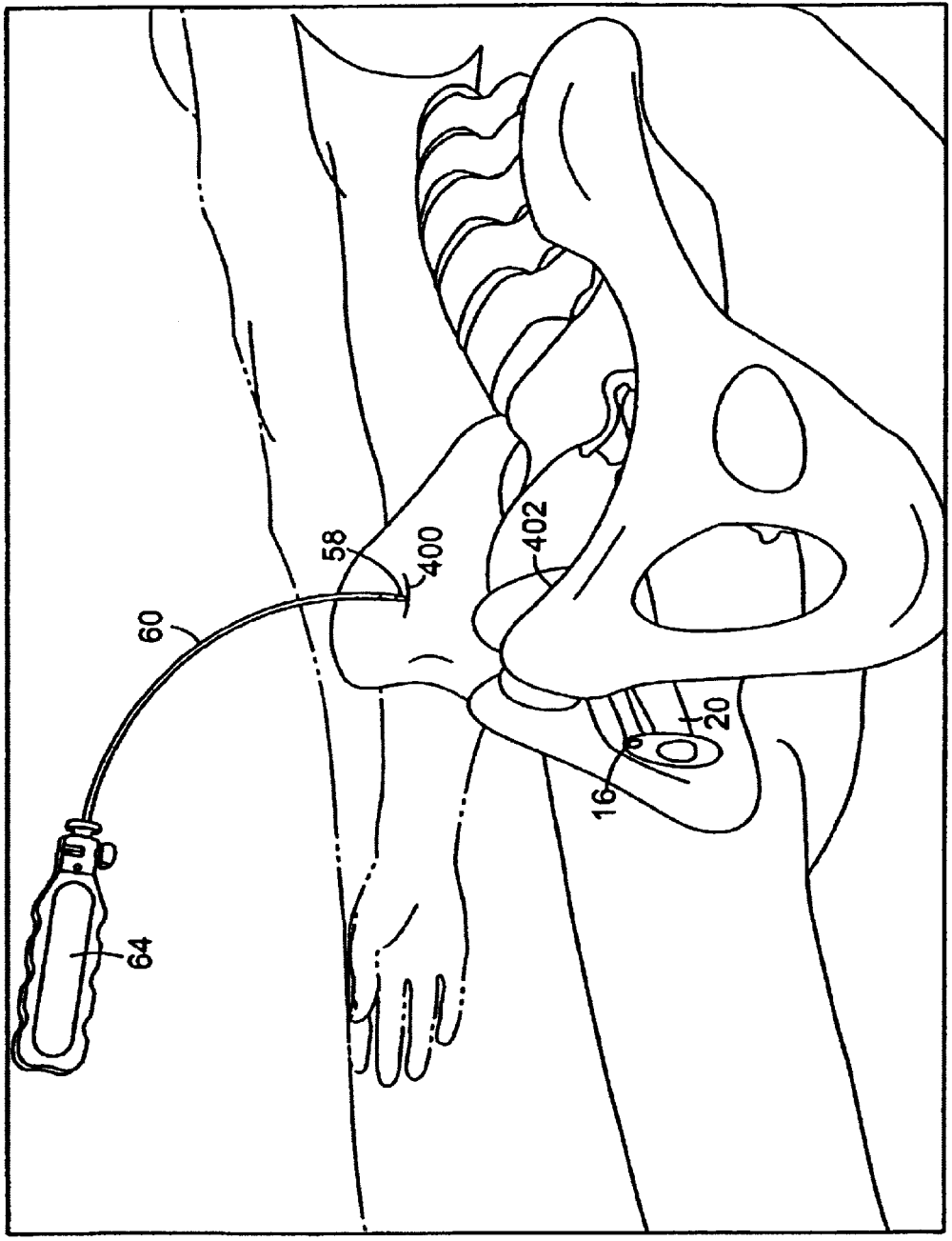

FIG. 29A shows the second end 58 of needle 60 just passing an abdominal incision 400. Preferably, after the second end 58 of the needle 60 passes the suprapubic abdominal incision 400, the surgeons seeks to encounter resistance associated with the posterior portion of the patient's pubic bone 402 with the second end 58 of the needle 60 to controllably move the end 58 of the needle toward the vaginal incision 404 and to help avoid damaging structures such as the urethra and bladder of the patient. The second end 58 of the needle 60 is used to identify the location of the pubic bone 402. The surgeon exploits the resistance provided by the pubic bone 402 to controllably pass the end of the needle 58. This approach is preferred as it helps keep the needle 60 away from major pelvic vessels, nerves and anatomical structures such as the urethra, bowels and bladder.

Figure 29B:
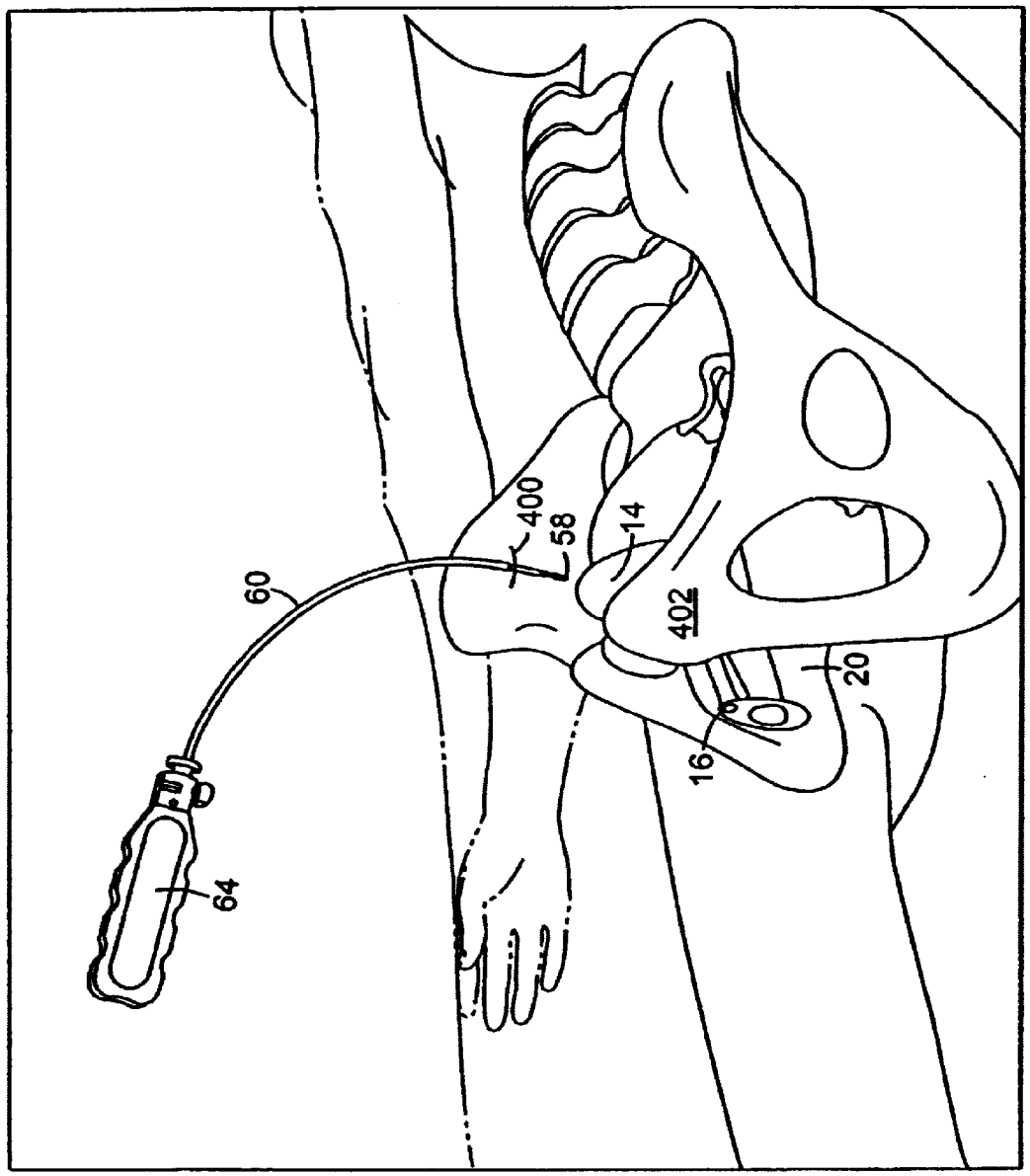
Figure 29C:
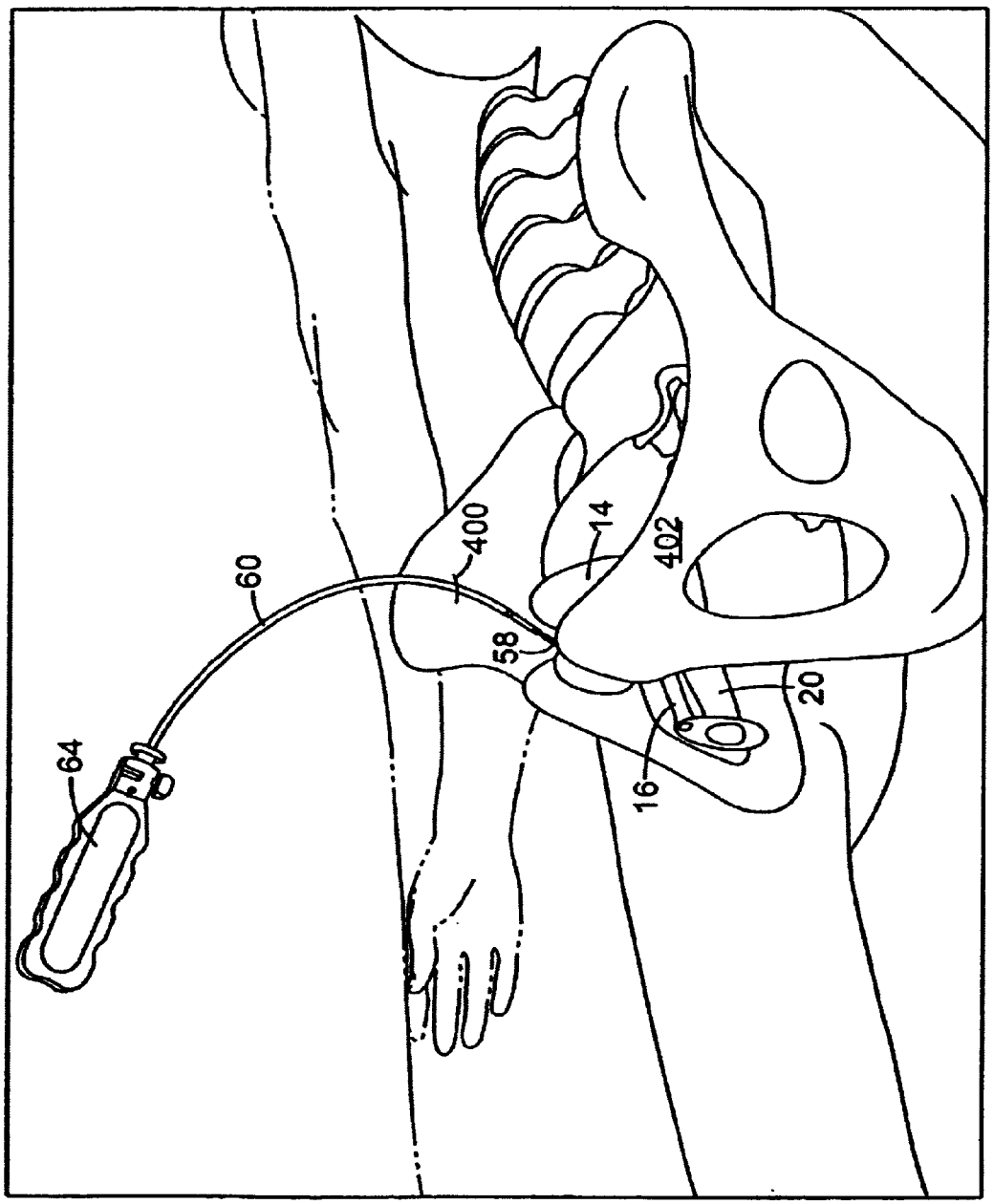

FIG. 29B illustrates the end of the needle as it just passes the suprapubic incision. FIG. 29C illustrates the needle 60 as the surgeon experiences the tactile feel of the resistance provided in part by the posterior portion of the pubic bone 402. FIG. 29C shows the needle 60 as it passes in proximity to the posterior surface of the pubic bone 402 which continues to operate as an anatomical guide for the surgeon as the needle end 58 approaches vaginal incision 404 (see FIG. 29D).

Figure 30A:
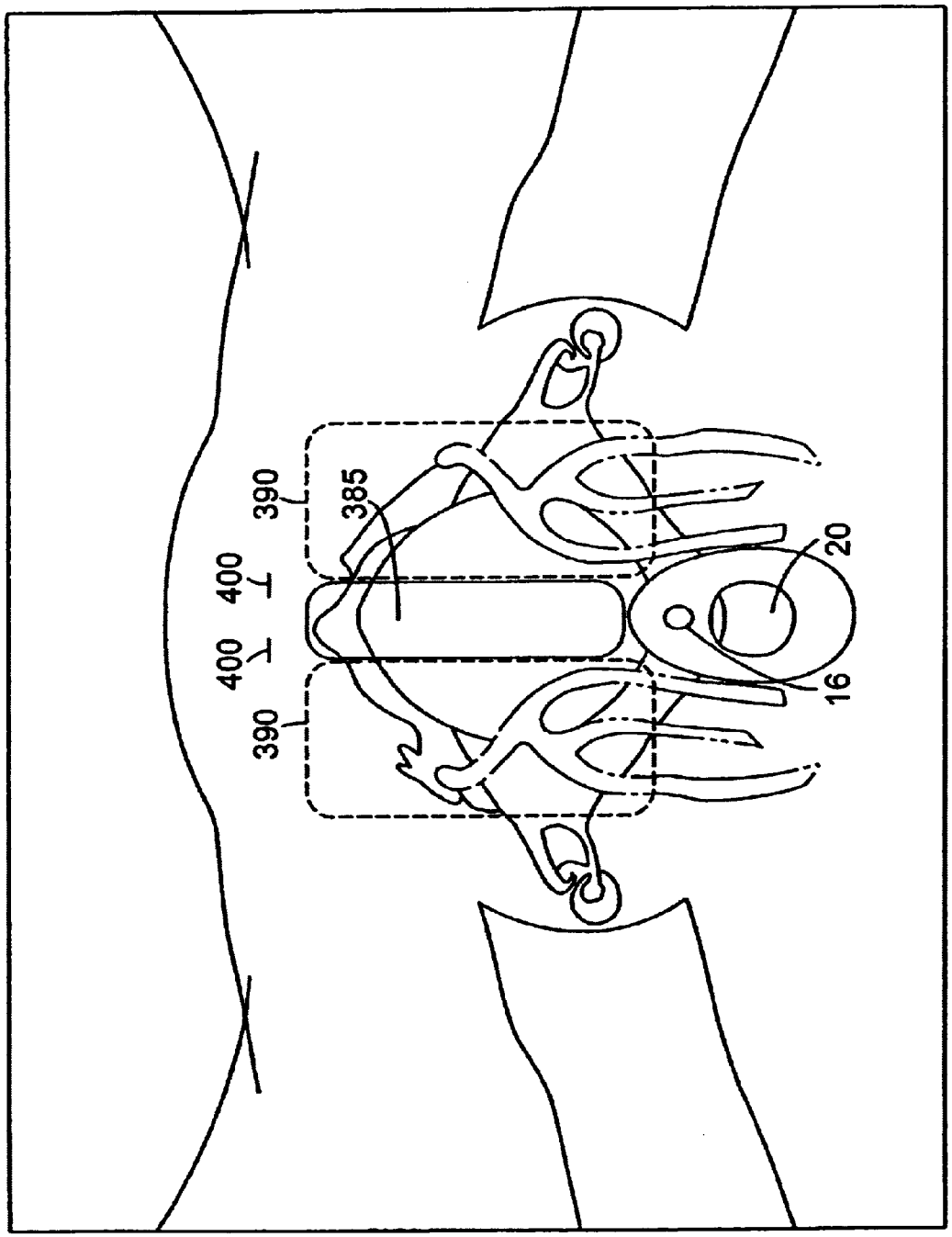
FIG. 30A is a schematic end view generally illustrating regions to avoid and preferred regions for needle passage in a patient according to an aspect of one embodiment of the present invention.

FIG. 30A is a schematic end view generally illustrating regions to avoid 390 during the surgical procedure and preferred passage region 385. Deviation of the end 58 of the needle 60 outside of the preferred passage region 385 into the regions to avoid 390 is believed to increase the potential for damaging arteries, veins, organs, lymph tissue and other tissues that are likely to lead to complications. Passing the needle 60 in the preferred passage region 385 avoids contact between the end of the needle 58 and these structures.

Figure 29D:
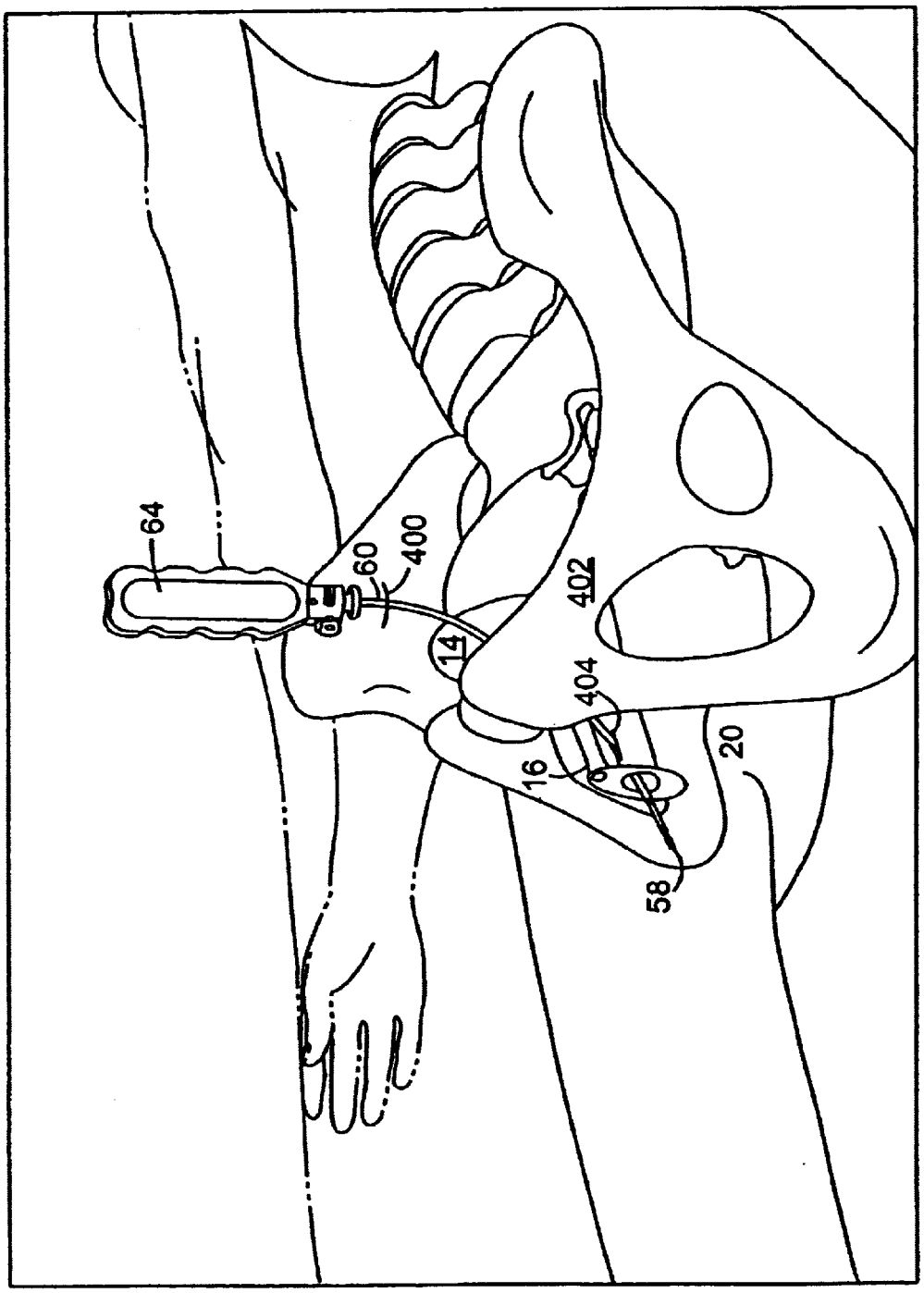

FIG. 29D illustrates the needle as it passes out of a vaginal incision 404. The surgeon typically holds the handle 64 of the needle 60 during this time by using predominantly one hand. Optionally, with the index finger of the opposite hand, the surgeon may meet the end 58 of the needle via the paraurethral dissection. The surgeon's finger may be delicately placed adjacent endopelvic fascia of the patient and used to guide the needle 60 through the relatively tough endopelvic fascia and into the vaginal incision 404. This helps the surgeon keep away from structures such as the bladder, urethra and other sensitive tissue.

The small diameter and curvature of the needles 60 help to provide precise passage of the needles 60 to the vaginal incision 404. In addition, this needle configuration creates a minimally invasive pathway through tissue extending between the abdominal wall and pubic space, thereby reducing the risk of perforating the bowel and/or blood vessels and nerves located lateral to the bladder 14.

Figure 30B:
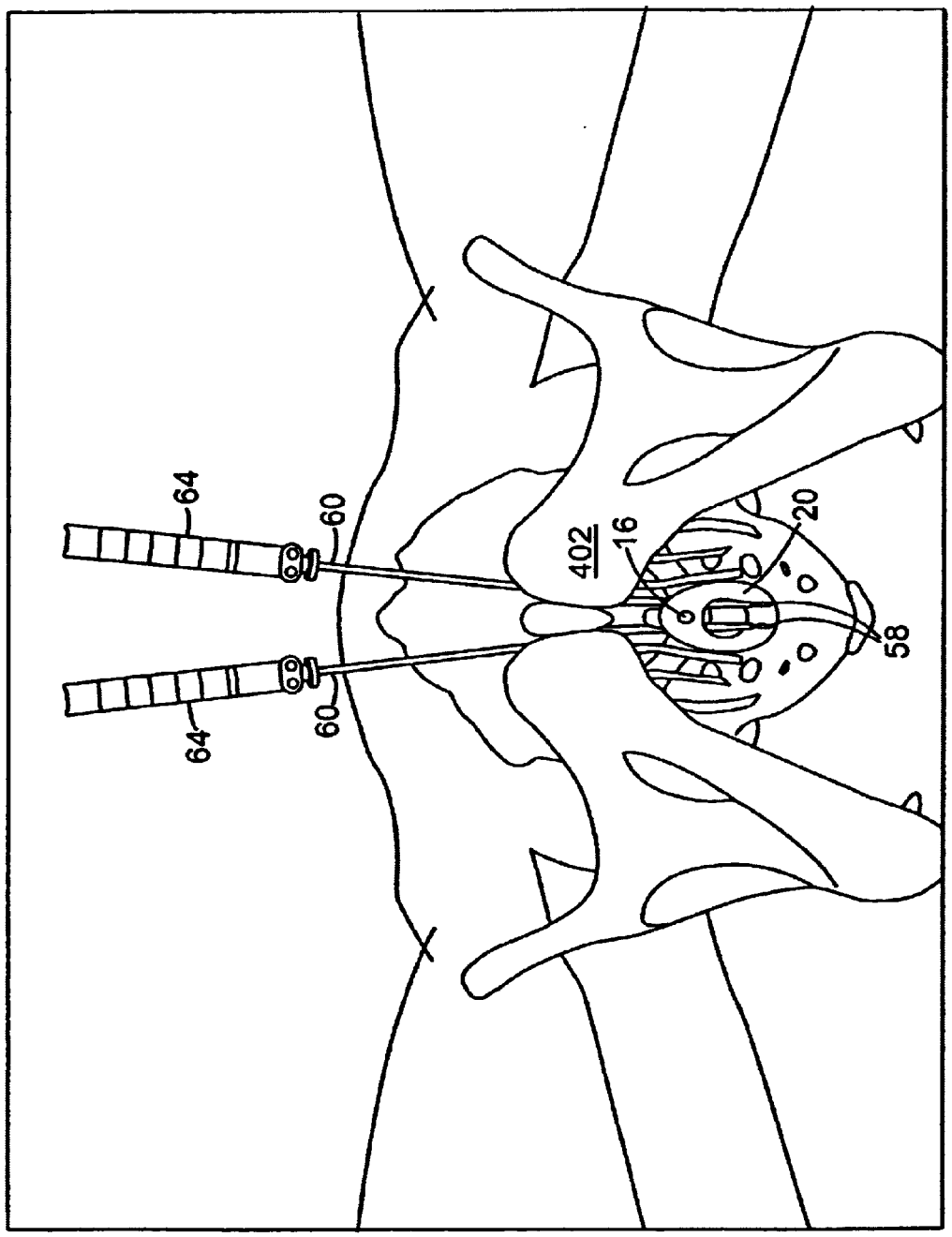
FIG. 30B is a schematic end view showing two needles placed in a patient and ready to receive a sling assembly according to another aspect of the present invention.

The steps described above are repeated as needed for a second needle 60 on the other side of the urethra 16. FIG. 30B is a schematic end view showing two needles placed in a patient and ready to receive a sling or sling assembly. Once both needles are placed, surgeons typically perform a cystoscopy to ensure that the bladder is not punctured before implanting the sling. A cystoscopy confirms the integrity of the bladder 14 and urethra 16 or recognizes a bladder perforation. The plastic cystoscopy aid shown in FIG. 14A may optionally be used for this purpose. The cystoscopy aid may be used separately or in conjunction with cystoscopy.

Figure 30C:
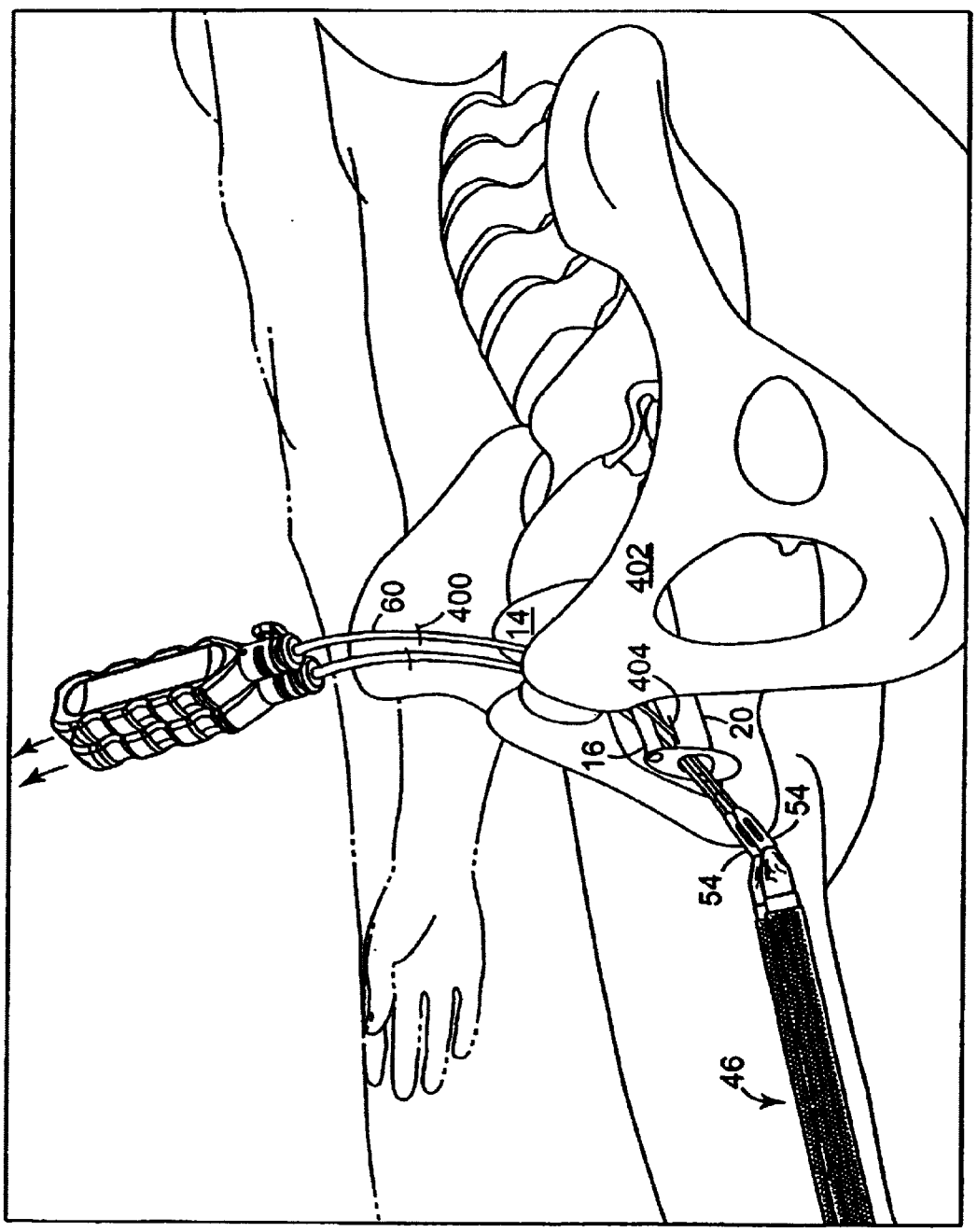
FIG. 30C is a perspective view of a sling system attached to two needles according to a preferred embodiment of the present invention.

FIG. 30C is a perspective view of a sling system associated with two needles 60. To attach the sling assembly, the plastic sheath 44 is oriented so that the optional center orientation indicia (e.g. a blue mark) is facing away from the surgical field, toward the surgeon. The dilators 54 are then pushed onto the ends 58 of needles 60 as shown in FIG. 30C. The dilators 54 are preferably snapped irreversibly into place for a secure connection. Also preferably, the dilators 54 are connected to the needle in a fashion that prevents rotation of the dilators 54 relative to the needles 60.

Alternatively, in another embodiment of the invention, the dilator need not be directly connected to the needles 60 and, instead, a flexible dilator with a lumen (e.g. dilator 54E shown in FIG. 14C) may be pushed along the exterior portion of the needle 60 in order to implant a sling. Preferably, the dilator of this embodiment is pushed in a direction from the vaginal incision 404 toward the suprapubic incision 400, but the opposite direction is also contemplated as within the present invention.

Returning to FIG. 30C, before snapping the second dilator 54 onto the needle 60, the surgeon determines that the majority of any optional adjusting filament 66 is facing away from the urethra 16 (see FIG. 6), and that the sling mesh is untwisted.

Dilators 54, including a pre-attached sling assembly 46, are attached to the first ends 58 of the needles 60 protruding from the vagina 20. As discussed above, after the first dilator 54 is attached to one needle 60, the sling assembly 46 is properly oriented so that the sling assembly 46 is not twisted prior to attaching the second dilator 54 to the end of the other needle 60. In addition, the sling assembly 46 is oriented so that the larger filament loops (of the position adjustment member 66) are facing outward or away from the urethra 16. After the dilators 54 and sling assembly 46 are properly positioned, the dilators 54 are securely attached to the needles 60 to ensure that they do not become detached as the needles 60 are preferably pulled simultaneously through the tissues of the patient.

Once the dilators 54 are securely attached, the needles are pulled up through the suprapubic incisions as shown by the arrows in FIG. 30C, taking care to avoid contact with sensitive tissue. The sling is then clamped with surgical clamps (not shown). Preferably, the handles 64 are used to pull the needles 60 up through the suprapubic incisions 400. During this portion of the process, the attached dilators 54 and sling assembly 46 are atraumatically pulled up through the needle paths, advancing the sling assembly 46 adjacent to and looped beneath the urethra 16 or target site. A portion of each end of the sling assembly 46 extending beyond the suprapubic incisions 400 is clamped and then cut to release the needles 60 and attached dilators 54.

The sling is placed in a therapeutically effective position. The precise anatomical position will depend upon a variety of factors including the type and degree of anatomical damage or insufficiency, whether the sling procedure is combined with other procedures and other surgeon decisions. Typically, the sling is placed midurethra, without tension, but in position to support the midurethra. Alternatively, the sling could be placed to support the bladder neck and/or UV junction.

Once the sling assembly 46 is carefully positioned under the midurethra or target site to provide sufficient support to the target site, the overlapping portion of the sheath 44 located near the center of the sling assembly 46 and the axially located member 66 (i.e. tensioning filament) may then be used to center and properly position the sling assembly 46 under the midurethra. The sheath 44 is then removed.

Figure 31A:
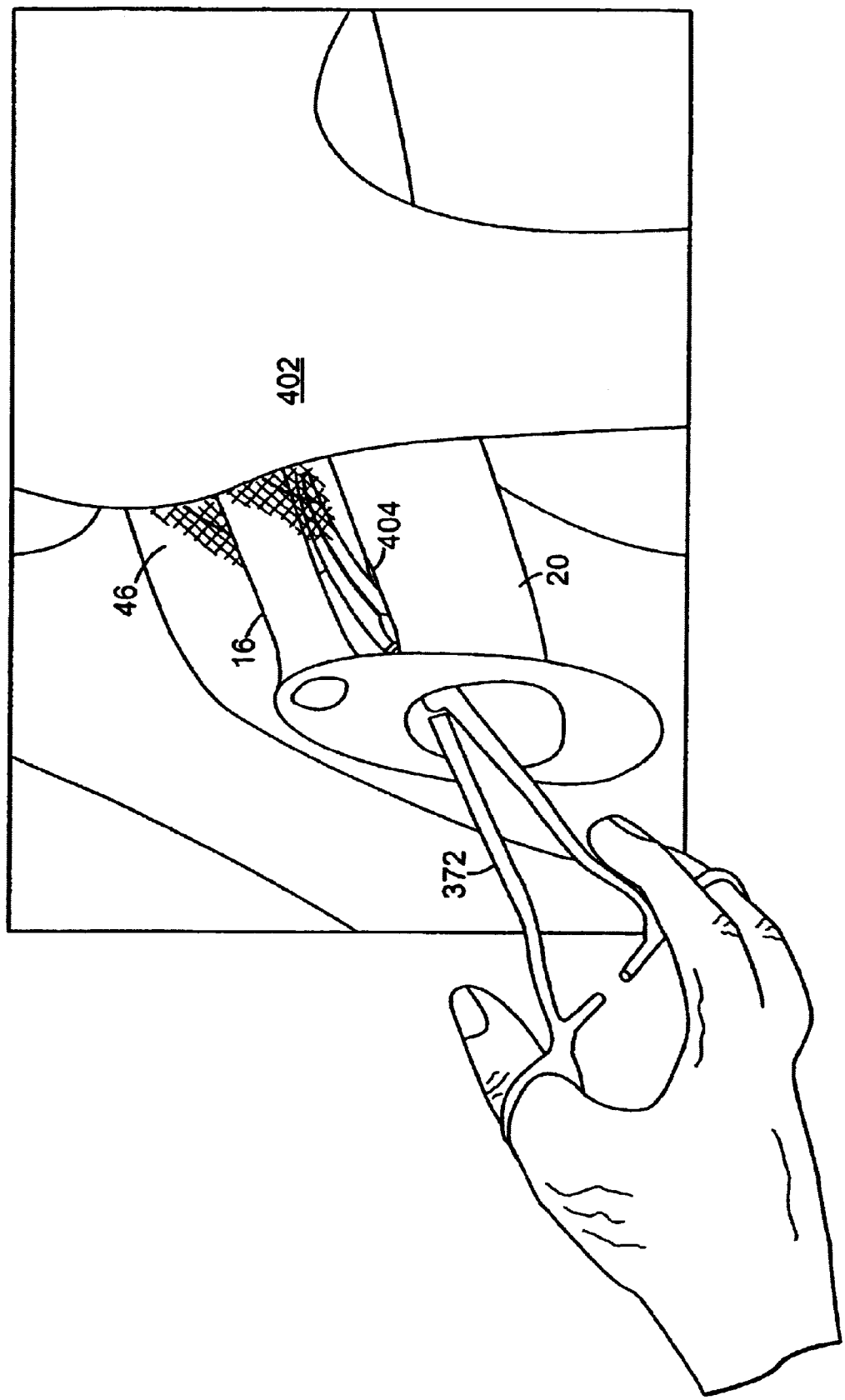
FIG. 31A is a perspective view of the sling placed in proximity to the urethra of a patient that shows one method of changing the position of the sling during the surgical procedure, which method is a method of loosening the tension of the sling.

FIG. 31A is a perspective view of the sling placed in proximity to the urethra of a patient that shows one method of permanently adjusting the position or "tension" of the sling during the surgical procedure. Using the position adjustment member 66 on the sling mesh to reposition the sling 42, the surgeon pulls down or away from the urethra on the sling 42 and position adjustment member 66 using a blunt instrument 372 to shift the sling away from the urethra 16, thereby reducing tension. The blunt instrument (e.g. a clamp) is used to pull down and, thereby, displace the sling 42 as desired. The position adjusting member 66 transfers some of the force placed on the sling 42 by the blunt instrument 372 to another location on the sling (e.g. the end 61 of the support portion II of the sling 42 shown in FIG. 1A). This action is believed to be effective in permanently reducing the tension of the sling 42 and increasing the space between the sling 42 and the urethra 16, even after the sheath 44 is removed.

Preferably, the position adjustment member 66 is a continuous member that extends the length of the support portion II (FIG. 1A) of the sling 42 and avoids contact with the vaginal incision 404. This affords convenient contact between the sling 42/member 66 and member 372 at any location along the length of the support portion II. In contrast, a member 66 that is separated at the mid portion of the sling would be difficult to engage with member 372. A sling with a continuous, non-separated position adjustment member 66 is particularly helpful, as the surgeon is working at a remote location in cramped quarters. Additionally, a position adjustment member that hung down into the vaginal incision 404 may cause complications due to interaction with the incision 404.

After achieving the desired sling location, the position adjustment member 66 laterally located on both sides of the urethra 16 may be cut (e.g. at the ends 61 of the support portion II) and removed. Alternatively, the position adjustment member 66 may be left in place, particularly if it consists of a degradable material or is an integral part of the sling 42. The sling 42 is also trimmed adjacent to the suprapubic incisions 400, thereby removing the excess sling material extending outside the body of the patient.

Figure 31B:
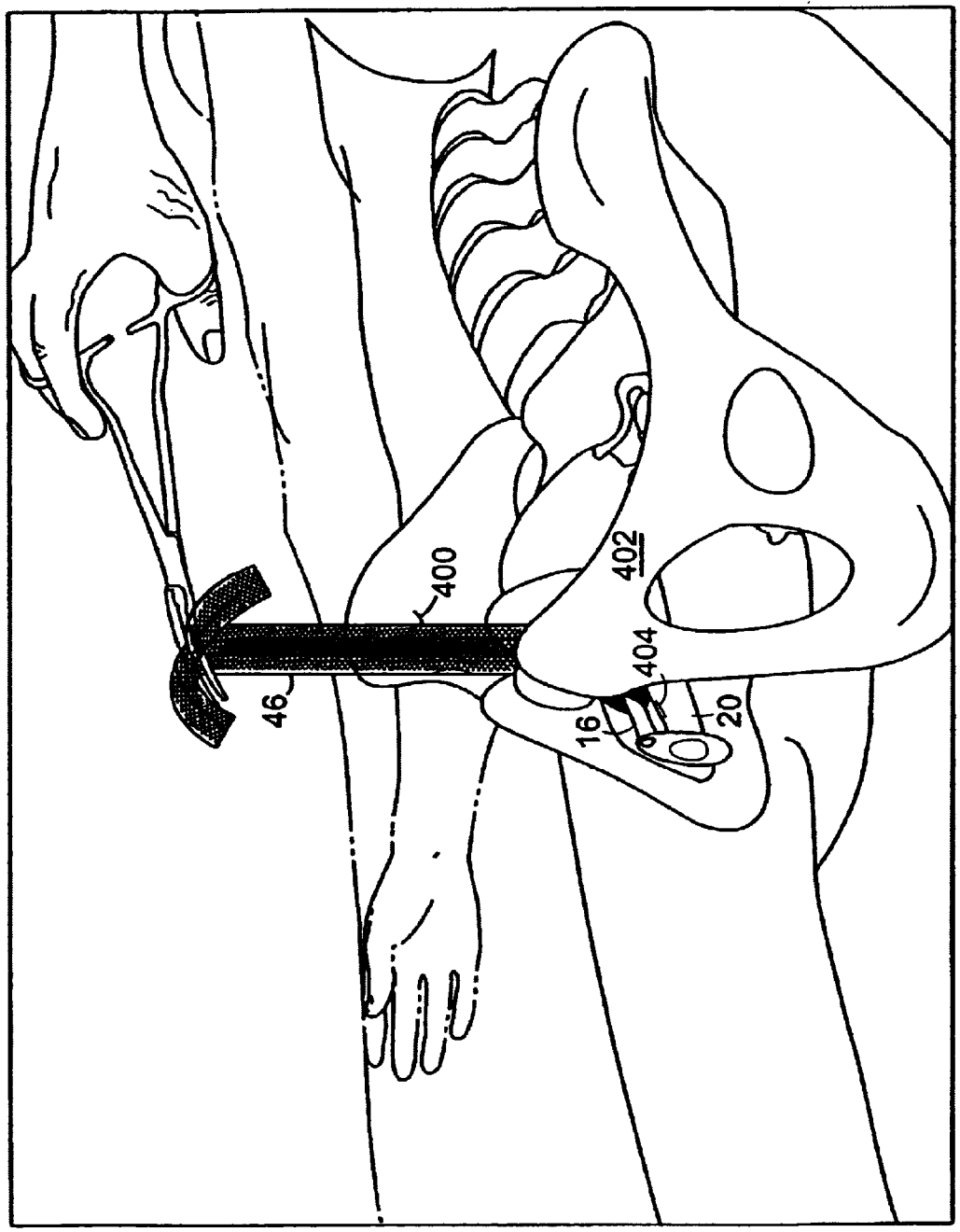
FIG. 31B is a perspective view of another method of adjusting the tension of the sling during the surgical procedure according to the present invention, showing a method of tightening the tension of the sling.

Preferably the position adjustment member 66 extends substantially along the entire length of the sling 42 (see FIGS. 1 and 1A) so that the member 66 can be used to increase the tension of the sling (e.g. position the sling closer to the urethra). FIG. 31B is a perspective view of another method of adjusting the position or "tension" of the sling during the surgical procedure. Sling tension may be tightened by placing a device, such as a clamp, across one or both ends of the sling 42, suprapubically. The entire sling width and the associated member 66 should also be captured within the clamp. In addition, the sling 42 may be rolled or looped around the clamp to improve the grip. As such, the end of the sling 42 is then pulled in an upward direction to tighten the sling 42 as desired. The tension adjustment member 66 transfers some of the force provided by the clamp to another location of the sling (e.g. the ends 61 of the support portion II) to more effectively reposition the sling 42. If necessary, this tightening procedure can also be repeated on the other end of the sling 42 located on the contra lateral side. In contrast, a member 66 that does not extend substantially along the entire length of the sling 42 (see FIGS. 1 and 1A) could not be used to increase the tension of the sling.

Figure 31C:
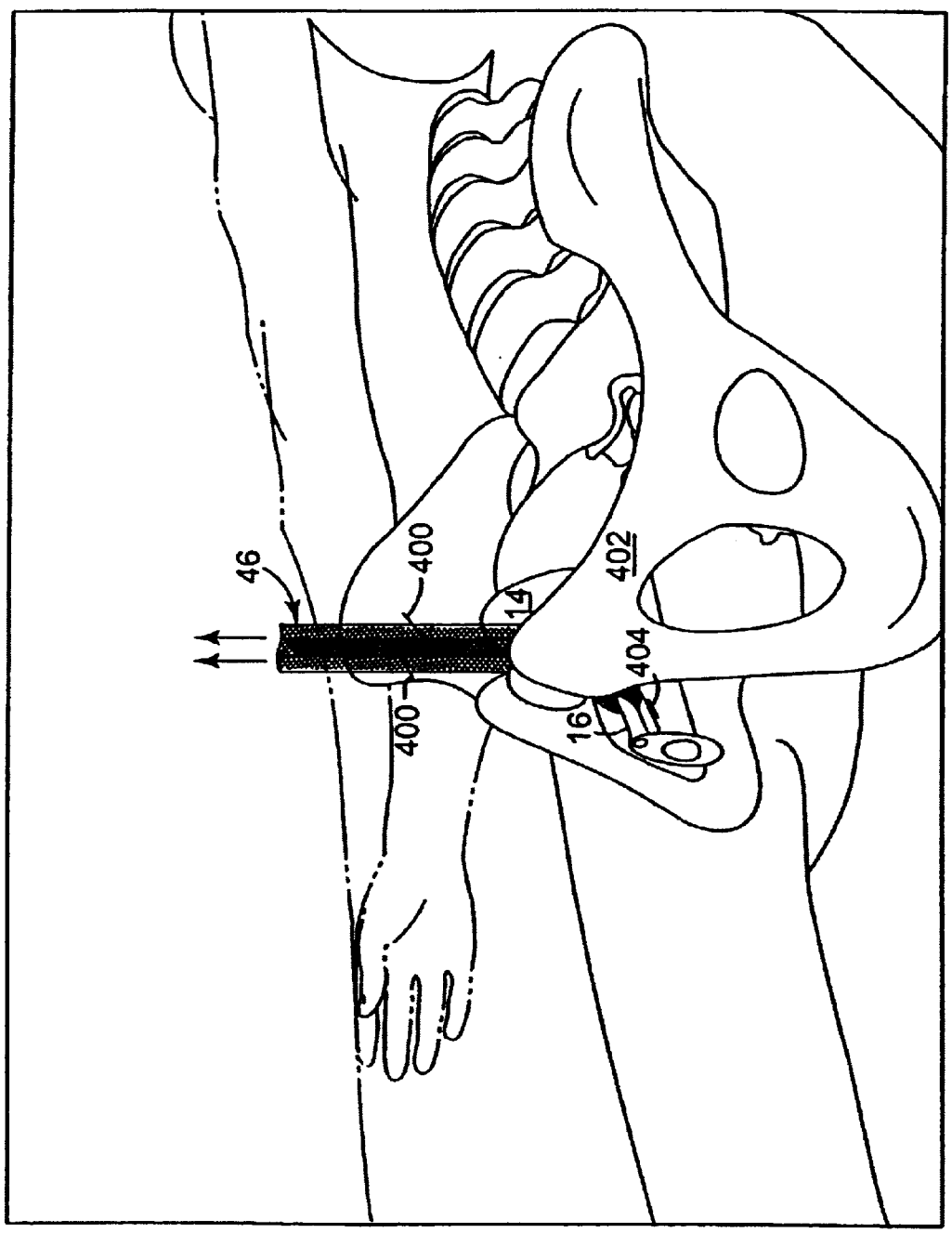
FIG. 31C is a perspective view the sling according to the present invention after the dilators have been separated from the rest of the assembly, but prior to final trimming.

Generally, the surgeon grasps the mesh and tensioning filament together adjacent the suprapubic incision 400 and pulls to increase the tension of the mesh. Adjustment may occur before or after the dilators 54 or sheath 44 are separated. FIG. 31C shows the sling after the dilators have been cut off, but prior to final trimming.

Figure 32:
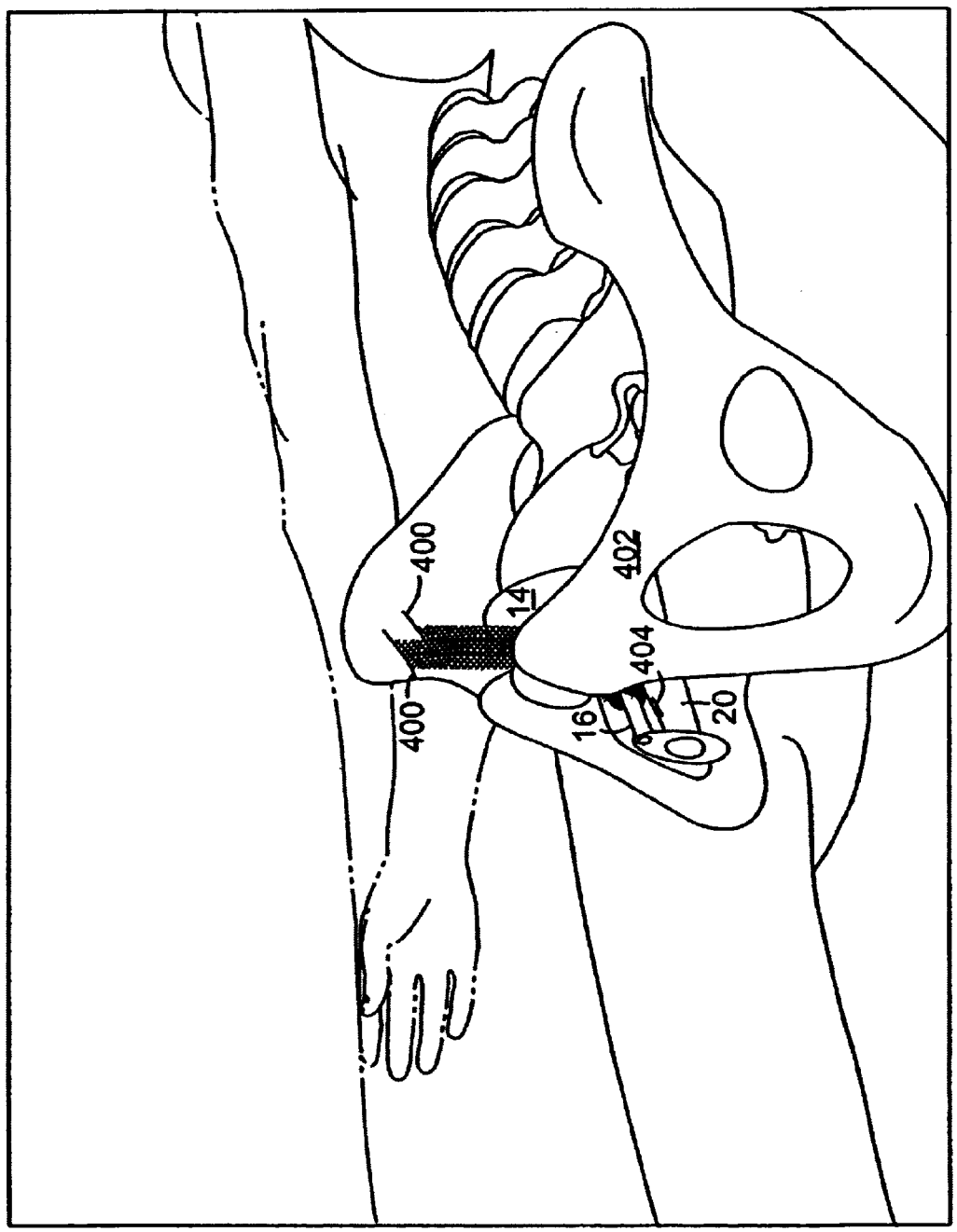
FIG. 32 is a perspective view of the sling according to the present invention after the sheath has been removed and the sling has been trimmed.

The position adjustment member 66 may be cut lateral to the urethra on both sides (e.g. at 61 in FIG. 1) and it is removed prior to the end of the surgical procedure. Optionally, it may be left in place after the surgical procedure. The sling 42 is finally cut to size at the suprapubic incisions 400 as shown in FIG. 32. After the procedure, the surgeon closes the suprapubic and vaginal incisions. A Foley catheter may be used to facilitate voiding at the surgeon's discretion.

The surgeon verifies the proper placement of the sling 42 as the sling mesh may be difficult to move after the plastic sheath 44 is removed. After the dilators 54 are trimmed off as shown in FIG. 31C, the plastic sheath 44 is removed from the sling mesh 42 by pulling up on both sides of the sheath 44, preferably one at a time, and preferably in the direction of the arrows of FIG. 31C. Optionally, to avoid overtightening the sling mesh 42 while removing the sheath 44, a forceps or other blunt instrument may be placed between the sling and the urethra.

In an alternate embodiment, the member 66 is not cut and remains attached to the sling 42. Maintaining filament 66 attachment to the sling 42 affords convenient postoperative adjustments to sling tension. Further, with respect to the embodiment of the invention whereby the member 66 is coated with a radiopaque substance, retaining the member 66 allows the practitioner to track post-operative changes to the position of the sling 42 and/or urethra 16.

The position of the sling may be adjusted using the member 66 even after the surgical procedure without requiring a subsequent vaginal incision and without having any structure passing through the original vaginal incision 404. FIG. 37 is a perspective view of another method of permanently repositioning or adjusting the "tension" of the sling. In this procedure, typically after the surgical procedure and before any optional bioresorbable portion of the filament is absorbed by the body or rendered ineffective for the purpose of tension adjustment, the surgeon places a blunt device in the urethra 16 and pulls down, thereby permanently loosening the tension of the sling 42. This may help avoid the need to reposition the sling by dissecting the vagina 20 and grasping the sling. Alternatively, but not preferably, the vagina may be dissected and the member 66 or sling 42 directly accessed through another vaginal incision.

Figure 33:
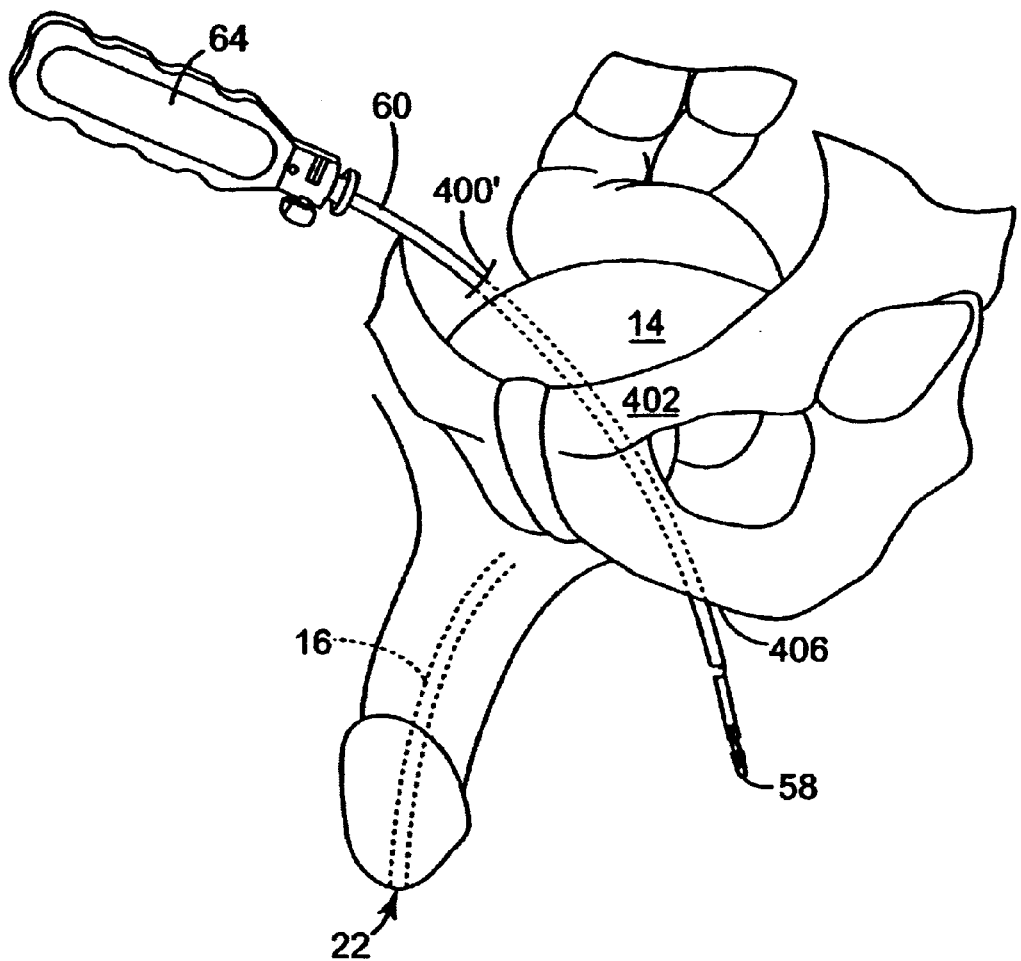
FIG. 33 a schematic perspective view of another embodiment of the method of use of the sling delivery system of the present invention with respect to the male anatomy.

Referring to the alternate embodiment shown in FIG. 33, a small incision is made in the perineal area 406 of a male patient. As with the female patient, two small transverse suprapubic incisions 400 are also made to allow for needle entry. After the handle 64 is securely attached and properly positioned on the needle 60, the first end of the needle 60 is passed through one of the suprapubic incisions 400, down the posterior side of the pubic bone 402, through the endopelvic fascia and into the perineal incision 406. The user of the device utilizes the handle 64 to guide the needle 60 through the various tissues, avoiding major pubic vessels, the bladder 14 and prostate gland. The second needle 60 is inserted in a similar fashion on the contra-lateral side. A cystoscopy procedure may be performed to confirm bladder integrity. The dilators 54 and sling assembly 46 are then positioned under the target site, sling tension is adjusted and the remainder of the procedure is performed similar to that previously described for a female patient.

In another embodiment of the invention, the previously described cystoscopy aids 54D (FIG. 14B) can be used in addition to, or optionally in place of the cystoscopy procedure. Once both needles 60 are in place, the cystoscopy aids 54D are passed along the length of the needles 60. If the bladder has been punctured during needle insertion causing urine leakage within the patient, the urine enters the apertures 160 of the cystoscopy aids 54D, flows along the surface and out from the needle 60. Based on the configuration of the cystoscopy aids 54D and desired treatment/procedure, the cystoscopy aids 54D may be removed, the sling 42 or sling assembly 46 may be attached to the cystoscopy aids 54D or the sling 42/sling assembly 46 may be hidden within or pulled through the cystoscopy aids 54D. Preferably, the cystoscopic aids are a contrasting color (e.g. blue) to afford ready identification of blood or other leakage from the bladder or other structures.

In an alternate embodiment, the slidable handle 204 is used in place of or in combination with the handle 64. As previously described, the slidable handle 204 is positioned in a locked configuration near the first end 58 of the needle 60 and handle 64 is positioned near the second end 62 the needle 60. The repositionable handle 204 may be used as a stop to prevent inadvertent lurching of the needle 58 into sensitive tissue. As the needle 60 is inserted into the incision, the user or practitioner pushes the needle 60 through the incision 400 using handle 64 and guides or maneuvers the needle 60 through the various tissues and spaces using slidable handle 204. When the slidable handle 204 comes in close proximity to the incision, the user unlocks the handle 204 and slides the handle 204 along a length of the needle 60. The slidable handle 204 is thereby repositioned away from the incision and closer to the first end 62 of the needle 60. Once properly located, the slidable handle 204 is then locked in place and the insertion procedure continues. The unlocking, repositioning and locking actions are repeated at the convenience and discretion of the surgeon until the needle 60 is fully inserted. Thus, this embodiment provides a system with more controlled and precise maneuverability than prior art structures.

Figure 34:
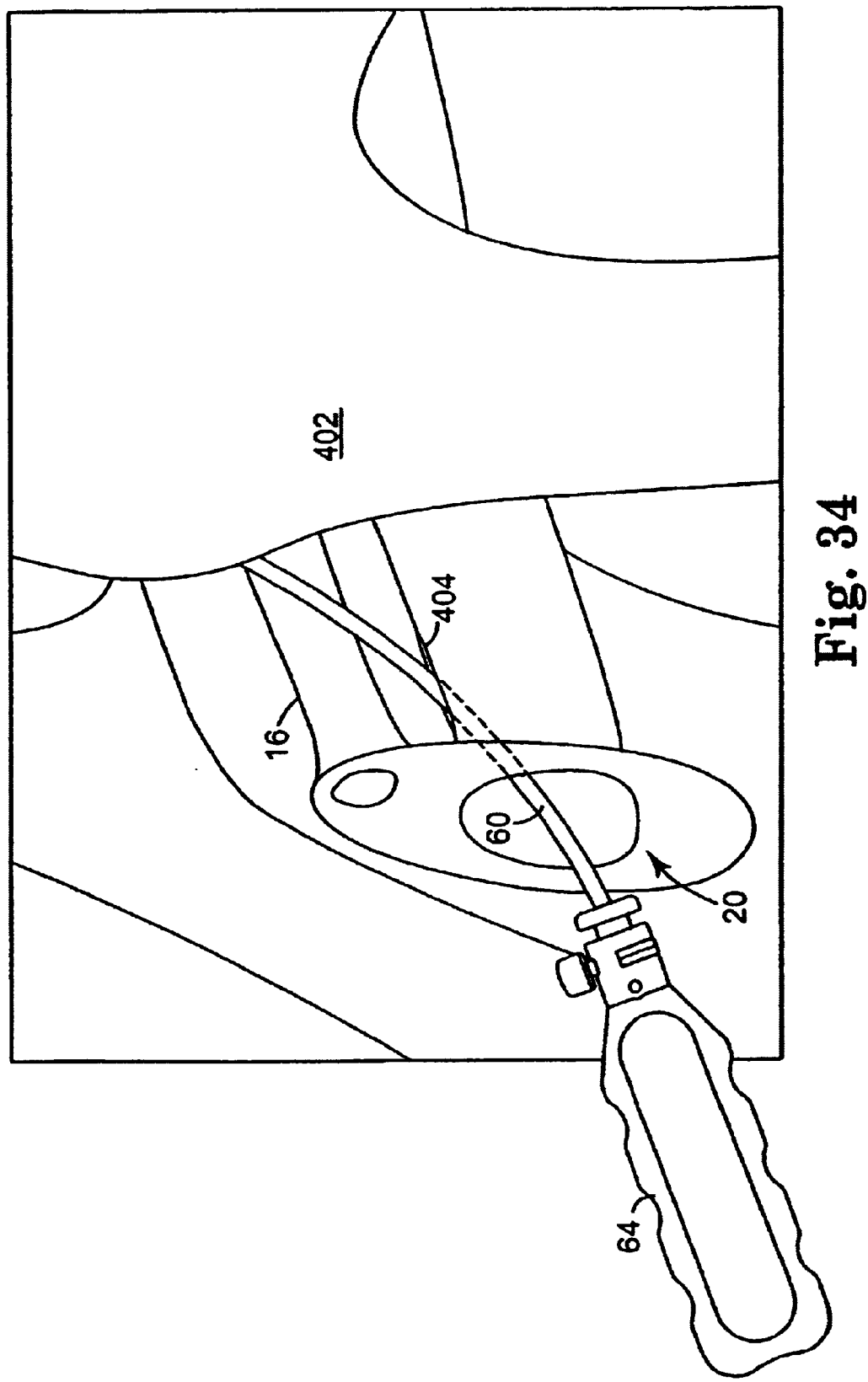
FIG. 34 is a perspective view of another embodiment of surgical procedure according to the present invention showing a needle being initially inserted into the body transvaginally as opposed to suprapubically.
Figure 35:
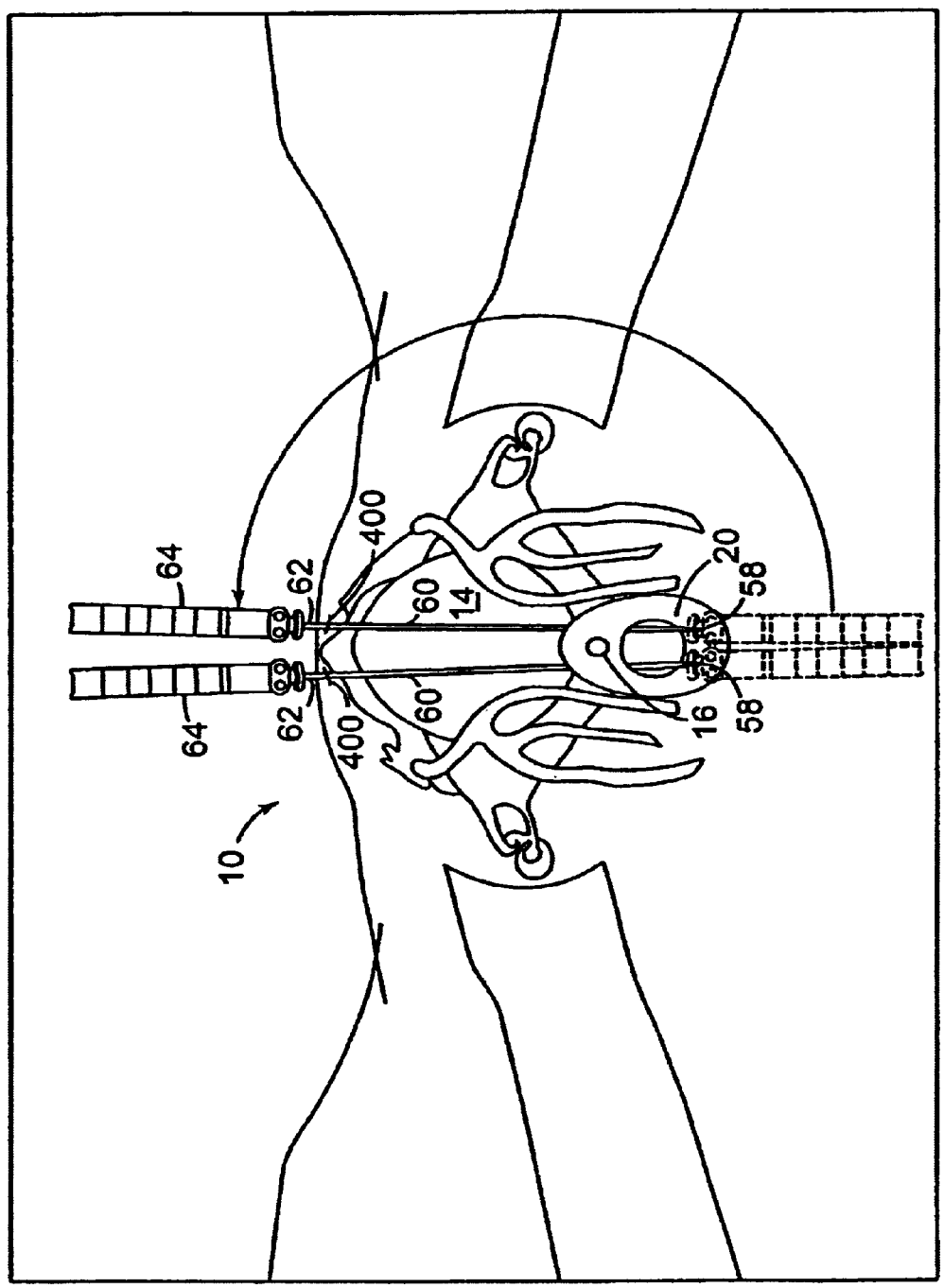
FIG. 35 is an end view of two surgical needles after being inserted in the body transvaginally as shown in FIG. 34, showing handles of the needles on one end of the needles with dashed lines and using an arrow and solid lines to show that the handles are removed and reattached to the needles on the other ends of the needles.
Figure 36:
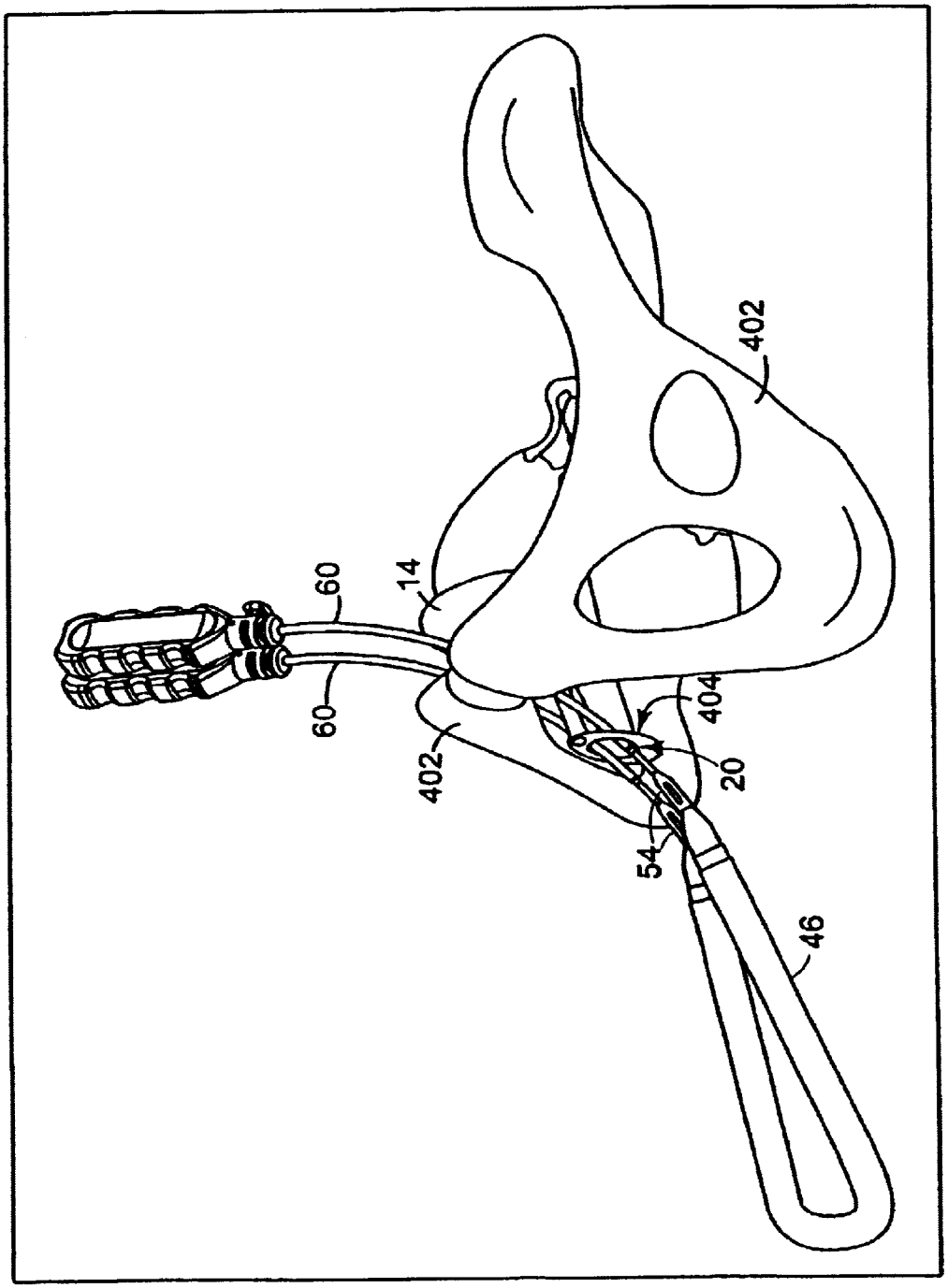
FIG. 36 is a perspective view of the needles of FIG. 35 after a sling assembly has been attached.

In another embodiment of the invention, shown in FIGS. 34 through 36, one end of the needle 60 is initially passed through a vaginal incision 404 and toward one of the suprapubic incisions 400. While inserting the needles 60 initially through the vagina is not preferred, it is within the scope of the present invention as some surgeons may prefer this approach due to previous surgical training, custom or personal preference. The handles 64 are used to push and precisely guide the needle 60 through the various tissues, without perforating or damaging the bowel and/or blood vessels. With the first needle 60 in place, a second needle 60 may be inserted in the same way on a contra-lateral side. As before, a separate cystoscopy procedure may be performed to confirm bladder integrity.

As shown in FIG. 35, the handles 64 are detached from one end of the needles 60 and securely attached at the opposite ends of the needles 60 protruding from the abdominal incision 400. In this configuration, a user of the device can use the same handles 64 to also withdraw the needles 60 from the patient. Alternatively, the first pair of handles 64 can be detached from the needles 60 protruding from the vagina and discarded. A second pair of new or different handles 64 can then be attached to the needles 60 protruding from the abdominal incision 400 and used for the remainder of the procedure.

Referring to FIG. 36, the dilators 54 and sling assembly 46 are attached to the ends of the needles 60 protruding from the vagina 20. The remainder of the procedure is similar to that described in previous embodiments of the invention.

Figure 38:
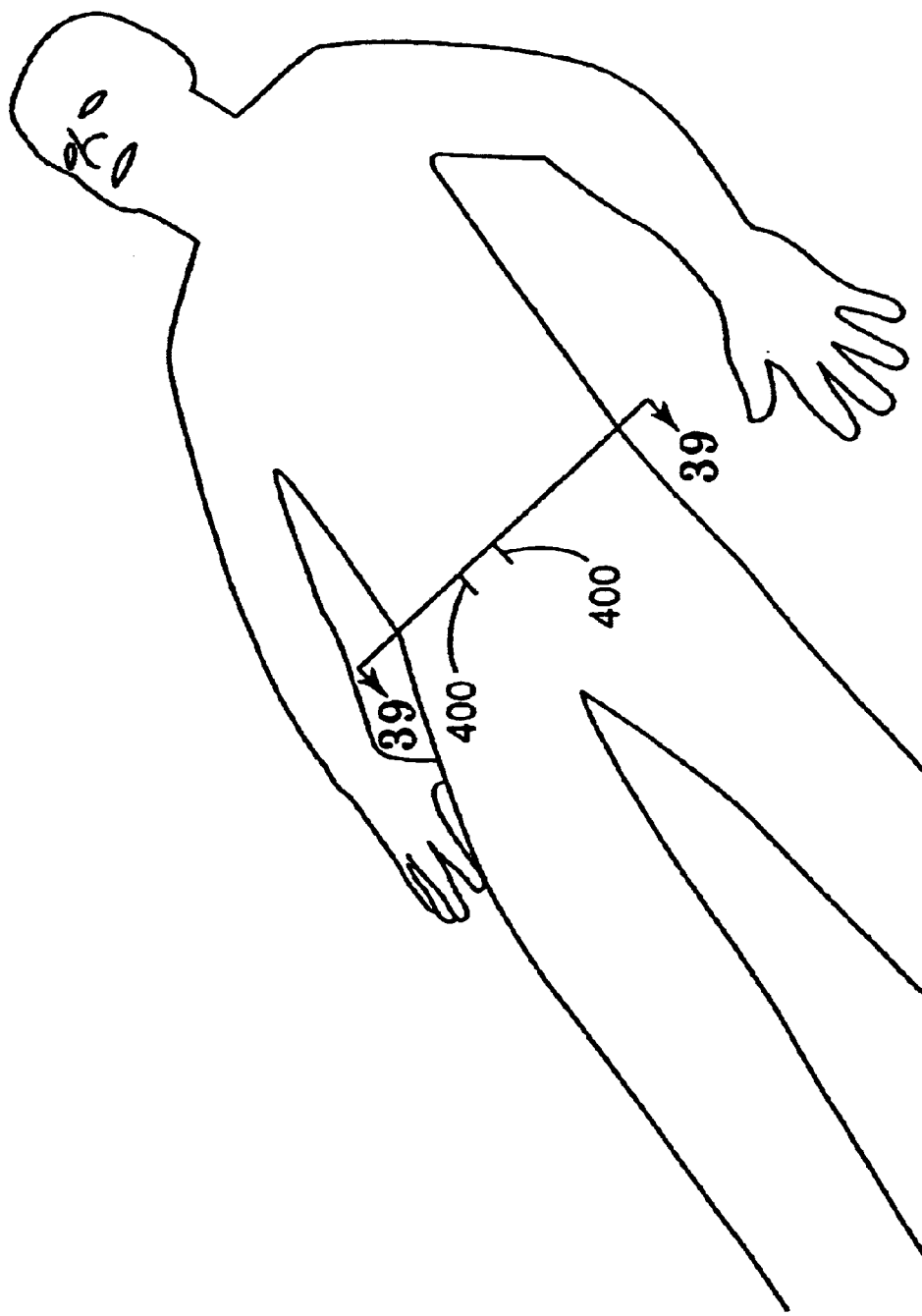
FIG. 38 is a schematic view of a cadaver.
Figure 39:
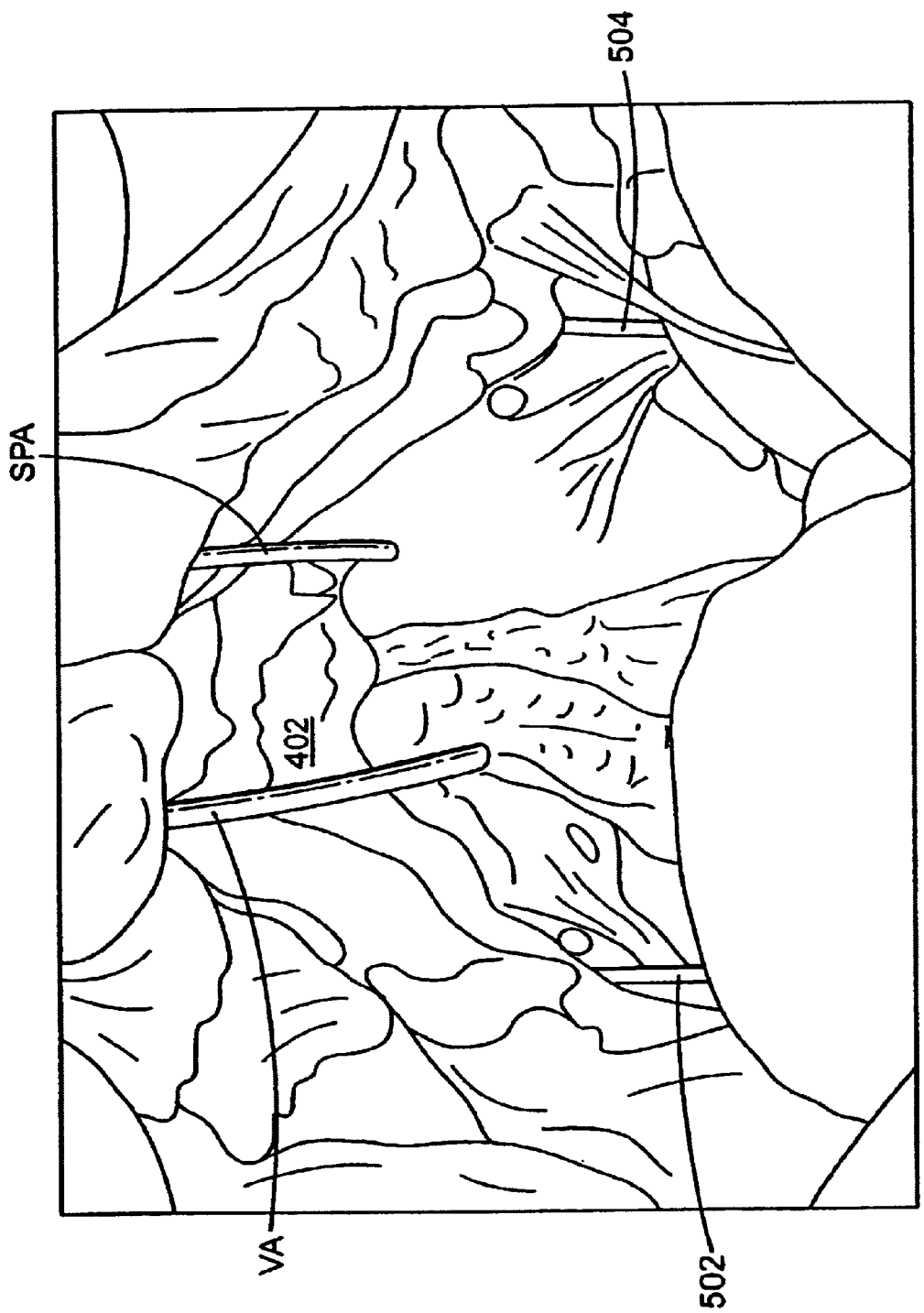
FIG. 39 is a perspective view of the cadaver of FIG. 38 showing proper placement of a prior art needle that was initially inserted transvaginally (on the left) and showing proper placement of a needle according to the present invention that was initially inserted suprapubically (on the right)

When using the embodiment of the present invention described in conjunction with FIGS. 34–36, additional attention is directed to keeping the needles away from major pubic vessels, nerves and organs such as the urethra, bowel and bladder. FIG. 38 is a schematic view of a cadaver. FIG. 39 is an illustration of an opened cadaver showing, on the left, a prior art TVT needle VA that was properly placed using an initial vaginal approach; and on the right, a needle SPA properly placed according to a preferred embodiment of the present invention (using a suprapubic approach). The TVT procedure requires the surgeon to blindly pass a large diameter stainless steel trocar upward in a retrograde, retropubic fashion through the retropubic space to position a sling beneath the urethra. The upward approach lacks anatomical guides to assist in positioning the needle in a path that is spaced from pelvic vessels, nerves, organs and sensitive tissue such as the urethra, bladder and bowel.

Figure 40:
FIG. 40 is a perspective view of a cadaver showing undesirable lateral deviation of the prior art needle that was initially inserted transvaginally (on the left) and showing undesirable lateral deviation of the needle according to the present invention that was initially inserted suprapubically (on the right)

FIG. 40 is another view of the cadaver showing the TVT needle VA laterally deviated from its proper path and the needle SPA laterally deviated from its proper path. Because the vaginally inserted TVT needle VA is blindly passed upward through the retropubic space, it is believed that the end E of the needle VA is more prone to injure pelvic vessels and nerves 502 or even the bladder or bowel. In contrast, even if the end 58 of the needle SPA inserted according to a preferred embodiment of the present invention deviates slightly laterally as shown in FIG. 40, the surgeon may exploit the resistance provided by the posterior portion of the pelvic bone 402 to correct the path of the needle SPA back into the preferred passage region 385 (FIG. 30A) and avoid the pelvic vessels and nerves 504. This also helps reduce the risk of puncturing sensitive tissue such as that of the bladder, bowels and urethra.

As previously described, the device of the present invention can also be used for male patients. Just as the vaginal approach may be used for female patients, a perineal approach may be used for male patients. One end of a needle 60 is initially passed through a perineal incision 406 and toward one of the suprapubic incisions 400. The insertion of the second needle 60 and the remainder of the procedure are similar to that previously described.

In an alternate embodiment, sheath tags, center markers or other means may be used to aid the practitioner in accurately centering the sheath 44 under the urethra or bladder neck in females or bulbar urethra in males. Thus, end and/or center markings may be used as additional aids for separating the delivery system from the sling 42 and centrally placing the sling 42 at the target site.

In another embodiment of method according to the present invention, four needles may be utilized to implant the sling shown in FIG. 41. The needles may extend from four abdominal incisions to a vaginal incision. The sling 42P may be used as a hammock to support the bladder or for other procedures to address a cystocele or prolapse or a vaginal vault treatment.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A sling for treating urinary incontinence in a patient comprising:
   first and second major surfaces,
   a pair of end portions,
   a support portion for placement in a therapeutically effective position relative to a physiological environment intended to be supported, the support portion having an axially elongate mesh, and a pair of ends, and
   repositioning means, associated with the sling, for transferring sling tightening or sling loosening forces along the sling to afford effective, permanent repositioning of the sling without adversely affecting the therapeutic effect of the sling;
   wherein the sling includes a removable sheath and the repositioning means affords permanent tightening of the sling when the sling is partially implanted and the sheath is removed, by pulling on the sling and repositioning means at a suprapubic location.

2. A sling according to claim 1 wherein the sling is constructed for treating female incontinence with a surgical procedure that includes a vaginal incision, and the repositioning means is without any structure that extends through the vaginal incision.

3. A sling according to claim 1 wherein the sling is initially placed via an access incision such as a vaginal incision, and the repositioning means affords post operative loosening of the sling after the vaginal incision is closed without any subsequent vaginal incision and without any structure extending through the original vaginal incision.

4. A sling according to claim 1 wherein the repositioning means transfers sling tightening or sling loosening forces along the sling while avoiding permanent deformation of the sling.

5. A sling according to claim 1, wherein the repositioning means comprises at least one filament threaded along the mesh.

6. A sling according to claim 5, wherein the filament is attached to the mesh at the ends of the support portion.

7. A sling according to claim 1, wherein the repositioning means comprises at least one filament integrally woven in the mesh.

8. A sling according to claim 1, wherein the mesh has a length, and the repositioning means comprises a plurality of filaments that are each threaded along substantially the entire length of the mesh.

9. A sling according to claim 8 wherein the filaments extend from an edge of the support portion to the other edge of the support portion.

10. A sling according to claim 1, wherein the mesh of the support portion is woven and the repositioning means comprises a portion of the support portion that is more tightly woven than another portion of the support portion.

11. A sling according to claim 1, wherein the sling comprises a woven mesh and the repositioning means comprises a portion of the mesh that is more tightly woven than another portion of the sling.

12. A sling according to claim 1, wherein the repositioning means is constructed to afford transfer of at least some of a repositioning force applied to the sling to an end of the support portion.

13. A sling according to claim 1 wherein the sling includes synthetic material.

14. A sling according to claim 1, wherein the repositioning member includes a coating selected from the group consisting of medicaments, hormones, antibiotics, antimicrobials, dyes, silicone elastomers, polyurethanes, radiopaque substances, anti-bacterial substances.

15. A sling according to claim 1 wherein the sling includes a coating selected from the group consisting of medicaments, hormones, antibiotics, antimicrobials, dyes, silicone elastomers, polyurethanes, raidopaque substances, anti-bacterial substances.

16. A sling according to claim 1 wherein at least a portion of the sling is constructed from a bioabsorbable material constructed to retain predetermined properties after implantation for at least a predetermined amount of time.

17. A sling according to claim 1 wherein at least a portion of the repositioning member is a resorbable material constructed to retain predetermined properties after implantation for at least a predetermined amount of time.

18. A sling according to claim 1 wherein the repositioning member is woven in a weave pattern along the mesh so that the weave pattern affords an indication of proper sling orientation after implantation.

19. A sling according to claim 18 wherein a majority of the repositioning member protrudes above the second major side of the support portion of the sling.

20. A sling according to claim 1 further including a sheath.

21. A sling according to claim 20 wherein the sheath includes indicia means for assisting the surgeon in properly orienting the sling relative to the urethra.

22. A sling according to claim 21 wherein the sheath includes separation means selected from the group consisting of tear scores, perforations or holes.

23. A sling according to claim 20 wherein the sheath comprises first and second sections that overlap adjacent the support portion of the sling.

24. A sling according to claim 1 wherein the sling and repositioning means are of contrasting colors and each of the sling and the repositioning means are of a color that contrasts with the physiological environment in which they will be implanted to assist a surgeon in identifying and distinguishing between the sling, the repositioning means and the physiological environment.

25. A sling according to claim 1 wherein the sling mesh is braided.

26. A sling according to claim 1 wherein the sling mesh is knitted.

27. A sling according to claim 1 wherein the sling has a length, the repositioning means comprises a one piece, elongate member threaded in the mesh and extending axially along substantially the entire length of the sling, and wherein the one piece, elongate member is attached to the sling at the ends of the support portion.

28. A sling according to claim 27 wherein the sling includes a means for locating and detaching the one piece, elongate member.

29. A sling according to claim 28 wherein the means for locating and detaching the one piece, elongate member comprises loops in the elongate, one piece member at the ends of the support portion.

30. A sling according to claim 1 wherein the repositioning means comprises a handle situated in the support portion.

31. A sling for treating urinary incontinence in a patient comprising:

first and second major surfaces, a pair of end portions, a support portion for placement in a therapeutically effective position relative to a physiological environment intended to be supported, the support portion being constructed of autologous material, and having a pair of ends, and repositioning means, associated with the sling, for transferring sling tightening or sling loosening forces along the sling to afford effective repositioning of the sling without adversely affecting the therapeutic effect of the sling, wherein the sling includes a removable sheath and the repositioning means affords permanent tightening of the sling the sling is partially implanted and the sheath is removed, by pulling on the sling and repositioning means at a superpubic location.

32. A method of treating urinary incontinence in a patient comprising the steps of:

establishing a pathway in tissue on both sides of a patient's urethra, the pathways extending between an abdominal wall of the patient and a pubic space of the patient;

atraumatically dilating the pathways after the establishment of the pathways;

introducing a sling material having repositioning means into the pathways while the pathways are being atraumatically dilated;

positioning the sling material in the pathways in a therapeutic relationship relative to the urethra, and so that the sling extends upward toward the abdominal wall; and repositioning the sling, using the repositioning means, to support the urethra of the patient.

33. A method according to claim 32, wherein the step of positioning the sling comprises the step of positioning the sling proximate the patient's urethra.

34. A method according to claim 32 wherein the step of establishing a pathway comprises making an original vaginal incision and the step of repositioning the sling occurs after the vaginal incision is closed and is accomplished without any structure passing through the original vaginal incision.

35. A method according to claim 32 wherein the step of repositioning the sling occurs during the surgical procedure.

36. A method of treating urinary incontinence in a patient comprising the steps of:

providing a sling with repositioning means;

creating a pathway in tissue extending between an abdominal wall of the patient and a pubic region of the patient;

positioning a sling material into the pathways so that the sling material is in a therapeutic relationship relative to the urethra of the patient and so that the sling extends upwards toward the abdominal wall; and loosening the sling material by using the repositioning means.

* * * * *